United States Patent
Jeanmart et al.

(10) Patent No.: US 9,051,300 B2
(45) Date of Patent: Jun. 9, 2015

(54) HERBICIDES

(75) Inventors: Stephane André Marie Jeanmart, Stein (CH); Adrian Longstaff, Bracknell (GB); Christopher John Mathews, Bracknell (GB); Claire Janet Russell, Bracknell (GB); Russell Colin Viner, Bracknell (GB); Frances Kathryn Wood, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 0 days.

(21) Appl. No.: 13/388,233

(22) PCT Filed: Jul. 29, 2010

(86) PCT No.: PCT/GB2010/001449
§ 371 (c)(1),
(2), (4) Date: Apr. 16, 2012

(87) PCT Pub. No.: WO2011/012862
PCT Pub. Date: Feb. 3, 2011

(65) Prior Publication Data
US 2012/0202691 A1  Aug. 9, 2012

(30) Foreign Application Priority Data

Jul. 31, 2009 (GB) ................................. 0913436.2
Jul. 27, 2010 (GB) ................................. 1012582.1

(51) Int. Cl.

| | | |
|---|---|---|
| C07D 277/24 | (2006.01) | |
| A01N 43/78 | (2006.01) | |
| C07D 405/08 | (2006.01) | |
| A01N 43/10 | (2006.01) | |
| A01N 43/54 | (2006.01) | |
| A01N 43/56 | (2006.01) | |
| C07D 401/08 | (2006.01) | |
| C07D 409/08 | (2006.01) | |
| C07D 417/08 | (2006.01) | |
| C07D 417/14 | (2006.01) | |

(52) U.S. Cl.
CPC .............. *C07D 405/08* (2013.01); *A01N 43/10* (2013.01); *A01N 43/54* (2013.01); *A01N 43/56* (2013.01); *A01N 43/78* (2013.01); *C07D 401/08* (2013.01); *C07D 409/08* (2013.01); *C07D 417/08* (2013.01); *C07D 417/14* (2013.01)

(58) Field of Classification Search
CPC .............................. C07D 277/24; A01N 43/78
USPC ........................................... 548/146; 504/266
See application file for complete search history.

(56) References Cited

FOREIGN PATENT DOCUMENTS

| JP | 60246037 | 12/1985 |
|---|---|---|
| WO | 02/088098 | 11/2002 |
| WO | WO-02088098 | * 11/2002 |

* cited by examiner

*Primary Examiner* — Yong Chu
*Assistant Examiner* — Sonya Wright
(74) *Attorney, Agent, or Firm* — R. Kody Jones

(57) ABSTRACT

The invention relates to a compound of formula (I), which is suitable for use as a herbicide wherein G is hydrogen or an agriculturally acceptable metal, sulfonium, ammonium or latentiating group; Q is a unsubstituted or substituted $C_3$-$C_8$ saturated or mono-unsaturated heterocyclyl containing at least one heteroatom selected from O, N and S, or Q is heteroaryl or substituted heteroaryl; m is 1, 2 or 3; and Het is an optionally substituted monocyclic or bicyclic heteroaromatic ring; and wherein the compound is optionally an agronomically acceptable salt thereof.

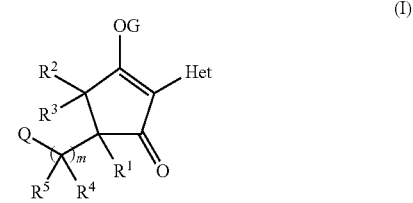

(I)

28 Claims, No Drawings

HERBICIDES

This application is a 371 of International Application No. PCT/GB2010/001449 filed Jul. 29, 2010, which claims priority to GB 0913436.2 filed Jul. 31, 2009,and GB 1012582.1 filed Jul. 27, 2010, the contents of which are incorporated herein by reference.

The present invention relates to novel, herbicidally active heteroaryl diones or derivatives thereof, specifically herbicidally active heteroaryl-substituted cyclic diones or derivatives thereof, more specifically herbicidally active 2-heteroaryl-cyclopentane-1,3-diones or derivatives thereof; to processes for the preparation of these compounds or derivatives; to compositions comprising these compounds or derivatives; and to their use in controlling weeds, especially in crops of useful plants, or in inhibiting undesired plant growth.

Heteroaryl cyclic dione compounds having herbicidal action are described in U.S. Pat. No. 4,678,501. WO 96/16061 A1 (Bayer AG) discloses thiophene-substituted cyclic diones, wherein the cyclic dione is selected from one of eight heterocyclic or carbocyclic classes such as cyclopentanedione or cyclohexanedione, and the use of these diones as pesticides and herbicides. WO 02/088098 A1 (Bayer AG) discloses thiazolyl-substituted carbocyclic 1,3-diones, specifically 2-(thiazolyl)-cyclopentane-1,3-diones and 2-(thiazolyl)-cyclohexane-1,3-diones, and derivatives thereof, and their uses as pesticidal agents, herbicides, and fungicides. WO 03/035643 A1 (Bayer Cropscience AG) discloses 5-membered-heterocycles substituted by oxo and also substituted by either N-linked-pyrazolyl or C— linked-pyrazolyl, and their uses as phytosanitary products, microbicides, and herbicides. WO 2009/000533 A1 (Syngenta Limited) discloses inter alia pyrandione, thiopyrandione and cyclohexanetrione compounds, which are substituted by an optionally substituted monocyclic or bicyclic heteroaromatic ring such as thiophene or thiazolyl, and their use as herbicides. WO 2009/015877 A1 (Syngenta Limited) discloses bicyclic (bridged carbocyclic) diones, which are substituted by an optionally substituted monocyclic or bicyclic heteroaromatic ring such as thiophene or thiazolyl, and their use as herbicides. WO 2009/086041 A1 (E.I. DuPont de Nemours & Co.) discloses herbicidal pyridazinone derivatives substituted by -G-J where G and J are each independently an optionally substituted phenyl ring or an optionally substituted 5- or 6-membered heteroaromatic ring; in WO 2009/086041, G can for example be substituted 1H-pyrazol-1-yl.

U.S. Pat. No. 4,338,122 (Union Carbide Corp.) discloses 2-aryl-1,3-cyclopentanedione compounds exhibiting acaricidal and herbicidal activity. WO 96/01798 (Bayer AG) and its derived patent U.S. Pat. No. 5,840,661 disclose 2-aryl-cyclopentane-1,3-dione derivatives and their use as pesticides and herbicides. WO 01/74770 (Bayer AG), its equivalent US 2003/0216260 A1, and its derived AU patent 782557 (AU 200144215C) disclose $C_2$-phenyl-substituted cyclic (heterocyclic or carbocyclic) ketoenols and their use as pesticides and herbicides. WO 2008/071405 A1 (Syngenta Limited et al.) discloses inter alia pyrandione, thiopyrandione and cyclohexanetrione compounds, which are substituted by a phenyl ring which is substituted by optionally substituted aryl or optionally substituted heteroaryl, and their use as herbicides. WO 2008/145336 A1 (Syngenta Limited) discloses bicyclic (bridged carbocyclic) diones, which are substituted by a substituted phenyl ring, and their use as herbicides.

Copending patent application PCT/EP2009/058250, filed on 1 Jul. 2009 and published on 7 Jan. 2010 as WO 2010/000773 A1 (Syngenta Limited), discloses 5-(heterocyclylalkyl)-3-hydroxy-2-phenyl-cyclopent-2-enones, and their 2-phenyl-4-(heterocyclylalkyl)-cyclopentane-1,3-dione tautomers, and derivatives thereof, as herbicides. Copending patent application PCT/EP2009/066712, filed on 9 Dec. 2009 and published on 24 Jun. 2010 as WO 2010/069834 A1 (Syngenta Participations AG and Syngenta Limited), discloses 2-phenyl-4-(heteroarylmethyl)-cyclopentane-1,3-diones, and derivatives thereof as herbicides.

Novel heteroaryl dione compounds and derivatives thereof, having herbicidal and/or plant-growth-inhibiting properties, have now been found.

The present invention accordingly relates to a compound of formula (I)

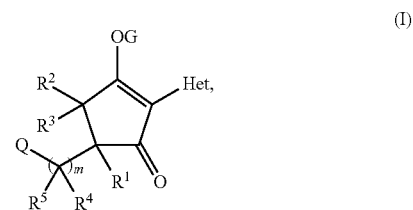

wherein:
G is hydrogen or an agriculturally acceptable metal, sulfonium, ammonium or latentiating group; and
$R^1$, $R^2$, $R^3$, $R^4$ and $R^5$ are independently hydrogen, halogen, $C_1$-$C_5$alkyl, $C_1$-$C_5$haloalkyl, $C_1$-$C_6$alkoxy, $C_1$-$C_5$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_5$alkylthio, $C_1$-$C_5$alkylsulfinyl, $C_1$-$C_6$alkylsulfonyl, $C_1$-$C_5$haloalkylsulfonyl, $C_1$-$C_5$alkoxysulfonyl, $C_1$-$C_5$haloalkoxysulfonyl, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or benzyl or benzyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or $C_3$-$C_6$cycloalkyl$C_1$-$C_3$alkyl in which a ring or chain methylene group is optionally replaced by an oxygen or sulfur atom; and/or
$R^2$ and $R^3$ or $R^4$ and $R^5$ together with the carbon atoms to which they are attached form an optionally substituted 3- to 8-membered ring, optionally containing an oxygen, sulphur or nitrogen atom; and/or
$R^1$ and $R^4$ together form a bond; and
Q is $C_3$-$C_8$ saturated or mono-unsaturated heterocyclyl containing at least one heteroatom selected from O, N and S, unsubstituted or substituted by a residue of formula =O, =N—$R^{10}$, $C_1$-$C_4$alkyl, $C_1$-$C_4$haloalkyl, $C_1$-$C_4$alkoxy$C_1$-$C_2$alkyl, $C_3$-$C_6$cycloalkyl, phenyl or phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, where $R^{13}$ is $C_1$-$C_5$alkyl, $C_1$-$C_6$haloalkyl, $C_3$-$C_7$cycloalkyl, $C_1$-$C_5$alkoxy, $C_1$-$C_5$haloalkoxy, $C_1$-$C_5$alkylsulfinyl, $C_1$-$C_6$alkylsulfonyl, $C_1$-$C_5$alkylcarbonyl, $C_1$-$C_6$haloalkylcarbonyl, $C_1$-$C_5$alkoxycarbonyl, $C_1$-$C_6$alkylaminocarbonyl, $C_2$-$C_8$dialkylaminocarbonyl, $C_1$-$C_5$haloalkylsulfinyl or $C_1$-$C_6$haloalkylsulfonyl; or Q is an heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl;
and
m is 1, 2 or 3; and
Het is an optionally substituted monocyclic or bicyclic heteroaromatic ring;
wherein, in the optionally substituted monocyclic or bicyclic heteroaromatic ring which is Het, the optional substituents are selected, independently, from halogen, nitro, cyano, rhodano, isothiocyanate, $C_1$-$C_5$alkyl, $C_1$-$C_5$haloalkyl, $C_1$-$C_5$alkoxy($C_1$-$C_5$) alkyl, $C_2$-$C_6$alkenyl, $C_2$-$C_6$haloalkenyl, $C_2$-$C_6$alkynyl, $C_3$-$C_7$cycloalkyl (itself optionally substituted with $C_1$-$C_5$alkyl or halogen), $C_{5-7}$cycloalkenyl (itself optionally substituted with $C_1$-$C_5$alkyl or halogen), hydroxy, $C_1$-$C_{10}$alkoxy, $C_1$-$C_{10}$alkoxy($C_1$-$C_{10}$)alkoxy, tri($C_1$-$C_4$)alkylsilyl($C_1$-$C_5$)alkoxy, $C_1$-$C_6$alkoxycarbonyl($C_1$-$C_{10}$)alkoxy, $C_1$-$C_{10}$haloalkoxy, aryl($C_1$-$C_4$)alkoxy (where the aryl group is optionally substituted with halogen or $C_1$-$C_5$alkyl), $C_3$-$C_7$cycloalkyloxy (where the cycloalkyl group is optionally substituted with $C_1$-$C_5$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio, $C_3$-$C_7$cycloalkylthio (where the cycloalkyl group is optionally substituted with $C_1$-$C_5$alkyl or halogen), tri($C_1$-$C_4$)alkylsilyl($C_1$-$C_5$)alkylthio, arylthio, $C_1$-$C_5$alkylsulfonyl, $C_1$-$C_6$haloalkylsulfonyl, $C_1$-$C_5$alkylsulfinyl, $C_1$-$C_5$haloalkylsulfinyl, arylsulfonyl, aryldi($C_1$-$C_4$)alkylsilyl, $C_1$-$C_4$alkyldiarylsilyl, triarylsilyl, $C_1$-$C_{10}$alkylcarbonyl, $HO_2C$, $C_1$-$C_{10}$alkoxycarbonyl, aminocarbonyl, $C_1$-$C_5$alkylaminocarbonyl, di($C_1$-$C_5$alkyl)-aminocarbonyl, N—($C_1$-$C_3$ alkyl)-N—($C_1$-$C_3$alkoxy)aminocarbonyl, $C_1$-$C_5$alkylcarbonyloxy, arylcarbonyloxy, di($C_1$-$C_5$)alkylaminocarbonyloxy, aryl (itself optionally substituted with $C_1$-$C_5$alkyl or halogen), heteroaryl (itself optionally substituted with $C_1$-$C_5$alkyl or halogen), heterocyclyl (itself optionally substituted with $C_1$-$C_5$alkyl or halogen), aryloxy (where the aryl group is optionally substituted with $C_1$-$C_5$alkyl or halogen), heteroaryloxy (where the heteroaryl group is optionally substituted with $C_1$-$C_5$alkyl or halogen), heterocyclyloxy (where the heterocyclyl group is optionally substituted with $C_1$-$C_5$alkyl or halogen), amino, $C_1$-$C_5$alkylamino, di($C_1$-$C_6$)alkylamino, $C_1$-$C_5$alkylcarbonylamino, N—($C_1$-$C_6$)alkylcarbonyl-N—($C_1$-$C_6$)alkylamino, and arylcarbonyl (where the aryl group is itself optionally substituted with halogen or $C_1$-$C_6$alkyl);
or two adjacent positions on the Het heteroaromatic system are optionally cyclised to form a 5, 6 or 7 membered carbocyclic or heterocyclic ring, itself optionally substituted with halogen or $C_1$-$C_6$alkyl;
or, in the optionally substituted monocyclic or bicyclic heteroaromatic ring which is Het, the optional substituents are selected from arylcarbonylamino (where the aryl group is substituted by $C_1$-$C_6$alkyl or halogen), ($C_1$-$C_6$)alkoxycarbonylamino, ($C_1$-$C_6$)alkoxycarbonyl-N—($C_1$-$C_6$)alkylamino, aryloxycarbonylamino (where the aryl group is substituted by $C_1$-$C_6$alkyl or halogen), aryloxycarbonyl-N—($C_1$-$C_6$)alkylamino, (where the aryl group is substituted by $C_1$-$C_6$alkyl or halogen), arylsulphonylamino (where the aryl group is substituted by $C_1$-$C_6$alkyl or halogen), arylsulphonyl-N—($C_1$-$C_6$)alkylamino (where the aryl group is substituted by $C_1$-$C_6$alkyl or halogen), aryl-N—($C_1$-$C_6$)alkylamino (where the aryl group is substituted by $C_1$-$C_6$alkyl or halogen), arylamino (where the aryl group is substituted by $C_1$-$C_6$alkyl or halogen), heteroaryl amino (where the heteroaryl group is substituted by $C_1$-$C_6$alkyl or halogen), heterocyclylamino (where the heterocyclyl group is substituted by $C_1$-$C_6$alkyl or halogen), aminocarbonylamino, $C_1$-$C_6$alkylaminocarbonylamino, di($C_1$-$C_6$)alkylaminocarbonylamino, arylaminocarbonylamino (where the aryl group is substituted by $C_1$-$C_6$alkyl or halogen), aryl-N—($C_1$-$C_6$)alkylaminocarbonylamino (where the aryl group is substituted by $C_1$-$C_6$alkyl or halogen), $C_1$-$C_6$alkylaminocarbonyl-N—($C_1$-$C_6$)alkylamino, di($C_1$-$C_6$)alkylaminocarbonyl-N—($C_1$-$C_6$)alkylamino, arylaminocarbonyl-N—($C_1$-$C_6$)alkylamino (where the aryl group is substituted by $C_1$-$C_6$alkyl or halogen), and aryl-N—($C_1$-$C_6$)alkylaminocarbonyl-N—($C_1$-$C_6$)alkylamino (where the aryl group is substituted by $C_1$-$C_6$alkyl or halogen);
and wherein, when $R^2$ and $R^3$ or $R^4$ and $R^5$ together with the carbon atoms to which they are attached form an optionally substituted 3- to 8-membered ring, optionally containing an oxygen, sulphur or nitrogen atom, then:
when $R^2$ and $R^3$ or $R^4$ and $R^5$ together with the carbon atoms to which they are attached form a carbocycle, then the optional substituents on the carbocycle are selected, independently, from halogen, nitro, cyano, rhodano, isothiocyanato, $C_1$-$C_6$alkyl, $C_1$-$C_6$haloalkyl, $C_1$-$C_6$alkoxy($C_1$-$C_6$)alkyl, $C_2$-$C_6$alkenyl, $C_2$-$C_6$haloalkenyl, $C_2$-$C_6$alkynyl, $C_3$-$C_7$cycloalkyl (itself optionally substituted with $C_1$-$C_6$alkyl or halogen), $C_{5-7}$cycloalkenyl (itself optionally substituted with $C_1$-$C_6$alkyl or halogen), hydroxy, $C_1$-$C_{10}$alkoxy, $C_1$-$C_{10}$alkoxy($C_1$-$C_{10}$)alkoxy, tri($C_1$-$C_4$)alkylsilyl($C_1$-$C_6$)alkoxy, $C_1$-$C_6$alkoxycarbonyl($C_1$-$C_{10}$)alkoxy, $C_1$-$C_{10}$haloalkoxy, aryl($C_1$-$C_4$)alkoxy (where the aryl group is optionally substituted with halogen or $C_1$-$C_6$alkyl), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio, $C_3$-$C_7$cycloalkylthio (where the cycloalkyl group is optionally substituted with $C_1$-$C_6$alkyl or halogen), tri($C_1$-$C_4$)-alkylsilyl($C_1$-$C_6$)alkylthio, arylthio, $C_1$-$C_6$alkylsulfonyl, $C_1$-$C_6$haloalkylsulfonyl, $C_1$-$C_6$haloalkylsulfinyl, arylsulfonyl, tri($C_1$-$C_4$)alkylsilyl, aryldi($C_1$-$C_4$)alkylsilyl, $C_1$-$C_4$alkyldiarylsilyl, triarylsilyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$alkyl)-aminocarbonyl, N—($C_1$-$C_3$ alkyl)-N—($C_1$-$C_3$alkoxy)aminocarbonyl, $C_1$-$C_6$alkylcarbonyloxy, arylcarbonyloxy, di($C_1$-$C_6$)alkylaminocarbonyloxy, aryl (itself optionally substituted with $C_1$-$C_6$alkyl or halogen), heteroaryl (itself optionally substituted with $C_1$-$C_6$alkyl or halogen), heterocyclyl (itself optionally substituted with $C_1$-$C_6$alkyl or halogen), aryloxy (where the aryl group is optionally substituted with $C_1$-$C_6$alkyl or halogen), heteroaryloxy (where the heteroaryl group is optionally substituted with $C_1$-$C_6$alkyl or halogen), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N—($C_1$-$C_6$)alkylcarbonyl-N—($C_1$-$C_6$)alkylamino, and arylcarbonyl (where the aryl group is itself optionally substituted with halogen or $C_1$-$C_6$alkyl);
and when $R^2$ and $R^3$ or $R^4$ and $R^5$ together with the carbon atoms to which they are attached form an optionally substituted 3- to 8-membered ring which contains an oxygen, sulphur or nitrogen atom, then, in the resulting heterocyclyl group, the one or more optional substituents are independently selected from halogen, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, nitro and cyano;

and wherein the latentiating group G is selected from the groups $C_1$-$C_8$alkyl, $C_2$-$C_8$haloalkyl, phenyl$C_1$-$C_8$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_8$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ and $CH_2$—$X^f$—$R^h$;

wherein $X^a$, $X^b$, $X^c$, $X^d$, $X^e$ and $X^f$ are independently of each other oxygen or sulfur;

and wherein $R^a$ is H, $C_1$-$C_{18}$alkyl (e.g. $C_1$-$C_6$alkyl or $C_1$-$C_4$alkyl such as tert-butyl or isopropyl), $C_2$-$C_{18}$alkenyl, $C_2$-$C_{18}$alkynyl, $C_1$-$C_{10}$haloalkyl (e.g. $C_1$-$C_{10}$-fluoroalkyl), $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylamino($C_1$-$C_5$)alkyl, $C_3$-$C_5$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, or phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl (e.g. $C_1$-$C_6$alkyl or $C_1$-$C_4$alkyl such as $C_1$-$C_2$alkyl), $C_3$-$C_{18}$alkenyl, $C_3$-$C_{18}$alkynyl, $C_2$-$C_{10}$haloalkyl (e.g. $C_2$-$C_{10}$fluoroalkyl), $C_1$-$C_{10}$cyanoalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylamino($C_1$-$C_5$)alkyl, $C_3$-$C_5$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, or phenyl or phenyl substituted by $C_1$-$C_3$alkyl, $C_3$haloalkyl, $C_1$-$C_3$alkoxy, $C_1$-$C_3$haloalkoxy, halogen, cyano or nitro, or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro;

$R^c$ and $R^d$ are each independently of each other hydrogen, $C_1$-$C_{10}$alkyl (e.g. $C_1$-$C_6$alkyl or $C_1$-$C_4$alkyl such as $C_1$-$C_2$alkyl), $C_3$-$C_{10}$alkenyl, $C_3$-$C_{10}$alkynyl, $C_2$-$C_{10}$haloalkyl (e.g. $C_2$-$C_{10}$fluoroalkyl), $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_5$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, or phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, or heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, or diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, or $C_3$-$C_7$cycloalkylamino, di-$C_3$-$C_7$cycloalkylamino or $C_3$-$C_7$cycloalkoxy;

or $R^c$ and $R^d$ join together to form a 3-7 membered ring, optionally containing one heteroatom selected from O or S;

$R^e$ is $C_1$-$C_{10}$alkyl (e.g. $C_1$-$C_6$alkyl or $C_1$-$C_4$alkyl such as $C_1$-$C_2$alkyl), $C_2$-$C_{10}$alkenyl, $C_2$-$C_{10}$alkynyl, $C_1$-$C_{10}$haloalkyl (e.g. $C_1$-$C_{10}$fluoroalkyl), $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_8$)alkyl, $C_3$-$C_5$alkynyloxy($C_1$-$C_5$)alkyl, $C_1$-$C_5$alkylthio($C_1$-$C_8$)alkyl, $C_1$-$C_8$alkylsulfinyl($C_1$-$C_5$)alkyl, $C_1$-$C_5$alkylsulfonyl ($C_1$-$C_5$)alkyl, $C_2$-$C_8$alkylideneaminoxy($C_1$-$C_8$)alkyl, $C_1$-$C_5$alkylcarbonyl($C_1$-$C_8$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_8$)alkylcarbonyl-N—($C_1$-$C_5$)alkylamino($C_1$-$C_5$)alkyl, $C_3$-$C_5$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, or phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, or heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, or diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

$R^f$ and $R^g$ are are each independently of each other $C_1$-$C_{10}$alkyl (e.g. $C_1$-$C_6$alkyl or $C_1$-$C_4$alkyl such as $C_1$-$C_2$alkyl), $C_2$-$C_{10}$alkenyl, $C_2$-$C_{10}$alkynyl, $C_1$-$C_{10}$alkoxy, $C_1$-$C_{10}$haloalkyl (e.g. $C_1$-$C_{10}$fluoroalkyl), $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_5$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, or phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, or heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, or diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_8$dialkylamino, or benzyloxy or phenoxy, wherein the benzyl and phenyl groups are in turn optionally substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl (e.g. $C_1$-$C_6$alkyl or $C_1$-$C_4$alkyl such as $C_1$-$C_2$alkyl), $C_3$-$C_{10}$alkenyl, $C_3$-$C_{10}$alkynyl, $C_1$-$C_{10}$haloalkyl (e.g. $C_1$-$C_{10}$fluoroalkyl), $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_5$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, or phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

and wherein the compound is optionally an agronomically acceptable salt thereof.

In the substituent definitions of the compounds of the formula I, each alkyl moiety either alone or as part of a larger group (such as alkoxy, alkylthio, alkoxycarbonyl, alkylcarbonyl, alkylaminocarbonyl, dialkylaminocarbonyl or cycloalkylalkyl) is a straight or branched chain and is, for example, independently methyl, ethyl, n-propyl, n-butyl, n-pentyl, n-hexyl, isopropyl, n-butyl, sec-butyl, isobutyl, tert-butyl or neopentyl. The alkyl groups are suitably $C_1$-$C_6$alkyl groups, but are preferably $C_1$-$C_4$alkyl or $C_1$-$C_3$alkyl groups, and, more preferably, $C_1$-$C_2$alkyl groups.

Alkenyl and alkynyl moieties can be in the form of straight or branched chains, and the alkenyl moieties, where appropriate, can be either the (E)- or (Z)-configuration. Examples are vinyl, allyl and propargyl. Alkenyl and alkynyl moieties can contain one or more double and/or triple bonds in any combination. It is understood, that allenyl is included in these terms.

Halogen is fluorine, chlorine, bromine or iodine, preferably fluorine, chlorine or bromine.

Haloalkyl (e.g. fluoroalkyl) groups are alkyl groups which are substituted with one or more of the same or different halogen (e.g. fluorine) atoms and are suitably, independently, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$; preferably, independently, $CF_3$, $CF_2H$, $FCH_2$, $CH_3CHF$, $(CH_3)_2CF$, $CF_3CH_2$ or $CHF_2CH_2$.

The terms "heteroaryl" and/or "heteroaromatic" preferably refer to an aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulphur. Examples of such groups include independently furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl. Preferred examples of heteroaromatic radicals include independently pyridyl, pyrimidinyl, triazinyl, thienyl, furyl, oxazolyl, isoxazolyl, 2,1,3-benzoxadiazolyl or thiazolyl.

Another group of preferred heteroaryls comprises independently pyrazolyl, 1,2,3-triazolyl, 1,2,4-triazolyl, pyridazinyl, pyrazinyl, quinolinyl, isoquinolinyl, cinnolinyl, quinazolinyl or quinoxalinyl.

The term "heterocyclyl" preferably refers to a non-aromatic preferably monocyclic or bicyclic ring systems containing up to 7 atoms including one or more (preferably one or two) heteroatoms selected from O, S and N. Examples of such rings include 1,3-dioxolane, oxetane, tetrahydrofuran, tetrahydropyran, morpholine, thiomorpholin and piperazine. When present, the optional substituents on heterocyclyl include $C_1$-$C_6$alkyl and $C_1$-$C_6$haloalkyl as well as those optional substituents given above for an alkyl moiety.

Cycloalkyl includes preferably independently cyclopropyl, cyclobutyl, cyclopentyl or cyclohexyl. Cycloalkylalkyl is preferentially cyclopropylmethyl.

Carbocyclic rings include independently aryl, cycloalkyl or carbocyclic groups, and cycloalkenyl groups. In the compounds of the formula I, each aryl group, either alone or as part of a larger group (e.g. aryloxy etc.), is independently preferably phenyl.

When present, the optional substituents on aryl (preferably phenyl), heteroaryl and/or carbocycles are preferably selected, independently, from halogen, nitro, cyano, rhodano, isothiocyanato, $C_1$-$C_6$alkyl, $C_1$-$C_6$haloalkyl, $C_1$-$C_6$alkoxy($C_1$-$C_6$)alkyl, $C_2$-$C_6$alkenyl, $C_2$-$C_6$haloalkenyl, $C_2$-$C_6$alkynyl, $C_3$-$C_7$cycloalkyl (itself optionally substituted with $C_1$-$C_6$alkyl or halogen), $C_{6-7}$cycloalkenyl (itself optionally substituted with $C_1$-$C_6$alkyl or halogen), hydroxy, $C_1$-$C_{10}$alkoxy, $C_1$-$C_{10}$alkoxy($C_1$-$C_{10}$)alkoxy, tri($C_1$-$C_4$)alkylsilyl($C_1$-$C_6$)alkoxy, $C_1$-$C_6$alkoxycarbonyl($C_1$-$C_{10}$)alkoxy, $C_1$-$C_{10}$haloalkoxy, aryl($C_1$-$C_4$)alkoxy (where the aryl group is optionally substituted with halogen or $C_1$-$C_6$alkyl), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio, $C_3$-$C_7$cycloalkylthio (where the cycloalkyl group is optionally substituted with $C_1$-$C_6$alkyl or halogen), tri($C_1$-$C_4$)-alkylsilyl($C_1$-$C_6$)alkylthio, arylthio, $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl, aryldi($C_1$-$C_4$)alkylsilyl, $C_1$-$C_4$alkyldiarylsilyl, triarylsilyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$alkyl)-aminocarbonyl, N—($C_1$-$C_3$ alkyl)-N—($C_1$-$C_3$alkoxy)aminocarbonyl, $C_1$-$C_6$alkylcarbonyloxy, arylcarbonyloxy, di($C_1$-$C_6$)alkylaminocarbonyloxy, aryl (itself optionally substituted with $C_1$-$C_6$alkyl or halogen), heteroaryl (itself optionally substituted with $C_1$-$C_6$alkyl or halogen), heterocyclyl (itself optionally substituted with $C_1$-$C_6$alkyl or halogen), aryloxy (where the aryl group is optionally substituted with $C_1$-$C_6$alkyl or halogen), heteroaryloxy (where the heteroaryl group is optionally substituted with $C_1$-$C_6$alkyl or halogen), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N—($C_1$-$C_6$)alkylcarbonyl-N—($C_1$-$C_6$)alkylamino, and arylcarbonyl (where the aryl group is itself optionally substituted with halogen or $C_1$-$C_6$alkyl); or two adjacent positions on an aryl or heteroaryl system may be cyclised to form a 5, 6 or 7 membered carbocyclic or heterocyclic ring, itself optionally substituted with halogen or $C_1$-$C_6$alkyl. Further substituents for aryl or heteroaryl include arylcarbonylamino (where the aryl group is substituted by $C_1$-$C_6$alkyl or halogen), ($C_1$-$C_6$)alkoxycarbonylamino, ($C_1$-$C_6$)alkoxycarbonyl-N—($C_1$-$C_6$)alkylamino, aryloxycarbonylamino (where the aryl group is substituted by $C_1$-$C_6$alkyl or halogen), aryloxycarbonyl-N—($C_1$-$C_6$)alkylamino, (where the aryl group is substituted by $C_1$-$C_6$alkyl or halogen), arylsulphonylamino (where the aryl group is substituted by $C_1$-$C_6$alkyl or halogen), arylsulphonyl-N—($C_1$-$C_6$)alkylamino (where the aryl group is substituted by $C_1$-$C_6$alkyl or halogen), aryl-N—($C_1$-$C_6$)alkylamino (where the aryl group is substituted by $C_1$-$C_6$alkyl or halogen), arylamino (where the aryl group is substituted by $C_1$-$C_6$alkyl or halogen), heteroaryl amino (where the heteroaryl group is substituted by $C_1$-$C_6$alkyl or halogen), heterocyclylamino (where the heterocyclyl group is substituted by $C_1$-$C_6$alkyl or halogen), aminocarbonylamino, $C_1$-$C_6$alkylaminocarbonylamino, di($C_1$-$C_6$)alkylaminocarbonylamino, arylaminocarbonylamino (where the aryl group is substituted by $C_1$-$C_6$alkyl or halogen), aryl-N—($C_1$-$C_6$)alkylaminocarbonylamino (where the aryl group is substituted by $C_1$-$C_6$alkyl or halogen), $C_1$-$C_6$alkylaminocarbonyl-N—($C_1$-$C_6$)alkylamino, di($C_1$-$C_6$)alkylaminocarbonyl-N—($C_1$-$C_6$)alkylamino, arylaminocarbonyl-N—($C_1$-$C_6$)alkylamino (where the aryl group is substituted by $C_1$-$C_6$alkyl or halogen) and aryl-N—($C_1$-$C_6$)alkylaminocarbonyl-N—($C_1$-$C_6$)alkylamino (where the aryl group is substituted by $C_1$-$C_6$alkyl or halogen).

For substituted heterocyclyl groups it is preferred that one or more substituents are independently selected from halogen, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, nitro and cyano. It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected $C_1$-$C_6$alkyl groups. When heterocyclic rings are formed by joining two groups on an N atom, the resulting rings are suitably pyrrolidine, piperidine, thiomorpholine and morpholine each of which may be substituted by one or two independently selected $C_1$-$C_6$alkyl groups.

The invention relates also to the agriculturally acceptable salts which the compounds of formula I are able to form with transition metal, alkali metal or alkaline earth metal bases, amines, quaternary ammonium bases or tertiary sulfonium bases.

Among the transition metal, alkali metal or alkaline earth metal salt capable of forming transition metal, alkali metal or alkaline earth metal salts (i.e. where G is a metal), special mention should be made of the hydroxides of copper, iron, lithium, sodium, potassium, magnesium or calcium; and preferably the hydroxides, bicarbonates or carbonates of sodium or potassium.

Examples of amines suitable for ammonium salt formation (i.e. where G is an ammonium) include ammonia, or primary, secondary or tertiary $C_1$-$C_{18}$alkylamines, $C_1$-$C_4$hydroxyalkylamines or $C_2$-$C_4$alkoxyalkyl-amines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine or ethoxyethylamine; or heterocyclic amines, for example pyridine, quinoline, isoquinoline, morpholine, piperidine, pyrrolidine, indoline, quinuclidine or azepine; or primary arylamines, for example anilines, methoxyanilines, ethoxyanilines, o-, m- or p-toluidines, phenylene-diamines, benzidines, naphthylamines or o-, m- or p-chloroanilines; but especially triethylamine, isopropylamine or di-isopropylamine.

Preferred quaternary ammonium bases suitable for salt formation (i.e. where G is an ammonium) correspond, for example, to the formula $[N(R_aR_bR_cR_d)]OH$, wherein $R_a$, $R_b$, $R_c$ and $R_d$ are each independently of the others hydrogen or $C_1$-$C_4$alkyl. Further suitable tetraalkylammonium bases with other anions can be obtained, for example, by anion exchange reactions.

Preferred tertiary sulfonium bases suitable for salt formation (i.e. where G is a sulfonium) correspond, for example, to the formula $[SR_eR_fR_g]OH$, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O—C=C—C=O unit.

The compounds of formula I according to the invention also include hydrates, for example hydrates which may be formed during salt formation.

The latentiating group G is selected to allow its removal by one or a combination of biochemical, chemical or physical processes to afford compounds of formula I where G is H before, during or following (preferably during or following) application to the treated area or plants. Examples of these processes include enzymatic cleavage (e.g. enzymatic cleavage of esters), chemical hydrolysis and photolysis. Compounds bearing such groups G may, in some cases, offer certain advantage(s), such as: improved penetration of the cuticula of the plants treated; increased tolerance of crops; improved compatibility or stability in formulated mixtures containing other herbicides, herbicide safeners, plant growth regulators, fungicides and/or insecticides; and/or reduced leaching in soils; in particular improved penetration of the cuticula of the plants treated.

In the latentiating group G, preferably, $X^a$, $X^b$, $X^c$, $X^d$, $X^e$ and/or $X^f$ are oxygen. More preferably, all of $X^a$, $X^b$, $X^c$, $X^d$, $X^e$ and $X^f$ are oxygen.

Preferably, the latentiating group G is a group —C($X^a$)—$R^a$ or —C($X^b$)—$X^c$—$R^b$.

More preferably, the latentiating group G is a group —C($X^a$)—$R^a$ or —C($X^b$)—$X^c$—$R^b$, wherein $R^a$ is hydrogen or $C_1$-$C_{18}$alkyl (more preferably, hydrogen or $C_1$-$C_6$alkyl, still more preferably $C_1$-$C_6$alkyl, most preferably $C_1$-$C_4$alkyl such as tert-butyl or isopropyl), $R^b$ is $C_1$-$C_{18}$alkyl (more preferably, $C_1$-$C_6$alkyl, still more preferably $C_1$-$C_6$alkyl such as $C_1$-$C_2$alkyl), and the meanings of $X^a$, $X^b$ and $X^c$ are as defined above (more preferably, $X^a$, $X^b$ and $X^c$ are oxygen).

It is preferred that G is hydrogen, an alkali metal or alkaline earth metal, where hydrogen is especially preferred.

Depending on the nature of the substituents, compounds of formula I may exist in different isomeric forms. When G is hydrogen, for example, compounds of formula I may exist in different tautomeric forms (one dione tautomer and two different keto-enol tautomers), as shown in the following scheme:

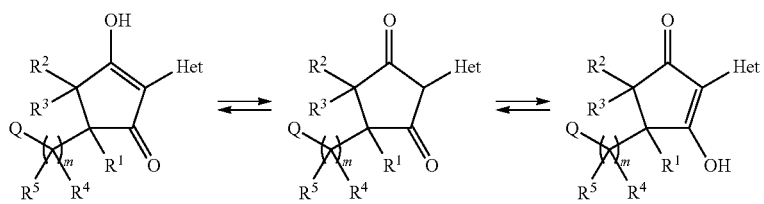

This invention covers all such isomers and tautomers and mixtures thereof in all proportions. Also, when substituents contain double bonds, cis- and trans-isomers can exist. These isomers, too, are within the scope of the claimed compounds of the formula I.

In a preferred group of compounds of the formula (I), $R^1$ is hydrogen, halogen, $C_1$-$C_6$alkyl, $C_1$-$C_6$haloalkyl, $C_1$-$C_6$alkoxy or $C_1$-$C_6$haloalkoxy, and, more preferably, $R^1$ is hydrogen or methyl.

In another preferred group of the compounds of the formula (I), $R^2$ and $R^3$ independently are hydrogen, halogen, $C_1$-$C_6$alkyl, $C_1$-$C_6$haloalkyl, $C_1$-$C_6$alkoxy or $C_1$-$C_6$haloalkoxy, and, more preferably, $R^2$ and $R^3$ independently are hydrogen or methyl.

Preferably, in the compounds of the formula (I), $R^4$ and $R^5$ independently are hydrogen, halogen, $C_1$-$C_6$alkyl, $C_1$-$C_6$haloalkyl, $C_1$-$C_6$alkoxy or $C_1$-$C_6$haloalkoxy, and, more preferably, $R^4$ and $R^5$ independently are hydrogen or methyl.

Preferred saturated or mono-unsaturated rings Q are those of formulae $Q_1$ to $Q_{107}$

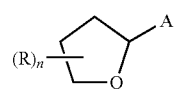 $Q_1$

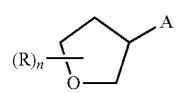 $Q_2$

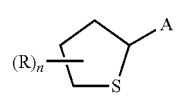 $Q_3$

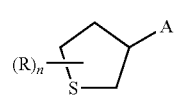 $Q_4$

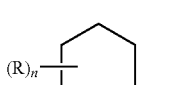 $Q_5$

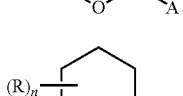 $Q_6$

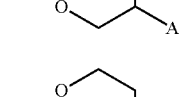 $Q_7$

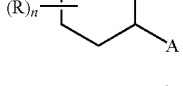 $Q_8$

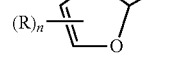 $Q_9$

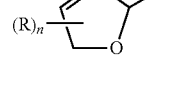 $Q_{10}$

-continued

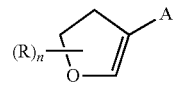 $Q_{11}$

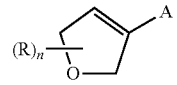 $Q_{12}$

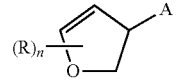 $Q_{13}$

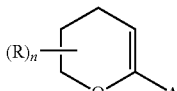 $Q_{14}$

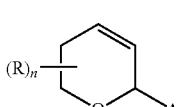 $Q_{15}$

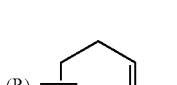 $Q_{16}$

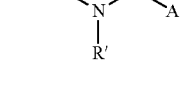 $Q_{17}$

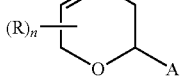 $Q_{18}$

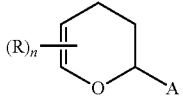 $Q_{19}$

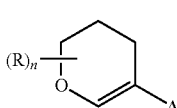 $Q_{20}$

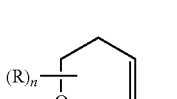 $Q_{21}$

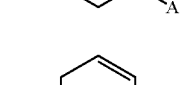 $Q_{22}$

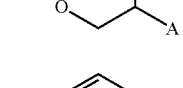 $Q_{23}$

-continued
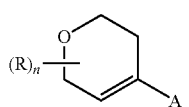 Q24
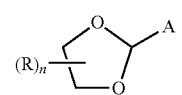 Q25
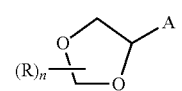 Q26
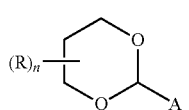 Q27
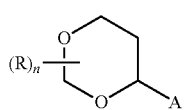 Q28
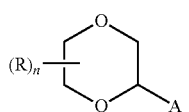 Q29
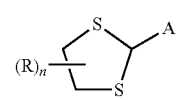 Q30
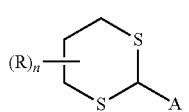 Q31
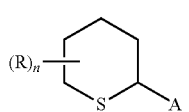 Q32
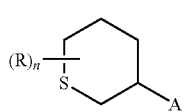 Q33
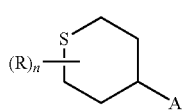 Q34
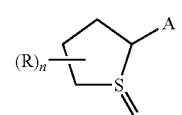 Q35
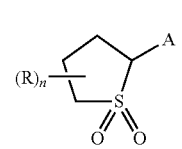 Q36
-continued
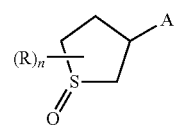 Q37
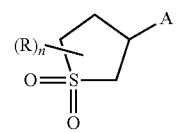 Q38
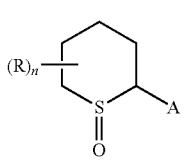 Q39
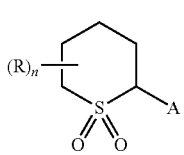 Q40
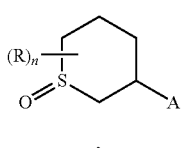 Q41
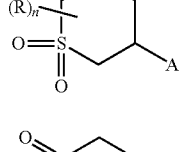 Q42
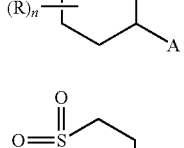 Q43
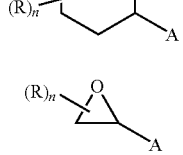 Q44
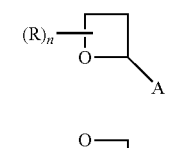 Q45
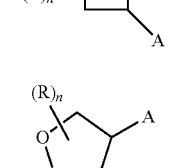 Q46
Q47
Q48

Q49 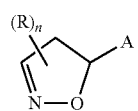
Q50 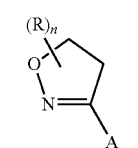
Q51 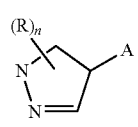
Q52 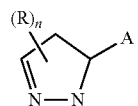
Q53 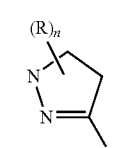
Q54 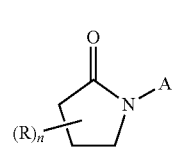
Q55 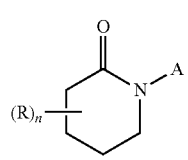
Q56 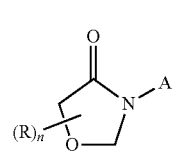
Q57 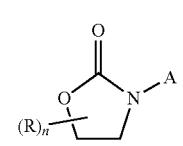
Q58 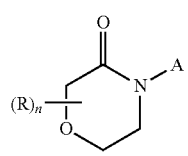
Q59 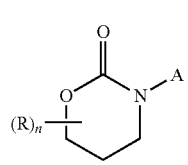
Q60 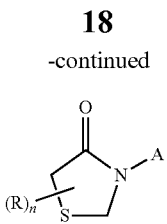
Q61 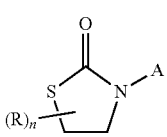
Q62 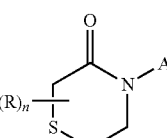
Q63 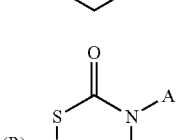
Q64 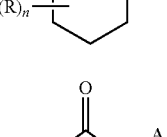
Q65 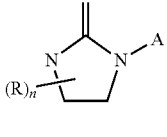
Q66 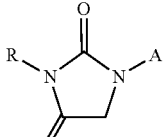
Q67 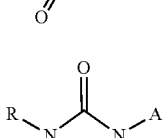
Q68 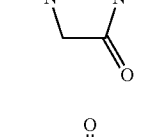
Q69 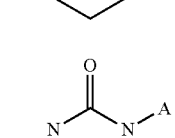

-continued
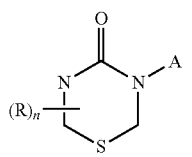 Q70
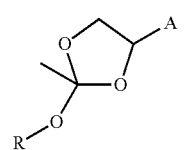 Q71
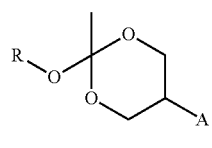 Q72
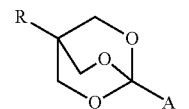 Q73
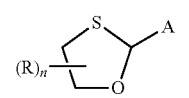 Q74
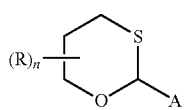 Q75
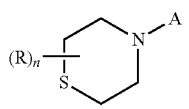 Q76
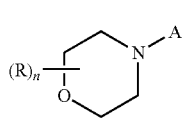 Q77
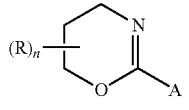 Q78
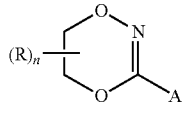 Q79
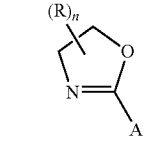 Q80
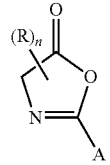 Q81
-continued
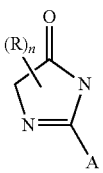 Q82
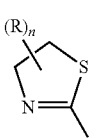 Q83
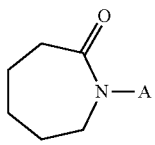 Q84
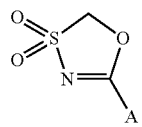 Q85
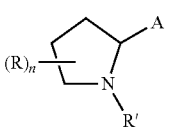 Q86
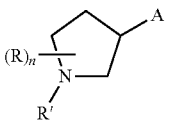 Q87
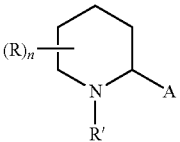 Q88
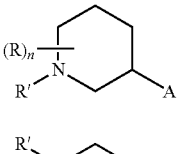 Q89
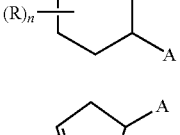 Q90
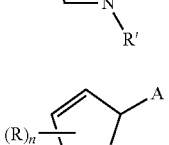 Q91
Q92

-continued

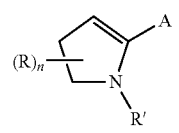 Q93

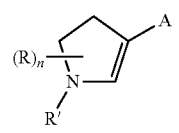 Q94

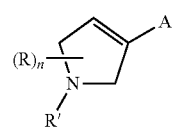 Q95

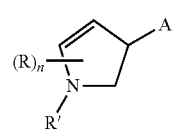 Q96

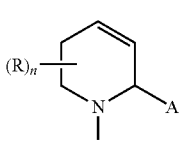 Q97

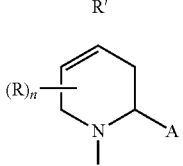 Q98

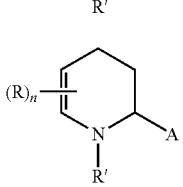 Q99

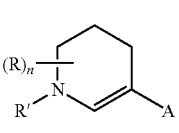 Q100

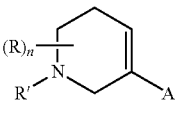 Q101

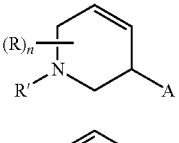 Q102

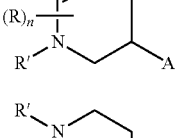 Q103

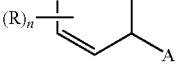 Q104

-continued

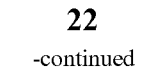 Q105

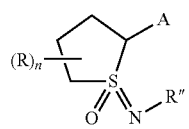 Q106

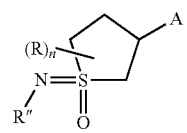 Q107

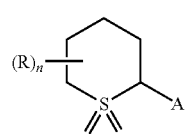 Q108

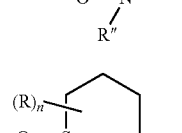 Q109

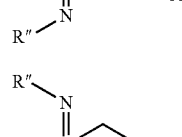 Q110

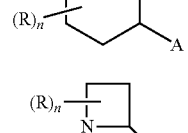 Q106

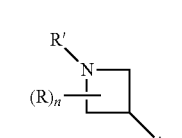 Q107

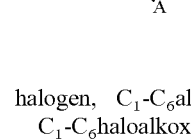

wherein:
R is hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_2$-$C_6$haloalkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl;
R" is hydrogen, $C_1$-$C_6$alkyl, $C_1$-$C_6$haloalkyl, $C_3$-$C_7$cycloalkyl, $C_1$-$C_6$alkoxy, $C_1$-$C_6$haloalkoxy, $C_1$-$C_6$alkylsulfinyl, $C_1$-$C_6$alkylsulfonyl, $C_1$-$C_6$alkylcarbonyl, $C_1$-$C_6$haloalkylcarbonyl, $C_1$-$C_6$alkoxycarbonyl, $C_1$-$C_6$alkylaminocarbonyl, $C_2$-$C_8$dialkylaminocarbonyl, $C_6$-$C_{10}$arylsulfonyl, $C_6$-$C_{10}$arylcarbonyl, $C_6$-$C_{10}$arylaminocarbonyl, $C_7$-$C_{16}$arylalkylaminocarbonyl, $C_1$-$C_9$heteroarylsulfonyl, $C_1$-$C_9$heteroarylcarbonyl, $C_1$-$C_9$heteroarylaminocarbonyl, $C_2$-$C_{15}$heteroarylalkylaminocarbonyl;

R" is hydrogen, $C_1$-$C_6$alkyl, $C_1$-$C_6$haloalkyl, $C_3$-$C_7$cycloalkyl, $C_1$-$C_6$alkoxy, $C_1$-$C_6$haloalkoxy, $C_1$-$C_6$alkylsulfinyl, $C_1$-$C_6$alkylsulfonyl, $C_1$-$C_6$alkylcarbonyl, $C_1$-$C_6$haloalkylcarbonyl, $C_1$-$C_6$alkoxycarbonyl, $C_1$-$C_6$alkylaminocarbonyl, $C_2$-$C_8$dialkylaminocarbonyl, $C_1$-$C_6$haloalkylsulfinyl or $C_1$-$C_6$haloalkylsulfonyl;

n is 0, 1, 2, 3 or 4; and

A denotes the position of attachment to the —$(CR^4R^5)_m$— moiety.

Groups $Q_1$, $Q_2$, $Q_3$, $Q_4$, $Q_5$, $Q_6$, $Q_7$, $Q_{25}$, $Q_{26}$, $Q_{27}$, $Q_{28}$, $Q_{29}$, $Q_{86}$, $Q_{87}$, $Q_{88}$, $Q_{89}$, $Q_{90}$ are more preferred, and groups $Q_1$ to $Q_7$ are particularly preferred.

Preferably, R and R' are independently hydrogen, $C_1$-$C_4$alkyl, $C_1$-$C_4$haloalkyl, $C_1$-$C_4$alkoxy or $C_1$-$C_4$haloalkoxy, and R" is hydrogen, $C_1$-$C_4$alkyl, $C_1$-$C_4$haloalkyl, $C_1$-$C_4$alkoxy, $C_1$-$C_4$haloalkoxy or $C_1$-$C_6$haloalkylcarbonyl.

Preferably, n is 0, 1 or 2. More preferably, n is 0.

In another preferred group of the compounds of the formula (I), Q is a 5- or 6-membered heteroaryl or is a 5- or 6-membered heteroaryl which is substituted one to three times by fluoro, chloro, bromo, methyl, methoxy, cyano or trifluoromethyl.

Preferably, the heteroatoms in these Q moieties are selected from 1 or 2 nitrogen, oxygen or sulphur atoms.

In particular, Q is thienyl, furyl, oxazolyl, isoxazolyl, benzofuryl, thiazolyl, oxazolyl, isothiazolyl, benzothienyl, benzoisothienyl, benzothiazolyl, benzisothiazolyl, benzoxazolyl or benzisoxazolyl, where these rings are optionally substituted one or two times by fluoro, chloro, bromo, methyl, methoxy, cyano or trifluoromethyl.

In particular, Q is pyridyl, pyrimidinyl, pyridazinyl, quinolinyl, isoquinolinyl, cinnolinyl, phthalazinyl, quinazolinyl or quinoxalinyl, where these rings are optionally substituted one or two times by fluoro, chloro, bromo, methyl, methoxy, cyano or trifluoromethyl.

Preferably, in the compounds of the formula (I), m is 1 or 2, and most preferably m is 1.

Preferably, Het is an optionally substituted monocyclic 6-membered nitrogen containing heteroaromatic ring, or, preferably, is an optionally substituted monocyclic 5-membered sulfur or (preferably) nitrogen containing heteroaromatic ring. More preferably, Het is a monocyclic 5-membered sulfur and nitrogen containing heteroaromatic ring.

Even more preferably, Het is a group selected from the formulae $Het_1$ to $Het_{12}$:

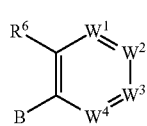

Het₁

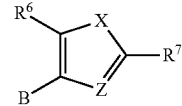

Het₂

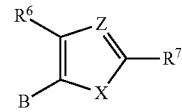

Het₃

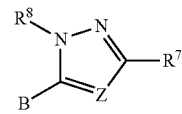

Het₄

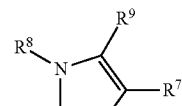

Het₅

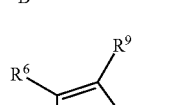

Het₆

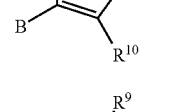

Het₇

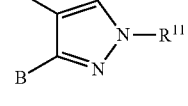

Het₈

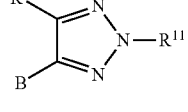

Het₉

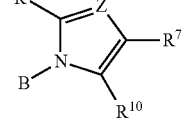

Het₁₀

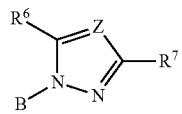

Het₁₁

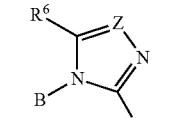

Het₁₂ wherein:
B designates the point of attachment to the ketoenol moiety;
$W^1$ is N or $CR^9$;

$W^2$ and $W^3$ are independently of each other N or $CR^7$;
$W^4$ is N or $CR^{10}$;
with the proviso that at least one of $W^1$, $W^2$, $W^3$ or $W^4$ is N;
X is O, S, or $NR^{12}$;
Z is N or $CR^{13}$;
wherein $R^6$ is hydrogen, halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, nitro or cyano; preferably halogen, $C_1$-$C_2$alkyl, $C_1$-$C_2$haloalkyl (e.g. $CF_3$, $CF_2C_1$, $CF_2H$, $CCl_2H$, $FCH_2$, $ClCH_2$, $BrCH_2$, $CH_3CHF$, $CF_3CH_2$ or $CHF_2CH_2$), vinyl, ethynyl, or methoxy; and even more preferably methyl or ethyl;

$R^7$ is hydrogen, $C_1$-$C_6$alkyl, $C_1$-$C_6$haloalkyl (e.g. $CF_3$, $CF_2C_1$, $CF_2H$, $CCl_2H$, $FCH_2$, $ClCH_2$, $BrCH_2$, $CH_3CHF$, $CF_3CH_2$ or $CHF_2CH_2$), $C_2$-$C_6$alkenyl, $C_2$-$C_6$haloalkenyl, $C_2$-$C_6$alkynyl, $C_3$-$C_6$ cycloalkyl, $C_6$-$C_6$cycloalkenyl, halogen, $C_1$-$C_6$alkoxy, $C_1$-$C_6$alkoxy-$C_1$-$C_6$alkyl, $C_1$-$C_6$haloalkoxy, optionally substituted aryl (e.g. optionally substituted phenyl), optionally substituted aryloxy (e.g. optionally substituted phenoxy), optionally substituted heteroaryl or optionally substituted heteroaryloxy; preferably optionally substituted aryl (e.g. optionally substituted phenyl) or optionally substituted heteroaryl wherein the optional substituents are selected from halogen, $C_1$-$C_2$ alkyl, $C_1$-$C_2$ alkoxy, $C_1$-$C_2$ haloalkyl (e.g. $CF_3$, $CF_2C_1$, $CF_2H$, $CCl_2H$, $FCH_2$, $ClCH_2$, $BrCH_2$, $CH_3CHF$, $CF_3CH_2$ or $CHF_2CH_2$), $C_1$-$C_2$ haloalkoxy, cyano or nitro; and even more preferably phenyl, substituted once, twice or three times, by halogen, $C_1$-$C_2$ alkyl, $C_1$-$C_2$ alkoxy, $C_1$-$C_2$ haloalkyl (e.g. $CF_3$, $CF_2C_1$, $CF_2H$, $CCl_2H$, $FCH_2$, $ClCH_2$, $BrCH_2$, $CH_3CHF$, $CF_3CH_2$ or $CHF_2CH_2$), $C_1$-$C_2$ haloalkoxy or cyano;

$R^8$ is hydrogen, $C_1$-$C_4$ alkyl, $C_2$-$C_3$alkenyl, $C_2$-$C_3$alkynyl, $C_1$-$C_4$ haloalkyl (e.g. $CF_3$, $CF_2C_1$, $CF_2H$, $CCl_2H$, $FCH_2$, $ClCH_2$, $BrCH_2$, $CH_3CHF$, $CF_3CH_2$ or $CHF_2CH_2$), or $C_2$-$C_3$ haloalkenyl; preferably methyl or ethyl;

$R^9$ is hydrogen, methyl, halomethyl (e.g. $CF_3$, $CF_2C_1$, $CF_2H$, $CCl_2H$, $FCH_2$, $ClCH_2$, or $BrCH_2$), or halogen; preferably hydrogen;

$R^{10}$ is hydrogen, halogen, $C_1$-$C_4$ alkyl, $C_1$-$C_4$ haloalkyl (e.g. $CF_3$, $CF_2C_1$, $CF_2H$, $CCl_2H$, $FCH_2$, $ClCH_2$, $BrCH_2$, $CH_3CHF$, $CF_3CH_2$ or $CHF_2CH_2$), $C_2$-$C_4$alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$alkylthio, $C_1$-$C_4$ alkylsulfinyl, $C_1$-$C_4$ alkylsulfonyl or cyano; preferably hydrogen, halogen, methyl or ethyl;

$R^{11}$ is hydrogen, methyl, ethyl, halomethyl (e.g. $CF_3$, $CF_2C_1$, $CF_2H$, $CCl_2H$, $FCH_2$, $ClCH_2$, or $BrCH_2$), haloethyl (e.g. $CH_3CHF$, $CF_3CH_2$ or $CHF_2CH_2$), optionally substituted aryl (e.g. optionally substituted phenyl) or optionally substituted heteroaryl; preferably optionally substituted aryl (e.g. optionally substituted phenyl) or optionally substituted heteroaryl wherein the optional substituents are selected from halogen, $C_1$-$C_2$ alkyl, $C_1$-$C_2$ alkoxy, $C_1$-$C_2$ haloalkyl (e.g. $CF_3$, $CF_2C_1$, $CF_2H$, $CCl_2H$, $FCH_2$, $ClCH_2$, $BrCH_2$, $CH_3CHF$, $CF_3CH_2$ or $CHF_2CH_2$), $C_1$-$C_2$ haloalkoxy, cyano or nitro; even more preferably phenyl, substituted once, twice or three times, by halogen, $C_1$-$C_2$ alkyl, $C_1$-$C_2$ alkoxy, $C_1$-$C_2$ haloalkyl (e.g. $CF_3$, $CF_2C_1$, $CF_2H$, $CCl_2H$, $FCH_2$, $ClCH_2$, $BrCH_2$, $CH_3CHF$, $CF_3CH_2$ or $CHF_2CH_2$), $C_1$-$C_2$ haloalkoxy or cyano;

$R^{12}$ is hydrogen, methyl, ethyl, or halomethyl (e.g. $CF_3$, $CF_2C_1$, $CF_2H$, $CCl_2H$, $FCH_2$, $ClCH_2$, or $BrCH_2$); and $R^{13}$ is hydrogen, methyl, ethyl, halomethyl (e.g. $CF_3$, $CF_2C_1$, $CF_2H$, $CCl_2H$, $FCH_2$, $ClCH_2$, or $BrCH_2$), haloethyl (e.g. $CH_3CHF$, $CF_3CH_2$ or $CHF_2CH_2$), halogen, cyano or nitro; preferably hydrogen.

More preferably, Het is a group of the formula $Het_2$, wherein X is S and Z is N and $R^6$ and $R^7$ are as defined above. Preferably, in this embodiment, $R^6$ is methyl or ethyl. Preferably, in this embodiment, $R^7$ is phenyl, substituted once, twice or three times, by halogen, $C_1$-$C_2$ alkyl, $C_1$-$C_2$ alkoxy, $C_1$-$C_2$ haloalkyl, $C_1$-$C_2$ haloalkoxy or cyano; more preferably, $R^7$ is phenyl substituted once, twice or three times (e.g. once) by halogen (e.g. chlorine); even more preferably, $R^7$ is 4-chlorophenyl.

It is also more preferred that Het is a group of the formula $Het_{10}$, wherein Z is $CR^{13}$ and $R^6$, $R^7$ and $R^{13}$ are as defined above. Preferably, in this embodiment, $R^{13}$ is hydrogen or methyl; more preferably hydrogen. Preferably, in this embodiment, $R^6$ is methyl or ethyl. Preferably, in this embodiment, $R^7$ is phenyl, substituted once, twice or three times, by halogen, $C_1$-$C_2$ alkyl, $C_1$-$C_2$ alkoxy, $C_1$-$C_2$ haloalkyl, $C_1$-$C_2$ haloalkoxy or cyano; more preferably, $R^7$ is phenyl substituted once, twice or three times (e.g. once) by halogen (e.g. chlorine); even more preferably, $R^7$ is 4-chlorophenyl.

It is also preferred that Het is a group of the formula $Het_2$, wherein X is S and Z is $CR^{13}$ and $R^6$, $R^7$ and $R^{13}$ are as defined above. Preferably, in this embodiment, $R^{13}$ is hydrogen. Preferably, in this embodiment, $R^6$ is methyl or ethyl. Preferably, in this embodiment, $R^7$ is phenyl, substituted once, twice or three times, by halogen, $C_1$-$C_2$ alkyl, $C_1$-$C_2$ alkoxy, $C_1$-$C_2$haloalkyl, $C_1$-$C_2$ haloalkoxy or cyano.

It is also preferred that Het is a group of the formula $Het_1$, wherein $W^1$ is $CR^9$, $W^2$ is N, $W^3$ is $CR^7$, $W^4$ is N, and $R^6$, $R^7$ and $R^9$ are as defined above. Preferably, in this embodiment, $R^9$ is hydrogen. Preferably, in this embodiment, $R^6$ is methyl or ethyl. Preferably, in this embodiment, $R^7$ is phenyl, substituted once, twice or three times, by halogen, $C_1$-$C_2$ alkyl, $C_1$-$C_2$ alkoxy, $C_1$-$C_2$ haloalkyl, $C_1$-$C_2$ haloalkoxy or cyano.

In a group of preferred compounds of formula I,
$R^1$ is hydrogen or methyl;
$R^2$ and $R^3$ independently are hydrogen or methyl;
$R^4$ and $R^5$ independently are hydrogen or methyl; and
Q is pyridyl, pyrimidinyl, pyridazinyl, quinolinyl, isoquinolinyl, cinnolinyl, phthalazinyl, quinazolinyl or quinoxalinyl, where these rings are optionally substituted one or two times by fluoro, chloro, bromo, methyl, methoxy, cyano or trifluoromethyl; or Q is thienyl, furyl, oxazolyl, isoxazolyl, benzofuryl, thiazolyl, oxazolyl, isothiazolyl, benzothienyl, benzoisothienyl, benzothiazolyl, benzisothiazolyl, benzoxazolyl or benzisoxazolyl, where these rings are optionally substituted one or two times by fluoro, chloro, bromo, methyl, methoxy, cyano or trifluoromethyl; and
m is 1;
Het is a group $Het_2$ $$Het_2$$

wherein X is S, Z is N, $R^6$ is methyl or ethyl, $R^7$ is 4-chlorophenyl or 4-bromophenyl, and B designates the point of attachment to the ketoenol moiety; and G is hydrogen, an alkali metal or alkaline earth metal. Within this group of preferred compounds of formula I, a particularly preferred group of compounds of formula I are those wherein $R^1$ to $R^5$ and G are hydrogen and Q, Het and m are as defined.

In a particularly preferred group of the compounds of formula I, $R^1$ to $R^5$ are hydrogen and G is hydrogen, an alkali or alkaline earth metal, m is 1, Q is group selected from

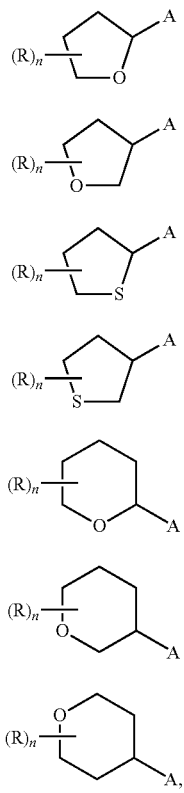

wherein n is 0 and A designates the point of attachment to the —$(CR^4R^5)_m$ moiety, or Q is pyridyl, and Het is a group of the formula

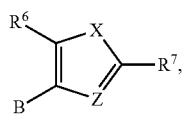

wherein X is S, Z is N, $R^6$ is methyl or ethyl, $R^7$ is phenyl substituted by halogen, and B designates the point of attachment to the ketoenol moiety, or Het is a group of the formula

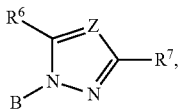

wherein Z is CH or C—$CH_3$, $R^6$ is methyl or ethyl, $R^7$ is phenyl substituted by halogen, and B designates the point of attachment to the ketoenol moiety.

Even more preferably, Q is a group of the formula $Q^7$ or pyridine-2-yl, and Het is a group of the formula $Het_2$ or $Het_{10}$, wherein $R^7$ is 4-chlorophenyl.

In an alternative suitable embodiment, Het is a group of formula $Het_{13}$:

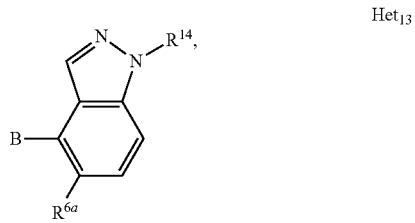

wherein:

B designates the point of attachment to the ketoenol moiety;

$R^{6a}$ is halogen, $C_1$-$C_2$alkyl, $C_1$-$C_2$fluoroalkyl, vinyl, ethynyl, or methoxy; preferably methyl or ethyl; and $R^{14}$ is hydrogen or $C_1$-$C_4$alkyl.

Preferably, the compound of formula I is one of compounds A1 to A25 as shown below, or an agriculturally or agronomically acceptable salt thereof (e.g. agriculturally acceptable metal or ammonium salt, e.g. an alkali metal or alkaline earth metal salt thereof):

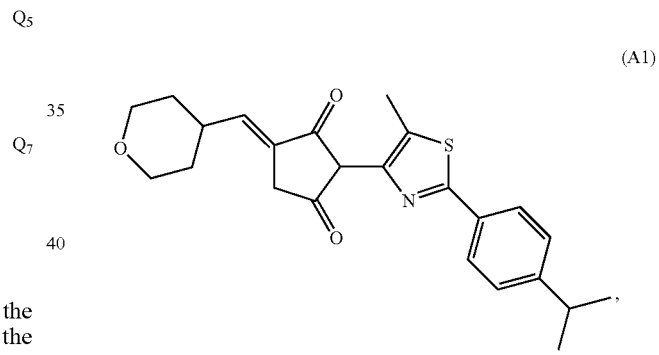

(A1)

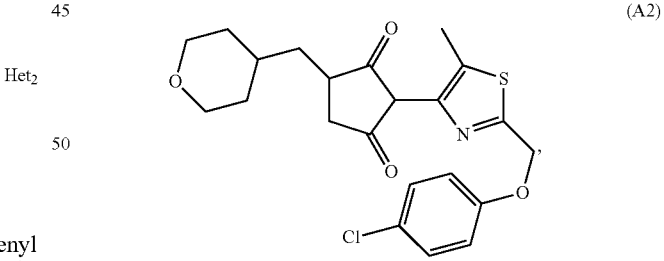

(A2)

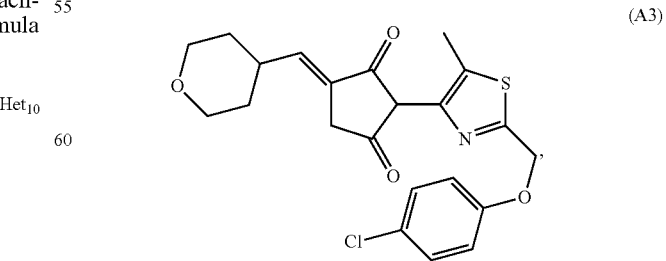

(A3)

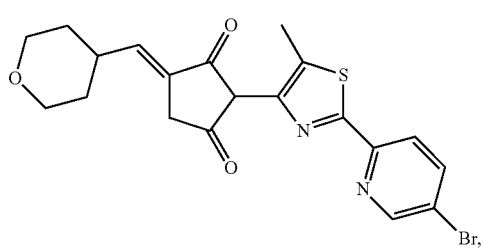
(A4)
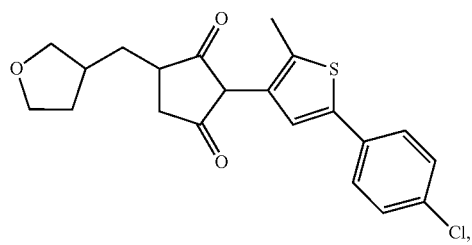
(A5)
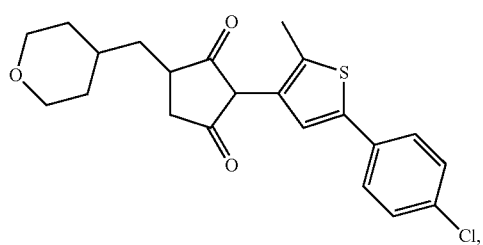
(A6)
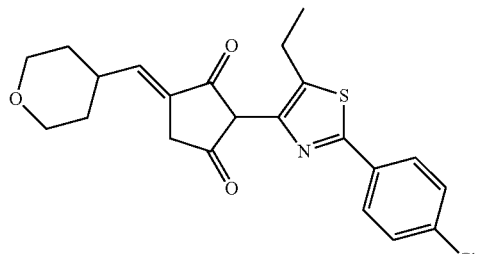
(A7)
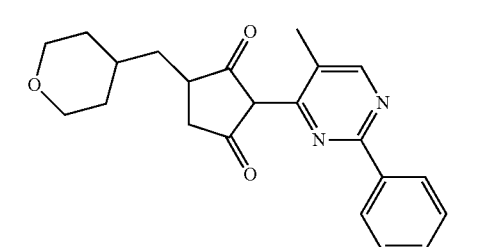
(A8)
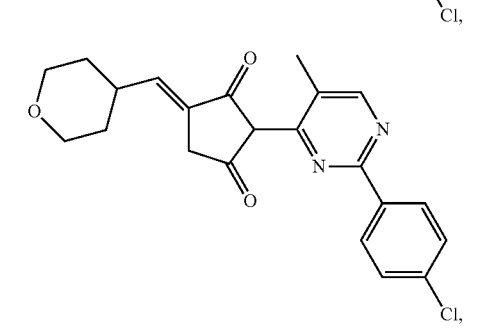
(A9)
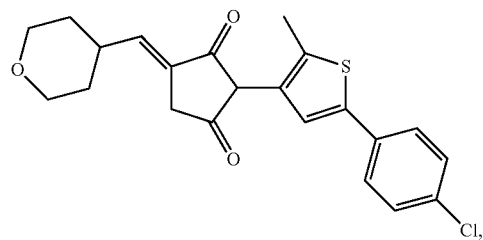
(A10)
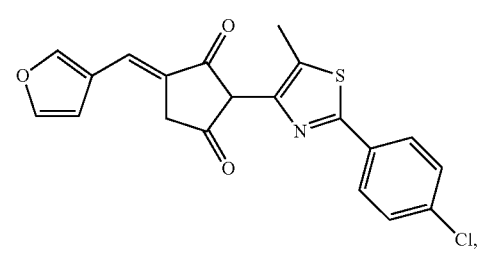
(A11)
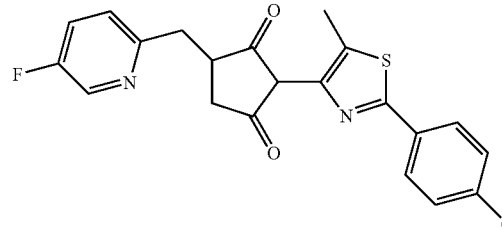
(A12)
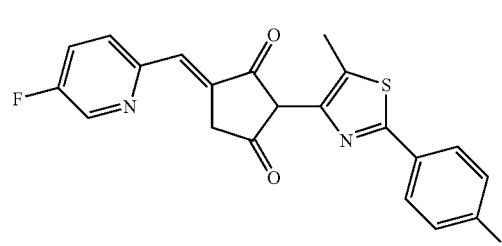
(A13)
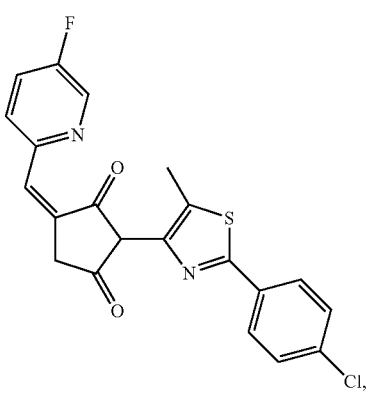
(A14)

(A15)
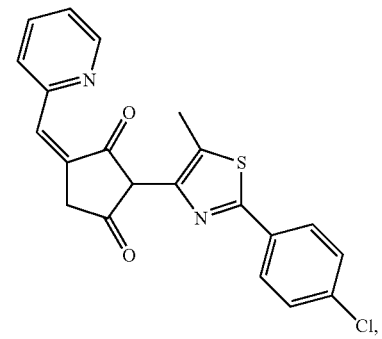

(A16)
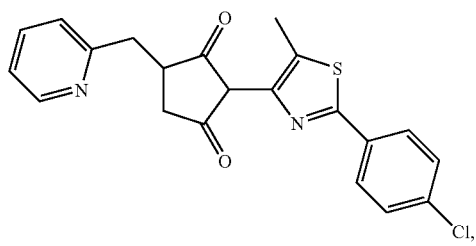

(A17)
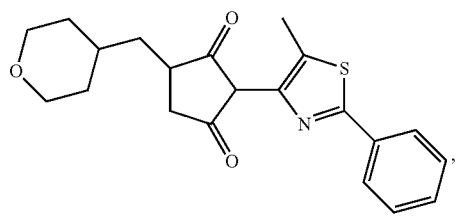

(A18)
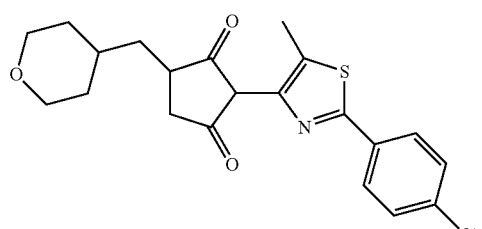

(A19)
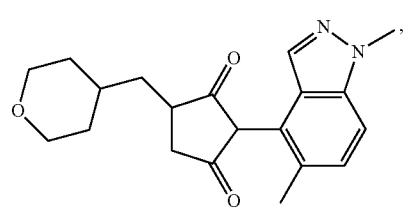

(A20)
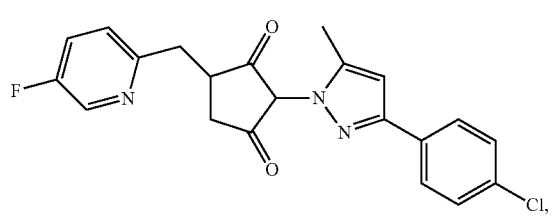

(A21)
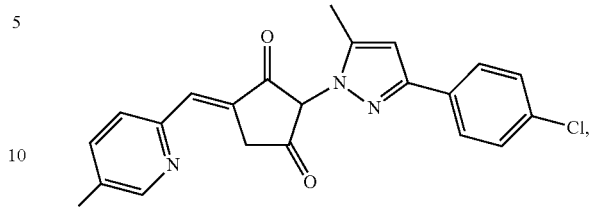

(A22)
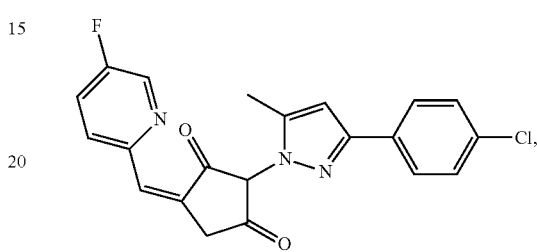

(A23)
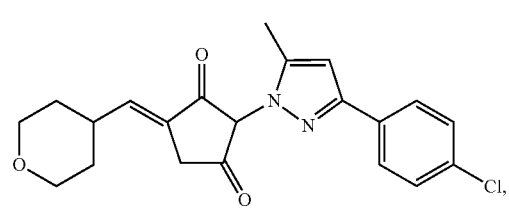

(A24)
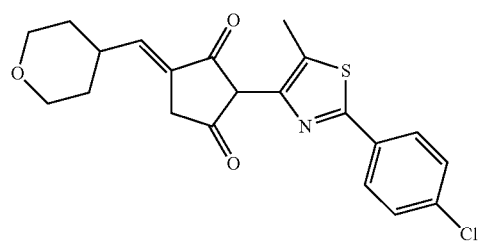

(A25)
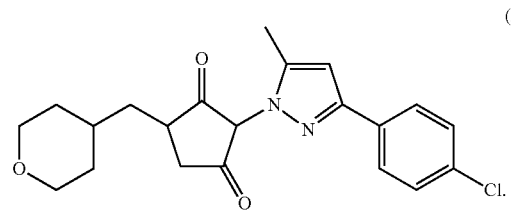

More preferably, the compound of formula I is one of compounds A7, A12, A16, A17, A18, A20, A23, A24 or A25 as shown above, or an agriculturally or agronomically acceptable salt thereof (e.g. agriculturally acceptable metal or ammonium salt, e.g. an alkali metal or alkaline earth metal salt thereof).

Certain compounds of formula (I) are alkenes, and as such undergo further reactions typical of alkenes to give additional compounds of formula (I) according to known procedures. Example of such reaction include, but are not restricted to, halogenation or hydrogenation

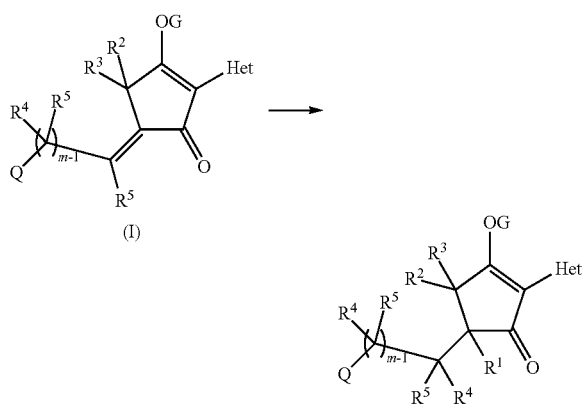

wherein $R^1$ and $R^4$ form a bond

Compounds of formula (I) wherein $R^1$ and $R^4$ form a bond and $R^5$ is halogen (preferably chloride or bromide) or $R^5$ is $C_1$-$C_6$alkylsulfonate (preferably mesylate) or $C_1$-$C_6$haloalkylsulfonate (preferably triflate) or an arylsulfonate (preferable tosylate) may undergo a cross-coupling reaction with a suitable coupling partner under conditions described in the literature for Suzuki-Miyaura, Sonogashira and related cross-coupling reactions to give additional compounds of formula (I) (see, for example, O'Brien, C. J. and Organ, M. G. Angew. Chem. Int. Ed. (2007), 46, 2768-2813; Suzuki, A. Journal of Organometallic Chemistry (2002), 653, 83; Miyaura N. and Suzuki, A. Chem. Rev. (1995), 95, 2457-2483).

Those skilled in the art will appreciate that compounds of formula (I) may contain an heteroaromatic moiety bearing one or more substituents capable of being transformed into alternative substituents under known conditions, and that these compounds may themselves serve as intermediates in the preparation of additional compounds of formula (I).

Additional compounds of formula (I) may be prepared by selectively reducing compounds of formula (I) where Q is a Heteroaromatic ring preferably furan or pyrrole in the presence of a suitable catalyst, and in a suitable solvent.

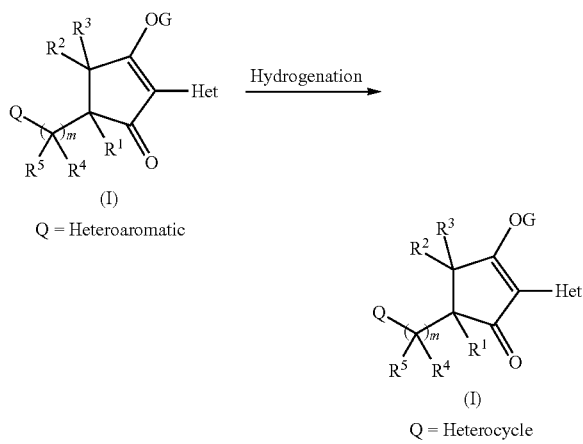

For example, compounds of formula (I) wherein $R^6$, $R^7$, $R^8$ or $R^{10}$ is alkenyl or alkynyl, may be reduced to compounds of formula (I) wherein $R^6$, $R^7$, $R^8$ or $R^{10}$ is alkyl under known conditions and compounds of formula (I) wherein $R^7$ is halogen, preferably bromide or iodine, may undergo a cross-coupling reaction with a suitable coupling partner under conditions described in the literature for Suzuki-Miyaura, Sonogashira and related cross-coupling reactions to give additional compounds of formula (I) (see, for example, O'Brien, C. J. and Organ, M. G. Angew. Chem. Int. Ed. (2007), 46, 2768-2813; Suzuki, A. Journal of Organometallic Chemistry (2002), 653, 83; Miyaura N. and Suzuki, A. Chem. Rev. (1995), 95, 2457-2483).

Compounds of formula (I) wherein G is $C_1$-$C_8$alkyl, $C_2$-$C_3$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), $C_3$-$C_8$ alkenyl, $C_3$-$C_8$haloalkenyl, $C_3$-$C_8$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating compounds of formula (A), which are compounds of formula (I) wherein G is H, with a reagent G-Z, wherein G-Z is alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$alkyl sulfonate, or a di-$C_1$-$C_8$alkyl sulfate, or with a $C_3$-$C_8$alkenyl halide, or with a $C_3$-$C_8$alkynyl halide, or with an acylating agent such as a carboxylic acid, HO—$C(X^a)R^a$, wherein $X^a$ is oxygen, an acid chloride, Cl—$C(X^a)R^a$, wherein $X^a$ is oxygen, or acid anhydride, [$R^aC(X^a)$]$_2$O, wherein $X^a$ is oxygen, or an isocyanate, $R^cN$=$C$=$O$, or a carbamoyl chloride, Cl—$C(X^d)$—$N(R^c)$—$R^d$ (wherein $X^d$ is oxygen and with the proviso that neither $R^c$ or $R^d$ is hydrogen), or a thiocarbamoyl chloride Cl—$C(X^d)$—$N(R^c)$—$R^d$ (wherein $X^d$ is sulfur and with the proviso that neither $R^c$ nor $R^d$ is hydrogen) or a chloroformate, Cl—$C(X^b)$—$X^c$—$R^b$, (wherein $X^b$ and $X^c$ are oxygen), or a chlorothioformate Cl—$C(X^b)$—$X^c$—$R^b$ (wherein $X^b$ is oxygen and $X^c$ is sulfur), or a chlorodithioformate Cl—$C(X^b)$—$X^c$—$R^b$, (wherein $X^b$ and $X^c$ are sulfur), or an isothiocyanate, $R^cN$=$C$=$S$, or by sequential treatment with carbon disulfide and an alkylating agent, or with a phosphorylating agent such as a phosphoryl chloride, Cl—$P(X^e)(R^f)$—$R^g$ or with a sulfonylating agent such as a sulfonyl chloride Cl—$SO_2$—$R^e$, preferably in the presence of at least one equivalent of base.

Isomeric compounds of formula (I) may be formed. For example, compounds of formula (A) may give rise to two isomeric compounds of formula (I), or to isomeric mixtures of compounds of formula (I). This invention covers both isomeric compounds of formula (I), together with mixtures of these compounds in any ratio.

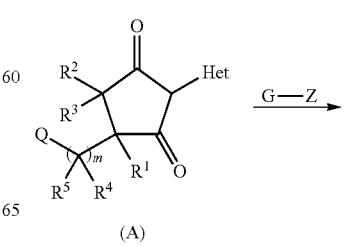

(A)

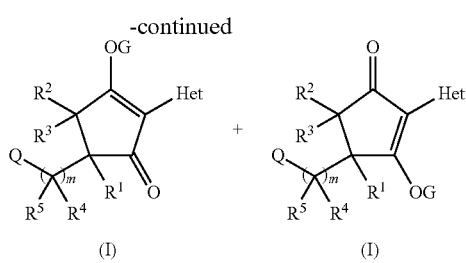

(I)

The O-alkylation of cyclic 1,3-diones is known; suitable methods are described, for example, in U.S. Pat. No. 4,436,666. Alternative procedures have been reported by Pizzorno, M. T. and Albonico, S. M. Chem. Ind. (London) (1972), 425; Born, H. et al. J. Chem. Soc. (1953), 1779; Constantino, M. G. et al. Synth. Commun. (1992), 22 (19), 2859; Tian, Y. et al. Synth. Commun. (1997), 27 (9), 1577; Chandra Roy, S. et al., Chem. Lett. (2006), 35 (1), 16; Zubaidha, P. K. et al. Tetrahedron Lett. (2004), 45, 7187 and by Zwanenburg, B. et al., Tetrahedron (2005), 45 (22), 7109.

The acylation of cyclic 1,3-diones may be effected by procedures similar to those described, for example, in U.S. Pat. Nos. 4,551,547, 4,175,135, 4,422,870, 4,659,372 and 4,436,666. Typically diones of formula (A) may be treated with the acylating agent in the presence of at least one equivalent of a suitable base, optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally a base such as triethylamine or pyridine in a suitable solvent such as tetrahydrofuran, dichloromethane or acetonitrile. Suitable procedures are described, for example, by Zhang, W. and Pugh, G. Tetrahedron Lett. (1999), 40 (43), 7595 and Isobe, T. and Ishikawa, T. J. Org. Chem. (1999), 64 (19) 6984.

Phosphorylation of cyclic-1,3-diones may be effected using a phosphoryl halide or thiophosphoryl halide and a base by procedures analogous to those described in U.S. Pat. No. 4,409,153.

Sulfonylation of compounds of formula (A) may be achieved using an alkyl or aryl sulfonyl halide, preferably in the presence of at least one equivalent of base, for example by the procedure of Kowalski, C. J. and Fields, K. W. J. Org. Chem. (1981), 46, 197.

Compounds of formula (A) may be prepared from a compounds of formula (I) by hydrolysis, preferably in the presence of an acid catalyst such as hydrochloric acid and optionally in the presence of a suitable solvent such as tetrahydrofuran or acetone preferably between 25° C. and 150° C. under conventional heating or under microwave irradiation.

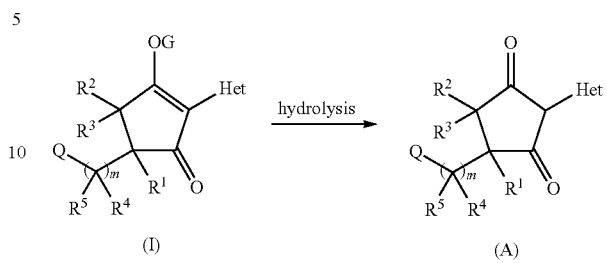

In a further approach, compounds of formula (A) may be prepared by the cyclisation of a compound of formula (B) or a compound of formula (C), wherein R'" is hydrogen or an alkyl group, preferably in the presence of an acid or base, and optionally in the presence of a suitable solvent, by analogous methods to those described by T. N. Wheeler, U.S. Pat. No. 4,209,532. Compounds of formula (B) or compounds of formula (C) wherein R'" is hydrogen may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

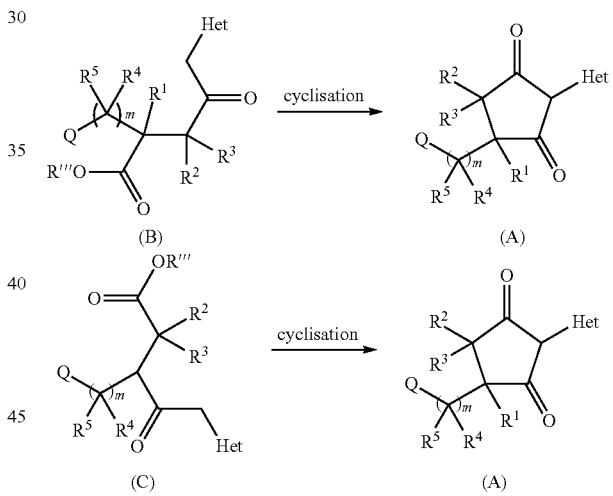

Compounds of formula (B) or compounds of formula (C) wherein R'" is alkyl (preferably methyl or ethyl), may be cyclised under acidic or basic conditions, preferably in the presence of at least one equivalent of a strong base such as potassium tert-butoxide, lithium diisopropylamide or sodium hydride and in a solvent such as tetrahydrofuran, toluene, dimethylsulfoxide or N,N-dimethylformamide.

Compounds of formula (B) and compounds of formula (C), wherein R'" is H, may be esterified to, respectively, compounds of formula (B) and compounds of formula (C), wherein R'" is alkyl, under standard conditions, for example by heating with an alkyl alcohol, ROH, in the presence of an acid catalyst.

Compounds of formula (B) and compounds of formula (C), wherein R'" is H, may be prepared, respectively, by saponification of a compounds of formula (D) and compounds of formula (E) wherein R'''' is alkyl (preferably methyl or ethyl), under standard conditions, followed by acidification of the

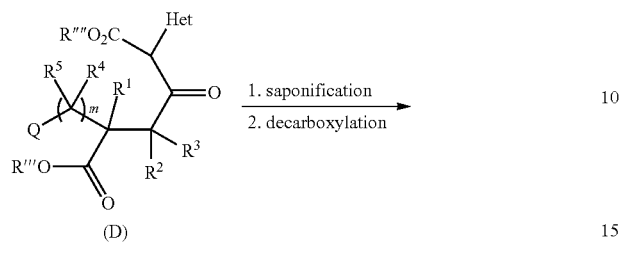

(D)

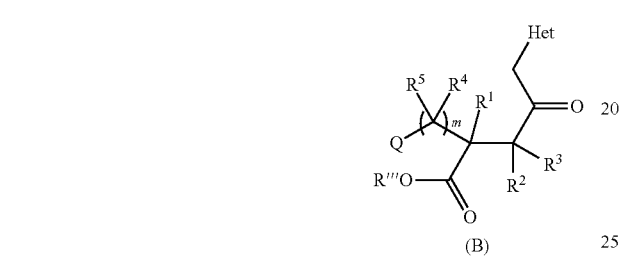

(E)

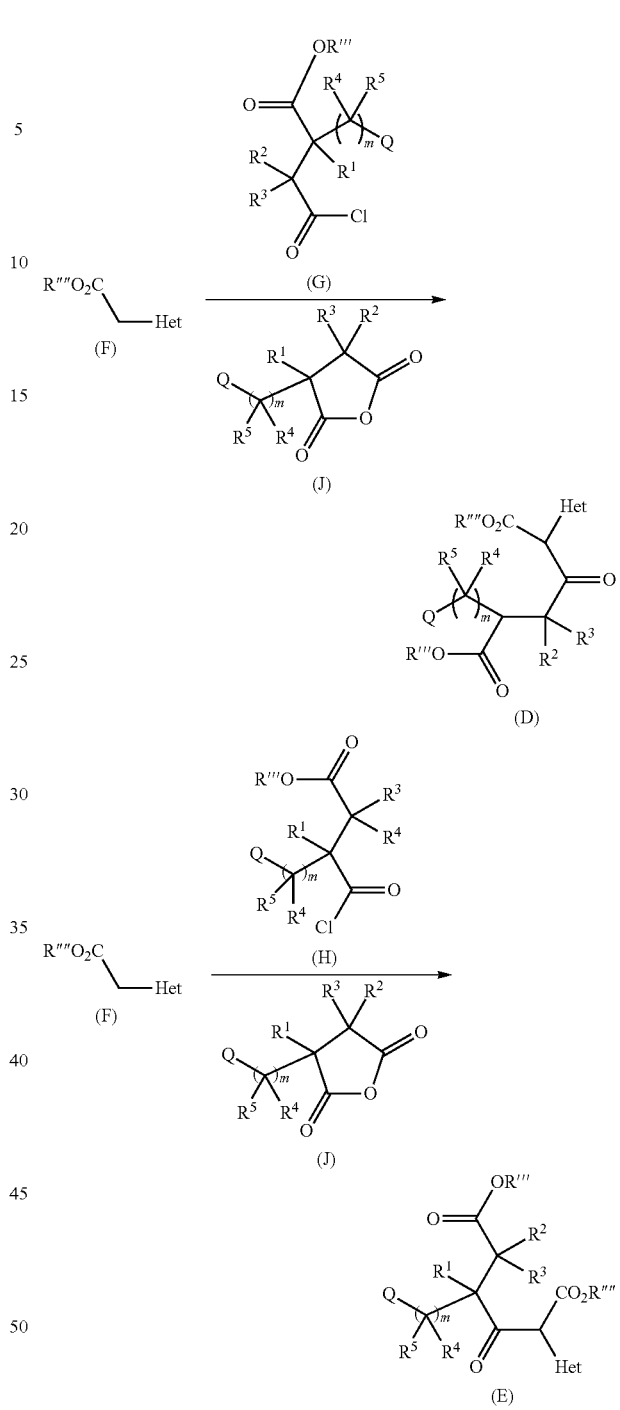

Compounds of formula (D) and compounds of formula (E), wherein R"" is alkyl, may be prepared by treating, respectively, compounds of formula (F) with suitable carboxylic acid chlorides of formula (G) or suitable carboxylic acid chlorides of formula (H) under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between −80° C. and 30° C. Alternatively, compounds of formula (D) and compounds of formula (E), wherein R"" is H, may be prepared by treating a compound of formula (F) with a suitable base (such as potassium tert-butoxide, sodium bis(trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of formula (J):

Compounds of formula (F) are known compounds, or may be prepared from known compounds by known methods.

Compounds of formula (J) may be prepared, for example, by analogous methods to those described by Ballini, R. et al. Synthesis (2002), (5), 681-685; Bergmeier, S. C. and Ismail, K. A. Synthesis (2000), (10), 1369-1371; Groutas, W. C. et al. J. Med. Chem. (1989), 32 (7), 1607-11 and Bernhard, K. and Lincke, H. Helv. Chim. Acta (1946), 29, 1457-1466.

Compounds of formula (G) or compounds of formula (H) may be prepared from a compound of formula (J) by treatment with an alkyl alcohol, R'"—OH, in the presence of a base, such as dimethylaminopyridine or an alkaline metal alkoxide (see, for example, Buser, S, and Vasella, A. Helv.

Chim. Acta, (2005), 88, 3151 and M. Hart et al. Bioorg. Med. Chem. Letters, (2004), 14, 1969), followed by treatment of the resulting acid with a chlorinating reagent such as oxalyl chloride or thionyl chloride under known conditions (see, for example, Santelli-Rouvier. C. Tetrahedron Lett. (1984), 25 (39), 4371; Walba D. and Wand, M. Tetrahedron Lett. (1982), 23 (48), 4995; Cason, J. Org. Synth. Coll. Vol. III, (169), 1955).

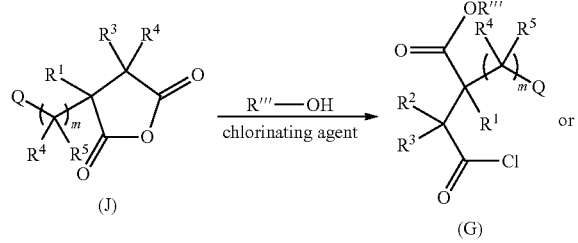

Compounds of formula (G) and compounds of formula (H) may be made from known compounds by known methods. For example, analogous methods to obtain compounds of formula (G) and compounds of formula (H) are described by Bergmeier, S. C. and Ismail, K. A. Synthesis (2000), (10), 1369-1371.

In an further approach to compounds of formula (I) may be prepared by treating compounds of formula (K) with compounds of formula (L) wherein LG is a leaving group such as halogen (preferably iodide, bromide or chloride) or an activated alcohol (preferably mesylate or tosylate) under basic conditions. Suitable bases include lithium diisopropylamide, sodium hexamethyldisilazide, potassium tert-butoxide and the reaction is preferably conducted in a suitable solvent (such as tetrahydrofuran) at a temperature between −80° C. and 30° C.

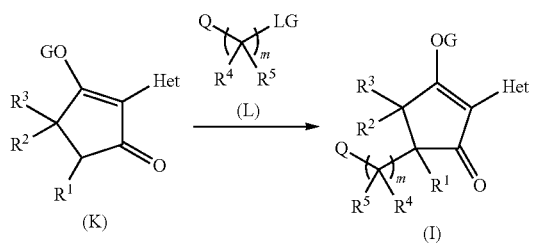

Compounds of formula (L) are known, or may be made known compounds by known methods (see for example: WO2006016178; Ueno, H. et al. J. Med. Chem. (2005), 48(10), 3586-3604; Kanoh, S. et al. Tetrahedron (2002), 58(35), 7049-7064; Strachan, J.-P. et al, J. Org. Chem. (2006), 71(26), 9909-9911).

Compounds of formula (K) are known compounds or may be made from known compounds by known methods (see, for example, Song, Y. S. S. et al. Tetrahedron Lett. (2005), 46 (46), 5987-5990 and WO09030450)

Alternatively, compounds of formula (K) wherein G is $C_1$-$C_6$alkyl may be prepared by alkylation of compounds of formula (K), wherein G is hydrogen under known conditions. Compounds of formula (K), wherein G is hydrogen, are known, or may be prepared from known compounds by known methods (see, for example, DE10118310).

Alternatively, in a further approach to compounds of formula (K), compounds of formula (M), which are compounds of formula (K) wherein G is hydrogen and Het is ($Het_2$) when $R^6$ is $CH_2R''''$ and $R''''$ is hydrogen or methyl, may be prepared by thermal rearrangement of compounds of formula (AN), optionally in the presence of a suitable solvent and optionally under microwave irradiation.

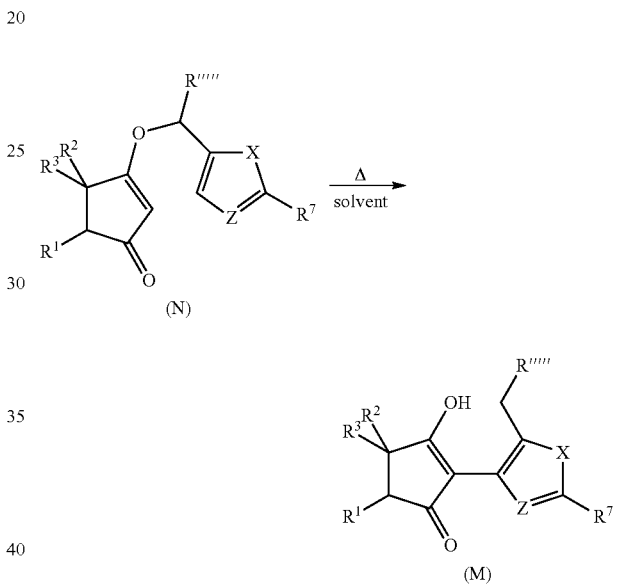

Preferably, the rearrangement is effected by heating compounds of formula (AN) at temperatures of between 120-300° C., optionally in a suitable solvent such as 1,2-dimethoxyethane, diethylene glycol methyl ether, triglyme, tetraglyme, xylene, mesitylene or Dowtherm®, and optionally under microwave irradiation.

Similarly, compounds of formula (O), which are compounds of formula (K) wherein G is hydrogen and Het is ($Het_3$) when $R^6$ is $CH_2R''''$ and $R''''$ is hydrogen or methyl, may be prepared from compounds of formula (P) using similar methods.

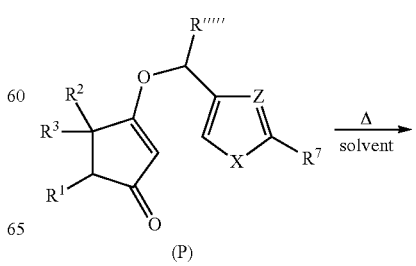

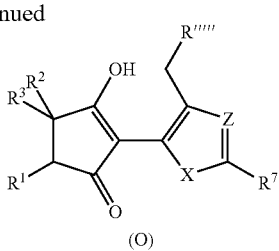

(O)

Compounds of formula (N) may be prepared from compounds of formula (Q) by alkylation with compounds of formula (R), wherein L is a suitable leaving group such as a halogen or an alkyl- or aryl-sulfonate, optionally in the presence of a suitable base and optionally in a suitable solvent as described above for the alkylation of compounds of formula (A)

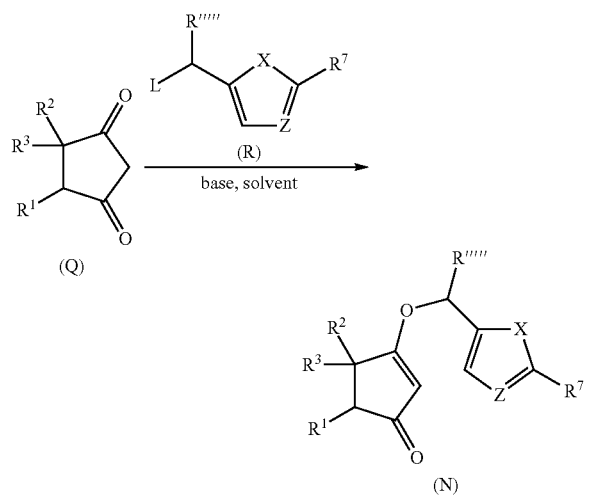

Similarly, compounds of formula (P) may be prepared from compounds of formula (Q) by alkylation with compounds of formula (S), wherein L is a suitable leaving group such as a halogen or an alkyl- or aryl-sulfonate, under similar conditions.

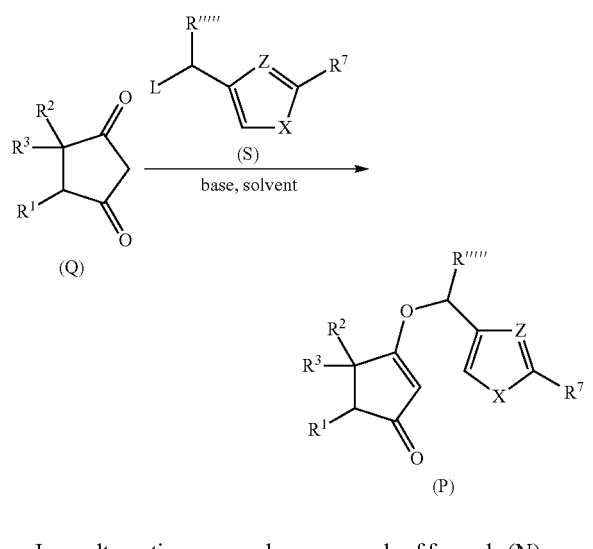

In an alternative approach, compounds of formula (N) may be prepared from compounds of formula (Q) by condensation with alcohols of formula (T), optionally in the presence of a suitable acid catalyst such as p-toluenesulfonic acid, or a Lewis acid catalyst, for example, ytterbium (III) trifluoromethanesulfonate, lanthanum (III) trifluoromethanesulfonate, sodium tetrachloroaurate (III) dihydrate, titanium (IV) chloride, indium (III) chloride or aluminium chloride, and optionally in a suitable solvent. Suitable solvents are selected to be compatible with the reagents used, and include, for example, toluene, ethanol or acetonitrile. Similar approaches have been described by, for example, M. Curini; F. Epifano, S. Genovese, Tetrahedron Lett. (2006), 47, 4697-700; A. Arcadi, G. Bianchi, S. Di Giuseppe, F. Marinelli, Green Chemistry (2003), 5, 64-7.

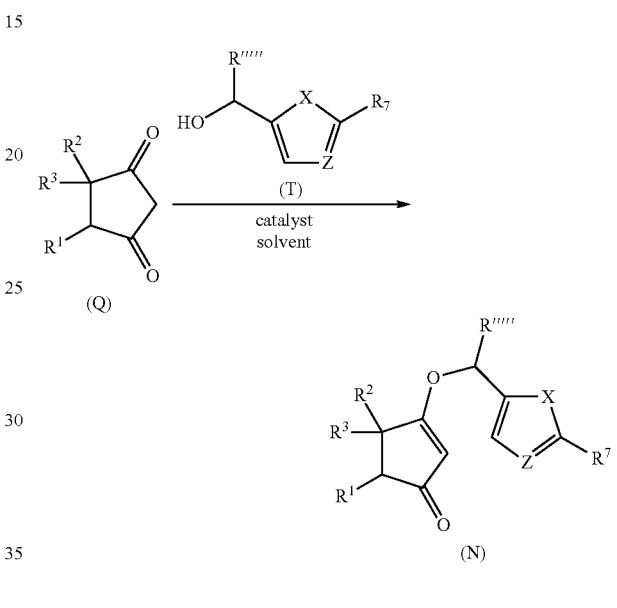

Alternatively, the condensation may be effected in the presence of suitable coupling agents such as 2-chloro-1-methylpyridinium iodide, N,N'-dicyclohexylcarbodiimide, 1,(3-dimethylaminopropyl)-3-ethylcarbodiimimde and N,N-carbodiimidazole and a suitable base such a triethylamine or pyridine in a suitable solvent such as tetrahydrofuran, acetonitrile or dichloromethane, or in the presence of a triarylphosphine (such as triphenylphosphine) and a dialkyl azidodicarboxylate (preferably diethyl azidodicarboxylate or diisopropyl azidodicarboxylate) and in a suitable solvent such as diethyl ether, tetrahydrofuran or 1,4-dioxane as described, for example, by O. Mitsunobu, Synthesis (1981), 1, 1-28.

Using similar processes, compounds of formula (P) may be prepared by reaction of compounds of formula (Q) with compounds of formula (U).

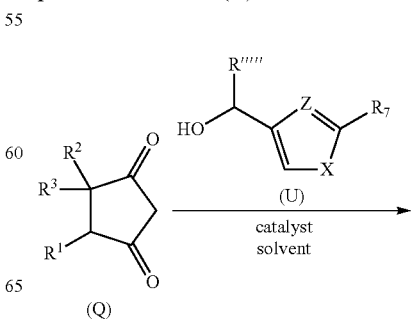

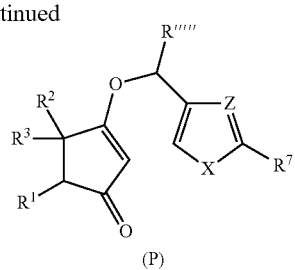

(P)

Additional compounds of formula (N) wherein R' is an aromatic or heteroaromatic moiety, or is an alkyl, alkenyl or alkynyl group, may be prepared by the reaction of compounds of formula (V), wherein A is an atom or group suitable for undergoing cross-coupling reactions (for example A is chlorine, bromine or iodine, or a haloalkylsulfonate such as trifluoromethanesulfonate), and R'''' is as defined for compound of formula (O), with a suitable coupling partner under conditions described in the literature for Suzuki-Miyaura, Sonogashira, Stille and related cross-coupling reactions.

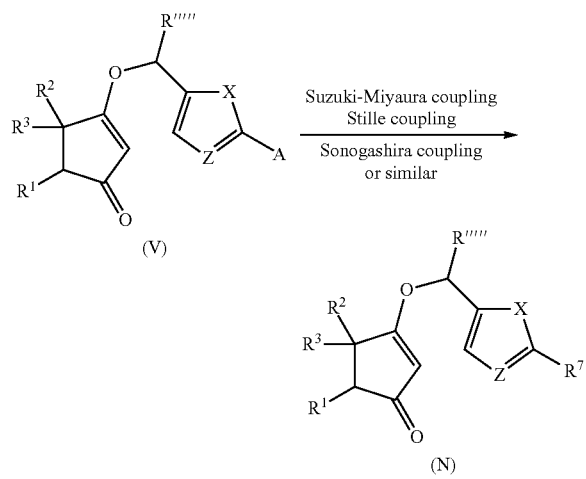

For example, compounds of formula (V) may be treated with aryl-, heteroaryl-, alkyl-, alkenyl- or alkynylboronic acids, $R^7$—$B(OH)_2$, boronate esters, $R^7$—$B(OR''''')_2$, wherein R''''' is $C_1$-$C_6$alkyl or $R^7$—$B(OR''''')_2$ represents cyclic boronate esters derived from a $C_1$-$C_6$diol (especially preferred are cyclic boronate esters derived from pinacol), or a metal (especially potassium) aryl-, heteroaryl, alkyl-, alkenyl- and alkynyltrifluoroborate salts, $M^+[R^7—BF_3]^-$ in the presence of a suitable palladium catalyst, a suitable ligand and a suitable base in the presence of a suitable solvent, under Suzuki-Miyaura conditions (see, for example K. Billingsley and S. Buchwald, J. Am. Chem. Soc. (2007), 129, 3358-3366; H. Stefani, R. Cella and A. Vieira, Tetrahedron (2007), 63, 3623-3658; N. Kudo, M. Perseghini and G. Fu, Angew. Chem. Int. Ed. (2006), 45, 1282-1284; A. Roglans, A. Pia-Quintana and M. Moreno-Mañas, Chem. Rev. (2006), 106, 4622-4643; J-H Li, Q-M Zhu and Y-X Xie, Tetrahedron (2006), 10888-10895; S. Nolan et al., J. Org. Chem. (2006), 71, 685-692; M. Lysén and K. Köhler, Synthesis (2006), 4, 692-698; K. Anderson and S. Buchwald, Angew. Chem. Int. Ed. (2005), 44, 6173-6177; Y. Wang and D. Sauer, Org. Lett. (2004), 6 (16), 2793-2796; I. Kondolff, H. Doucet and M, Santelli, Tetrahedron, (2004), 60, 3813-3818; F. Bellina, A. Carpita and R. Rossi, Synthesis (2004), 15, 2419-2440; H. Stefani, G. Molander, C-S Yun, M. Ribagorda and B. Biolatto, J. Org. Chem. (2003), 68, 5534-5539; A. Suzuki, Journal of Organometallic Chemistry (2002), 653, 83; G. Molander and C-S Yun, Tetrahedron (2002), 58, 1465-1470; G. Zou, Y. K. Reddy and J. Falck, Tetrahedron Lett. (2001), 42, 4213-7215; S. Darses, G. Michaud and J-P, Genêt, Eur. J. Org. Chem. (1999), 1877-1883).

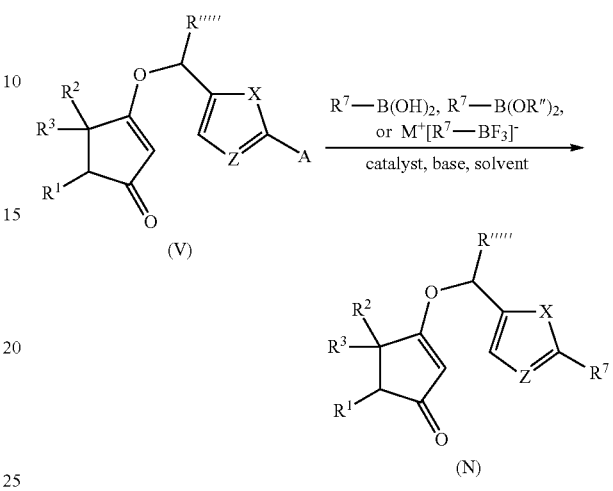

Alternatively, compounds of formula (N), wherein $R^7$ is an optionally substituted acetylene, may be prepared from compounds of formula (V) by reacting with a terminal alkyne, $R^7$—H, in the presence of a suitable palladium catalyst and optionally in the presence of a suitable copper co-catalyst, a suitable ligand, a suitable base and a suitable additive under conditions known to effect the Sonogashira coupling (see, for example, U. Sorenson and E Pombo-Villar, Tetrahedron (2005), 2697-2703; N. Leadbeater and B. Tominack, Tetrahedron Lett. (2003), 44, 8653-8656; K. Sonogashira, J. Organomet. Chem. (2002), 653, 46-49).

In a further approach, compounds of formula (N), wherein $R^7$ is alkyl, optionally substituted vinyl, optionally substituted ethynyl, optionally substituted aryl or optionally substituted heteroaryl, may be prepared from compounds of formula (V) by reaction with a suitable orgunnostannane under Stille conditions (see, for example, R. Bedford, C. Cazin and S. Hazlewood (2002), 22, 2608-2609; S. Ley et al., Chem. Commun. (2002), 10, 1134-1135; G. Grasa and S, Nolan, Org. Lett. (2001), 3 (1), 119-122; T. Weskamp, V. Boehm, J. Organomet. Chem. (1999), 585 (2), 348-352; A. Littke and G. Fu, Angew. Chem. Int. Ed. (1999), 38 (16), 2411-2413; J. Stille et al., Org. Synth. (1992), 71, 97).

Compounds of formula (P) may be prepared from compounds of formula (W), wherein A and R''''' are as defined for compounds of formula (V), by analogous methods using appropriate starting materials.

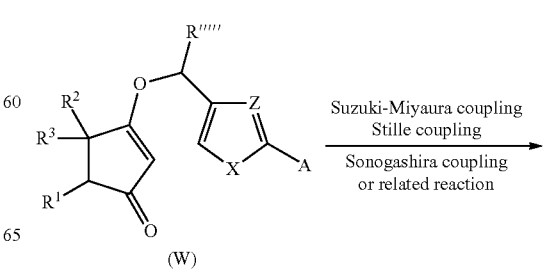

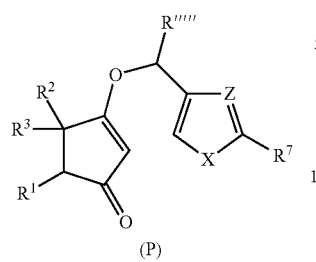

(P)

Compounds of formula (V) may be prepared from compounds of formula (Q), by reaction with compounds of formula (Z) wherein L is a suitable leaving group such as a halogen or an alkyl- or aryl-sulfonate, by processes analogous to those described above for the preparation of compounds of formula (N) from compounds of formula (Q). Alternatively, compounds of formula (V) may be prepared by reaction of compounds of formula (Q) with compounds of formula (AA) by processes analogous to those described above for the preparation of compounds of formula (N) from compounds of formula (Q).

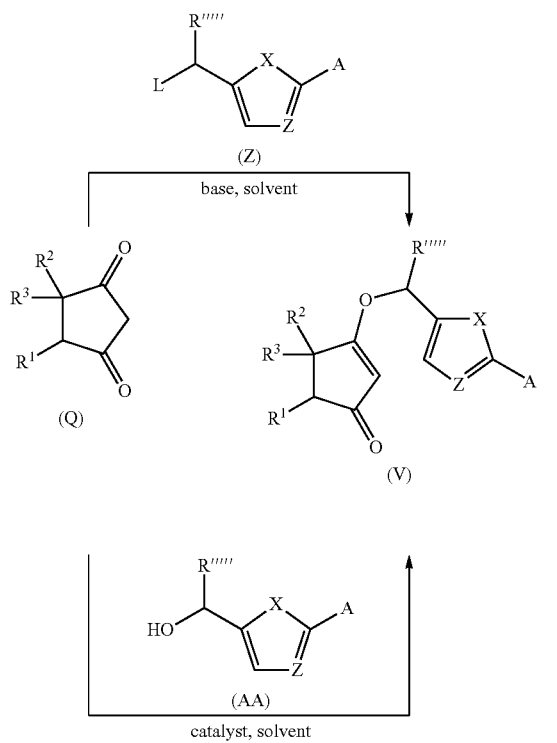

Compounds of formula (W) may be prepared from compounds of formula (Q), by reaction with compounds of formula (AB) wherein L is a suitable leaving group such as a halogen or an alkyl- or aryl-sulfonate, by processes analogous to those described above for the preparation of compounds of formula (N) from compounds of formula (Q). Alternatively, compounds of formula (W) may be prepared by reaction of compounds of formula (Q) with compounds of formula (AB) by processes analogous to those described above for the preparation of compounds of formula (N) from compounds of formula (Q).

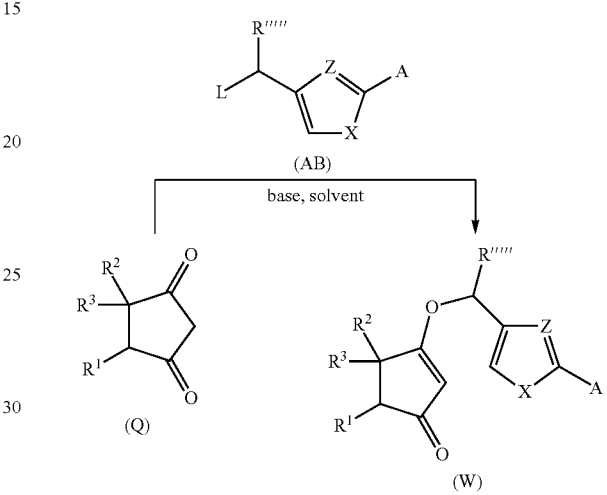

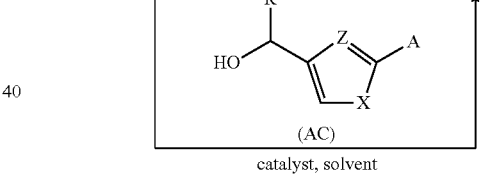

In an alternative approach, compounds of formula (Q) may be treated with a halogenating agent such as phosphorus oxychloride, phosphorus pentachloride, phosphorus pentabromide, phosphorus oxybromide, oxalyl chloride or oxalyl bromide, optionally in a suitable solvent such as toluene, chloroform, dichloromethane with optionally the presence of dimethylformamide, and the resulting vinyl halides of formula (AD), wherein Hal is chlorine or bromine may be converted by reaction with alcohols of formula (T), or of formula (U), or of formula (AA) or of formula (AC) optionally in the presence of a suitable base such as sodium hydride, sodium tert-butoxide, potassium tert-butoxide and a suitable solvent such as tetrahydrofuran, 1,4-dioxane, diethylene glycol dimethyl ether to give compounds of formula (N), formula (P), formula (V) and formula (W) respectively:

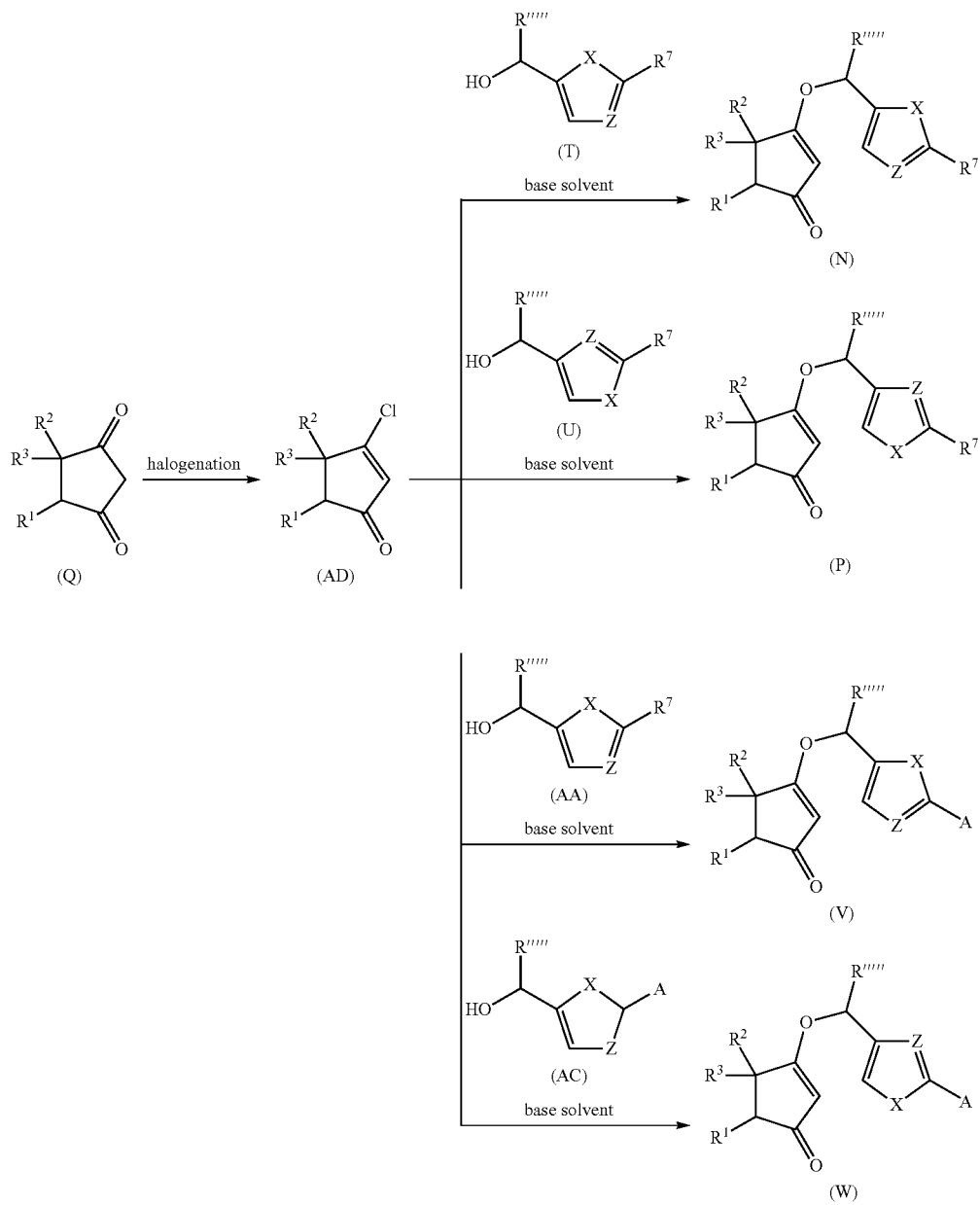

Compounds of formula (Q) are known compounds or may be made from known compounds by known methods.

Those skilled in the art will appreciate that compounds of formula (K) may contain a heteroaromatic moiety bearing one or more substituents capable of being transformed into alternative substituents under known conditions, and that these compounds may themselves serve as intermediates in the preparation of additional compounds of formula (K). For example, a heterocycle of formula (M) wherein $R^7$ is alkenyl or alkynyl, may be reduced to compounds of formula (M) wherein $R^7$ is alkyl under known conditions.

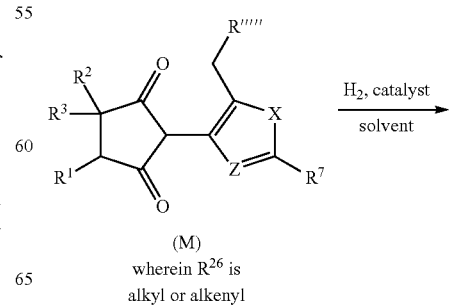

(M)
wherein $R^{26}$ is alkyl or alkenyl

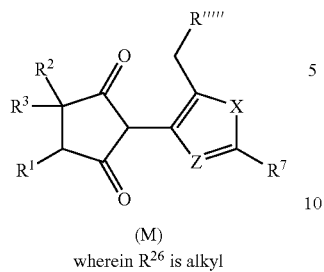

(M)
wherein $R^{26}$ is alkyl

In a further approach to compounds of formula (M), wherein Het is a group of formula (Het$_2$), X is S, and Z is N, compounds of formula (AE) wherein L is a suitable leaving group such as a halogen or an alkyl- or haloalkylsulfonate, may be treated with compounds of formula (AF) in the presence of a suitable base (such as triethylamine or pyridine), and optionally in a suitable solvent (such as water, acetone, ethanol or isopropanol) according to known procedures, (see, for example, E. Knott, J. Chem. Soc. (1945), 455; H. Brederick, R. Gompper, Chem. Ber. (1960), 93, 723; B. Friedman, M. Sparks and R. Adams, J. Am. Chem. Soc. (1937), 59, 2262).

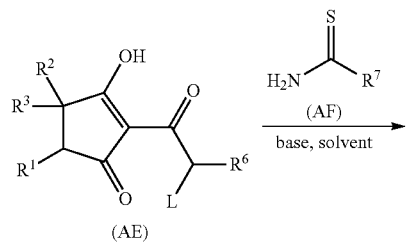

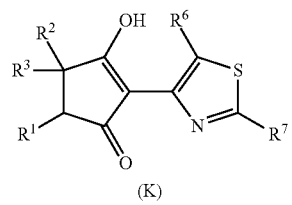

(K)
where G is H and
Het is Het$_2$
X is S and Z is N

Alternatively, compounds of formula (AE) may be treated with thiourea, by known procedures (see, for example, V. Pshenichniya, O. Gulyakevich and V. Kripach, Chemistry of Heterocyclic Compounds (1990), 10, 1409-1412), and the resulting products of formula (AG) may be converted into additional compounds of formula (K) by conversion to halides of formula (AH), wherein Hal is chlorine, bromine or iodine, under Sandmeyer conditions, and compounds of formula (AH) may be converted to compounds of formula (K) by cross-coupling under known conditions for the Suzuki-Miyaura, Sonogashira, Stille and related reactions, as described previously.

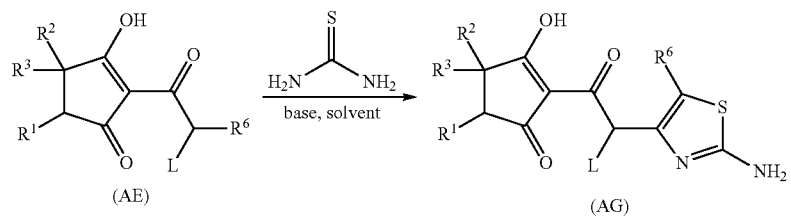

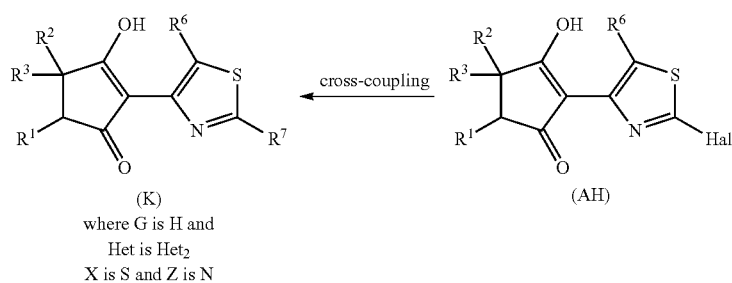

(K)
where G is H and
Het is Het$_2$
X is S and Z is N

Compounds of formula (AE) may be prepared from compounds of formula (Q) under known conditions (see, for example, V. Pshenichniya, O. Gulyakevich and V. Kripach, Chemistry of Heterocyclic Compounds (1990), 10, 1409-1412; V. Pshenichniya, O. Gulyakevich and V. Kripach, Russian Journal of Organic Chemistry (1989), 25 (9), 1882-1888).

Compounds of formula (R), formula (S), formula (T), formula (U), formula (Z), formula (AA), formula (AB) and formula (AC) are known or may be prepared by known methods from known compounds (see, for example T. T. Denton, X. Zhang, J. R. Cashman, J. Med. Chem. (2005), 48, 224-239; J. Reinhard, W. E. Hull, C.-W. von der Lieth, U. Eichhorn, H.-C. Kliem, J. Med. Chem. (2001), 44, 4050-4061; H. Kraus and H. Fiege, DE19547076; M. L. Boys, L. A. Schretzman, N. S. Chandrakumar, M. B. Tollefson, S. B. Mohler, V. L. Downs, T. D. Penning, M. A. Russell, J. A. Wendt, B. B. Chen, H. G. Stenmark, H. Wu, D. P. Spangler, M. Clare, B. N. Desai, I. K. Khanna, M. N. Nguyen, T. Duffin, V. W. Engleman, M. B. Finn, S. K. Freeman, M. L. Hanneke, J. L. Keene, J. A. Klover, G. A. Nickols, M. A. Nickols, C. N. Steininger, M. Westlin, W. Westlin, Y. X. Yu, Y. Wang, C. R. Dalton, S. A. Norring, Bioorg. Med. Chem. Lett. (2006), 16, 839-844; A. Silberg, A. Benko, G. Csavassy, Chem. Ber. (1964), 97, 1684-1687; K. Brown and R. Newbury, Tetrahedron Lett. (1969), 2797; A. Jansen and M. Szelke, J. Chem. Soc. (1961), 405; R. Diaz-Cortes, A. Silva and L. Maldonado, Tetrahedron Lett. (1997), 38(13), 2007-2210; M. Friedrich, A. Waechtler and A De Meijure, Synlett. (2002), 4, 619-621; F. Kerdesky and L. Seif, Synth. Commun. (1995), 25 (17), 2639-2645; Z. Zhao, G. Scarlato and R. Armstrong., Tetrahedron Lett. (1991), 32 (13), 1609-1612; K-T. Kang and S. Jong, Synth. Commun. (1995), 25 (17), 2647-2653; M. Altamura and E. Perrotta, J. Org. Chem. (1993), 58 (1), 272-274).

Alternatively, compounds of formula (I) where $R^1$ and $R^4$ from a bond can be prepared from compounds of formula (AJ) by known methods (see for example Nagaoka, H. et al. Tetrahedron Letters (1985), 26 (41), 5053-5056; Nagaoka, H. et al. J. Am. Chem. Soc. (1986), 108 (16), 5019-5021; Zuki, M. et al. Bull. Chem. Soc. Japan (1988), 61(4), 1299-1312; Enholm, E. J. et al. J. Org. Chem. (1996), 61 (16), 5384-5390; Clive, D. L. J. et al. Tetrahedron (2001), 57 (18), 3845-3858; Bartoli, G. et al. J. Org. Chem. (2002), 67 (25), 9111-9114. Jung, M. E. et al. Chem. Comm. (2003), (2), 196-197; EP1433772; JP2004203844; IN194295)

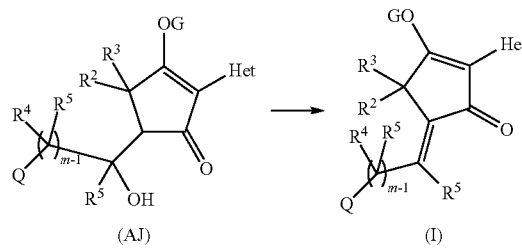

wherein $R^1$ and $R^4$ form a bond

Compounds of formula (AJ) may be prepared by treating compounds of formula (K) with compounds of formula (AK) under basic conditions. Suitable bases include lithium diisopropylamide, sodium hexamethyldisilazide, potassium tert-butoxide and the reaction is preferably conducted in a suitable solvent (such as tetrahydrofuran) at a temperature between −80° C. and 30° C.

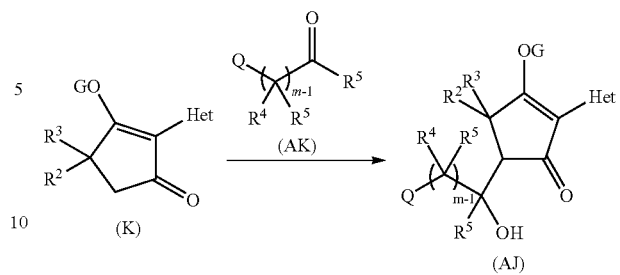

Compounds of formula (AK) are known, or may be made from known compounds by known methods.

Compounds of formula (I) (wherein G is $C_1$-$C_4$alkyl) may be prepared by reacting a compounds of formula (AL) (wherein G is $C_1$-$C_4$alkyl, and Hal is a halogen, preferably bromine or iodine), with heteroaryl boronic acids, Het-B $(OH)_2$ of formula (AM) or heteroaryl boronate esters in the presence of a suitable palladium catalyst (for example 0.001-50% palladium(II) acetate with respect to compound (AL)) and a base (for example 1 to 10 equivalents potassium phosphate with respect to compound (AL)) and preferably in the presence of a suitable ligand (for example 0.001-50% (2-dicyclohexylphosphino)-2',6'-dimethoxybiphenyl with respect to compound (AL)), and in a suitable solvent (for example toluene or 1,2-dimethoxyethane), preferably between 25° C. and 200° C. under conventional heating or under microwave irradiation (see, for example, Song, Y. S. S. et al. Tetrahedron Lett. (2005), 46 (46), 5987-5990).

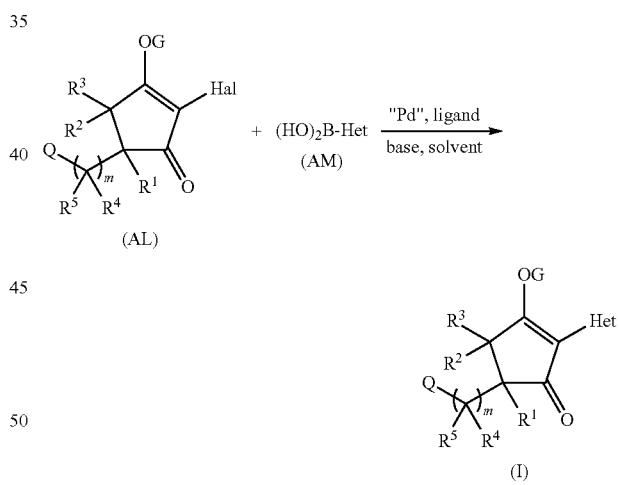

Preferred coupling partners include heteroarylboronic acids, ($P_1$) to ($P_8$), wherein $R^6$, $R^7$, $R^8$, $R^9$, $R^{10}$, $R^{11}$, X, $W^1$, $W^2$, $W^3$, $W^4$ w and Z are as defined above.

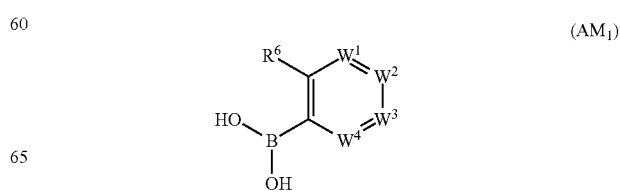

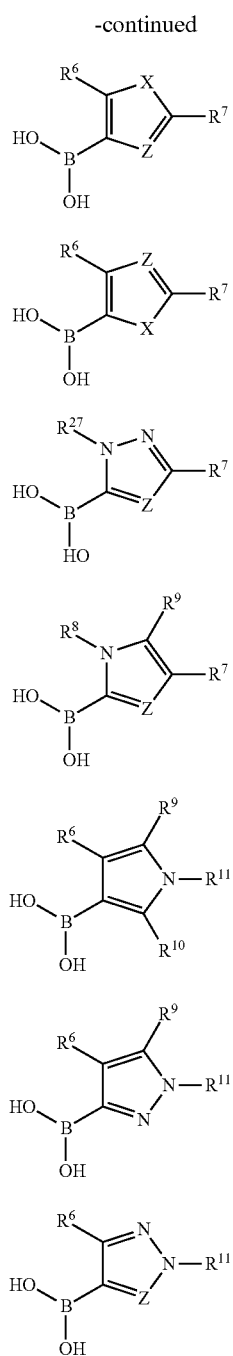

(AM₂)
(AM₃)
(AM₄)
(AM₅)
(AM₆)
(AM₇)
(AM₈)

Heteroarylboronic acids of formula (AM) are known compounds, or may be prepared from known compounds by known methods (see for example A. Voisin et al., Tetrahedron (2005), 1417-1421; A. Thompson et al, Tetrahedron (2005), 61, 5131-5135; K. Billingsley and S. Buchwald, J. Am. Chem. Soc. (2007), 129, 3358-3366; N. Kudo, M. Pauro and G. Fu, Angew. Chem. Int. Ed. (2006), 45, 1282-1284; A. Ivachtchenko et al., J. Heterocyclic Chem. (2004), 41(6), 931-939; H. Matondo et al., Synth. Commun. (2003), 33 (5) 795-800; A. Bouillon et al., Tetrahedron (2003), 59, 10043-10049; W. Li et al., J. Org. Chem. (2002), 67, 5394-5397; C. Enguehard et al., J. Org. Chem. (2000), 65, 6572-6575; H-N Nguyen, X. Huang and S. Buchwald, J. Am. Chem. Soc. (2003), 125, 11818-11819, and references therein).

Compounds of formula (AL) may be prepared by halogenating compounds of formula (AN), followed by alkylation of the resulting halide of formula (AO) with a $C_1$-$C_4$alkyl halide or tri-$C_1$-$C_4$alkylorthoformate under known conditions, for example by the procedures of Shepherd R. G. et al. J. Chem. Soc. Perkin Trans. 1 (1987), 2153-2155 and Lin Y.-L. et al. Bioorg. Med. Chem. (2002), 10, 685-690. Alternatively, compounds of formula (AL) may be prepared by alkylating a compound of formula (AN) with a $C_{1-4}$ alkyl halide or a tri-$C_{1-4}$-alkylorthoformate, and halogenating the resulting enone of formula (AP) under known conditions (see for example Song, Y. S. et al. Tetrahedron Lett. (2005), 46 (36), 5987-5990; Kuethe, J. T. et al., J. Org. Chem. (2002), 67(17), 5993-6000; Belmont, D. T. et al. J. Org. Chem. 1985, 50 (21), 4102-4107).

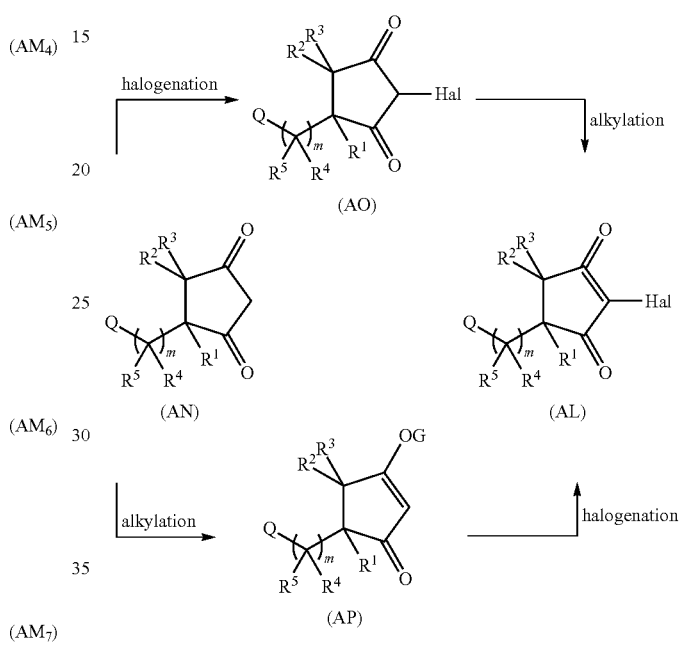

Compounds of formula (AP) may be prepared by treating compounds of formula (AQ) with compounds of formula (L) wherein LG is a leaving group such as halogen (preferably iodide or bromide) or an activated alcohol (preferably mesylate or tosylate) under basic conditions. Suitable bases include lithium diisopropylamide, sodium hexamethyldisilazide, potassium tert-butoxide and the reaction is preferably conducted in a suitable solvent (such as tetrahydrofuran) at a temperature between −80° C. and 30° C. (see, for example, Gulias, M. et al. Org. Lett. (2003), 5(11), 1975-1977; Altenbach, R. J. et al. J. Med. Chem. (2006), 49 (23), 6869-6887; Snowden, R. L. Tetrahedron (1986), 42 (12), 3277-90; Oppolzer, W. et al. Helv. Chim. Acta (1980), 63 (4), 788-92; Mellor, M. et al. Synth. Commun. 1979, 9 (1), 1-4).

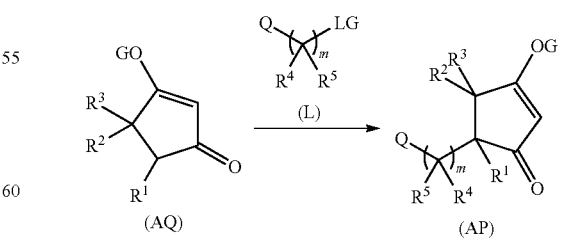

Compounds of formula (AQ) are known, or may be made from known compounds by known methods.

Alternatively compounds of formula (AP) where $R^1$ and $R^4$ from a bond can be prepared from compounds of formula (AR) by known methods (see, for example, Nagaoka, H. et al. Tetrahedron Letters (1985), 26 (41), 5053-5056; Nagaoka, H. et al., J. Am. Chem. Soc. (1986), 108 (16), 5019-5021; zuki, M. et al. Bull. Chem. Soc. Japan (1988), 61(4), 1299-1312; Enholm, E. J. et al. J. Org. Chem. (1996), 61 (16), 5384-5390; Clive, D. L. J. et al. Tetrahedron (2001), 57 (18), 3845-3858; Bartoli, G. et al. J. Org. Chem. (2002), 67 (25), 9111-9114. Jung, M. E. et al., Chem. Comm. (2003), (2), 196-197; EP1433772; JP2004203844; IN194295).

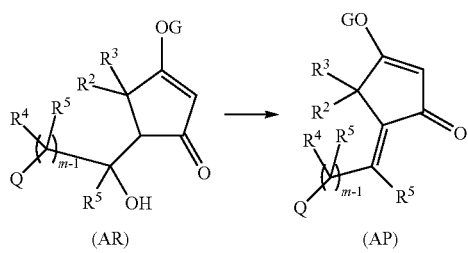

wherein $R^1$ and $R^4$ form a bond

Compounds of formula (AR) may be prepared by treating compounds of formula (AQ where in $R^1$ is hydrogen) with compounds of formula (AK) under basic conditions. Suitable bases include lithium diisopropylamide, sodium hexamethyldisilazide, potassium tert-butoxide and the reaction is preferably conducted in a suitable (such as tetrahydrofuran) at a temperature between −80° C. and 30° C. (see, for example, Aleman, J. et al. Chem. Comm. (2007), (38), 3921-3923).

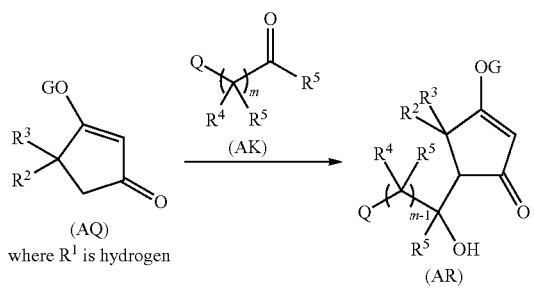

where $R^1$ is hydrogen

Compounds of formula (AN) may be prepared from compounds of formula (AP) by hydrolysis, preferably in the presence of an acid catalyst such as hydrochloric acid and optionally in the presence of a suitable solvent such as tetrahydrofuran or acetone preferably between 25° C. and 150° C. under conventional heating or under microwave irradiation.

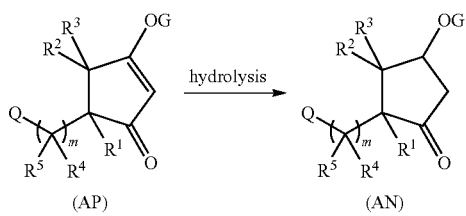

Alternatively, compounds of formula (AN) can be made from known compounds by known methods (see for example Manukina, T. A. et al. Zhurnal Organicheskoi Khimii (1986), 22(4), 873-4; Mellor, M. et al. Synth. Commun. 1979, 9 (1), 1-4).

In a further approach, compounds of formula (A) may be prepared by reacting compounds of formula (AN) with suitable heteroaryl halides (Het-Hal where Hal is, for example, an iodide or bromide), in the presence of a suitable palladium catalyst (for example 0.001-50% palladium(II) acetate with respect to compound (AN)) and a base (for example 1 to 10 equivalents potassium phosphate with respect to compound (AN)) and preferably in the presence of a suitable ligand (for example 0.001-50% (2-dicyclohexylphosphino)-2',4',6'-tri-isopropylbiphenyl with respect to compound (AN)), and in a suitable solvent (for example 1,4-dioxane), preferably between 25° C. and 200° C. Similar couplings are known in the literature (see for example, J. M. Fox, X. Huang, A. Chieffi, and S. L. Buchwald, J. Am. Chem. Soc. (2000), 122, 1360-1370; B. Hong et al. WO 2005/000233). Alternatively, compounds of formula (A) may be prepared by reacting compounds of formula (AN) with suitable heteroaryl halides (Het-Hal where Hal is, for example, an iodide or bromide) in the presence of a suitable copper catalyst (for example 0.001-50% copper(I) iodide with respect to compound (AN)) and a base (for example 1 to 10 equivalents potassium carbonate with respect to compound (AN)) and preferably in the presence of a suitable ligand (for example 0.001-50% L-proline with respect to compound (AN)), and in a suitable solvent (for example dimethylsulfoxide), preferably between 25° C. and 200° C. Similar couplings are known in the literature for aryl halides (see for example, Y. Jiang, N. Wu, H. Wu, and M. He, Synlett (2005), 18, 2731-2734).

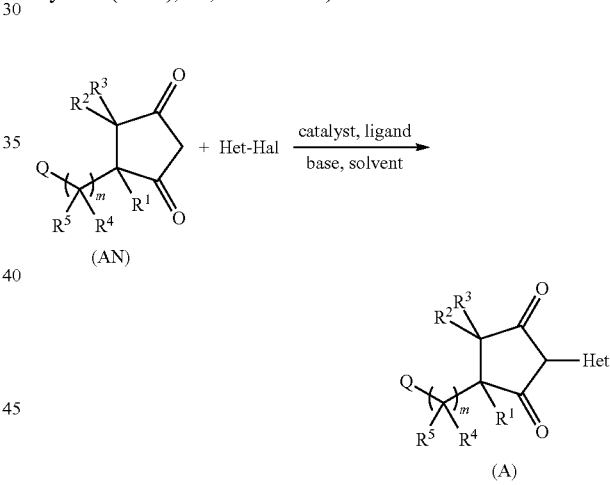

In a further approach, compounds of formula (A) may be prepared by reaction of compounds of formula (AN) with a heteroaryl lead tricarboxylates under conditions described in the literature (for example see, J. T. Pinhey, B. A. Rowe, Aust. J. Chem. (1979), 32, 1561-6; J. Morgan, J. T. Pinhey, J. Chem. Soc. Perkin Trans. 1 (1990), 3, 715-20; J. T. Pinhey, Roche, E. G. J. Chem. Soc. Perkin Trans. 1 (1988), 2415-21). Preferably the heteroaryl lead tricarboxylates are heteroaryl triacetates of formula (AS) and the reaction is conducted in the presence of a suitable ligand (for example N,N-dimethylaminopyridine, pyridine, imidazole, bipyridine, and 1,10-phenanthroline, preferably one to ten equivalents of N,N-dimethylaminopyridine with respect to compound (AN)) and in a suitable solvent (for example chloroform, dichloromethane and toluene, preferably chloroform and optionally in the presence of a co-solvent such as toluene) at 25° C. to 100° C. (preferably 60-90° C.).

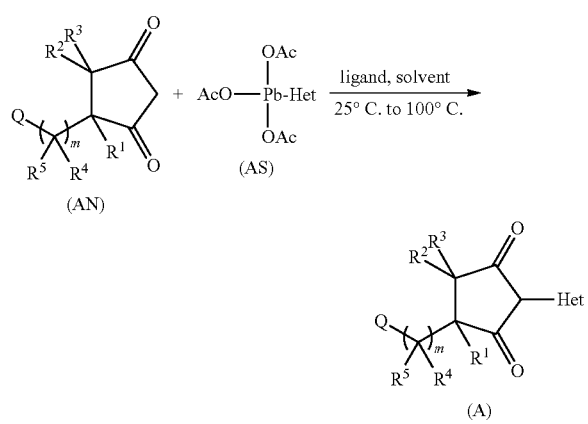

Compounds of formula (AS) may be prepared from compounds of formula (AM) by treatment with lead tetraacetate in a suitable solvent (for example chloroform) at 25° C. to 100° C. (preferably 25-50° C.), optionally in the presence of a catalyst such as mercury diacetate, according to procedures described in the literature (for example see, K. Shimi, G. Boyer, J-P. Finet and J-P. Galy, Letters in Organic Chemistry (2005), 2, 407-409; J. Morgan and J. T. Pinhey, J. Chem. Soc. Perkin Trans. 1 (1990), 3, 715-20).

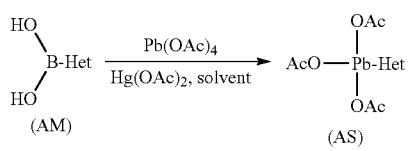

Additional compounds of formula (A) may be prepared by reacting an iodonium ylide of formula (AT), wherein Ar is an optionally substituted phenyl group, and an aryl boronic acid of formula (AM), in the presence of a suitable palladium catalyst, a base and in a suitable solvent.

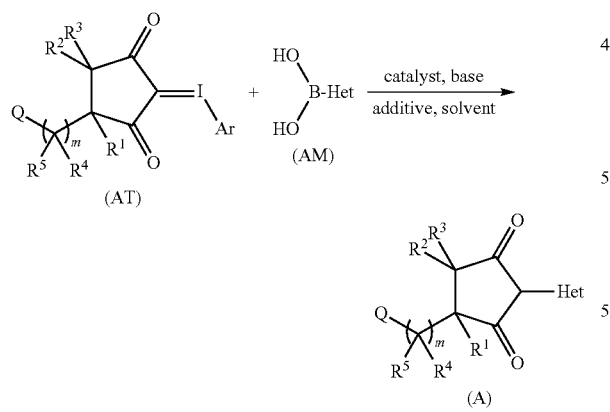

Suitable palladium catalysts are generally palladium(II) or palladium(0) complexes, for example palladium(II) dihalides, palladium(II) acetate, palladium(II) sulfate, bis(triphenylphosphine)-palladium(II) dichloride, bis(tricyclopentylphosphine)palladium(II) dichloride, bis(tricyclohexylphosphine)palladium(II) dichloride, bis(dibenzylideneacetone)palladium(0) or tetrakis-(triphenylphosphine)palladium(0). The palladium catalyst can also be prepared in situ from palladium(II) or palladium (0) compounds by complexing with the desired ligands, by, for example, combining the palladium(II) salt to be complexed, for example palladium(II) dichloride ($PdCl_2$) or palladium(II) acetate ($Pd(OAc)_2$), together with the desired ligand, for example triphenylphosphine ($PPh_3$), tricyclopentylphosphine, tricyclohexylphosphine, 2-dicyclohexylphosphino-2',6'-dimethoxybiphenyl or 2-dicyclohexylphosphino-2',4',6'-triisopropylbiphenyl and the selected solvent, with a compound of formula (AT), the arylboronic acid of formula (AM), and a base. Also suitable are bidendate ligands, for example 1, 1'-bis(diphenylphosphino)ferrocene or 1,2-bis (diphenylphosphino)ethane. By heating the reaction medium, the palladium(II) complex or palladium(0) complex desired for the C—C coupling reaction is thus formed in situ, and then initiates the C—C coupling reaction.

The palladium catalysts are used in an amount of from 0.001 to 50 mol %, preferably in an amount of from 0.1 to 15 mol %, based on the compound of formula (AT). The reaction may also be carried out in the presence of other additives, such as tetralkylammonium salts, for example, tetrabutylammonium bromide. Preferably the palladium catalyst is palladium acetate, the base is lithium hydroxide and the solvent is aqueous 1,2-dimethoxyethane.

A compound of formula (AT) may be prepared from a compound of formula (AN) by treatment with a hypervalent iodine reagent such as a (diacetoxy)iodobenzene or an iodosylbenzene and a base such as aqueous sodium carbonate, lithium hydroxide or sodium hydroxide in a solvent such as water or an aqueous alcohol such as aqueous ethanol according to the procedures of Schank K. et al. Synthesis (1983), 392, Moriarty R. M. et al. J. Am. Chem. Soc. (1985), 107, 1375 or of Yang Z. et al. Org. Lett. (2002), 4 (19), 3333.

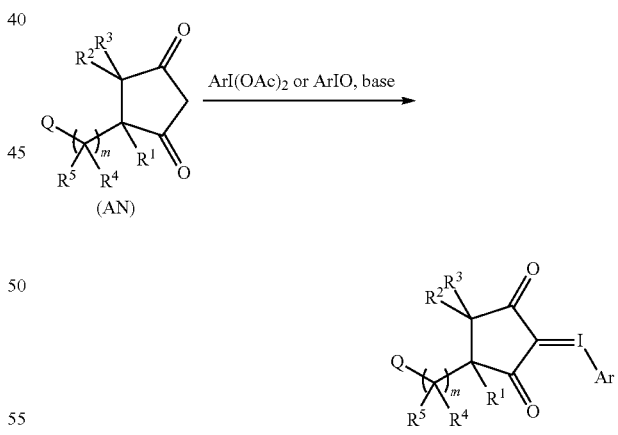

In a further approach to compounds of formula (A), compounds of formula (AU), which are compounds of formula (I) wherein G is hydrogen and Het is ($Het_2$) when $R^6$ is $CH_2R''''$ and $R''''$ is hydrogen or methyl, may be prepared by thermal rearrangement of compounds of formula (AU), optionally in the presence of a suitable solvent and optionally under microwave irradiation.

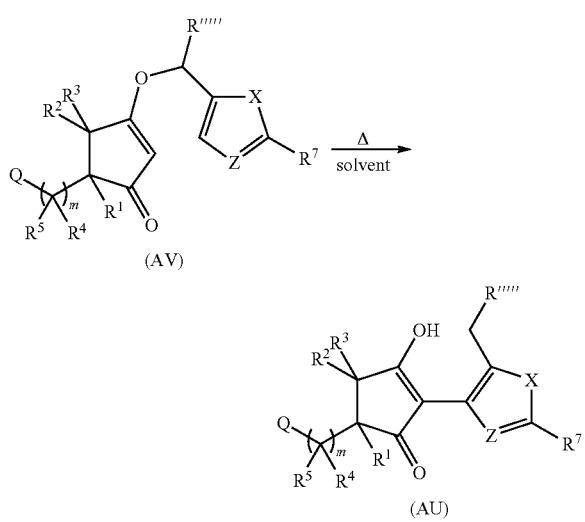

(AV)

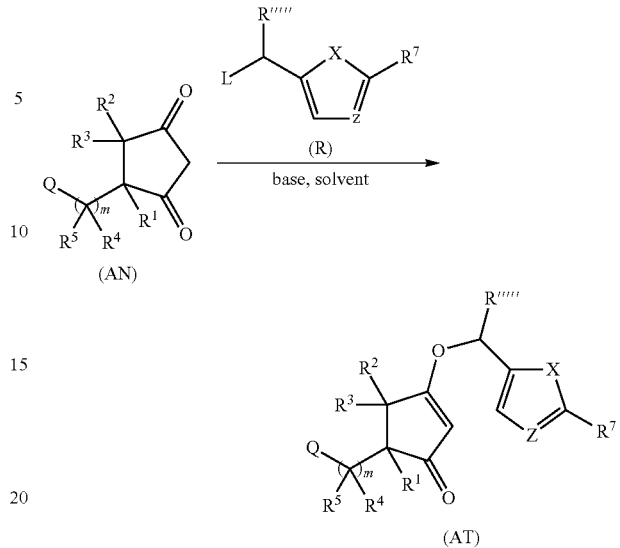

(AN)

(AT)

Preferably, the rearrangement is effected by heating compounds of formula (AT) at temperatures of between 120-300° C., optionally in a suitable solvent such as 1,2-dimethoxyethane, diethylene glycol methyl ether, triglyme, tetraglyme, xylene, mesitylene or Dowtherm®, and optionally under microwave irradiation.

Similarly, compounds of formula (AW), which are compounds of formula (I) wherein G is hydrogen and Het is (Het$_3$) when $R^6$ is $CH_2R''''$ and $R''''$ is hydrogen or methyl, may be prepared from compounds of formula (AX) using similar methods.

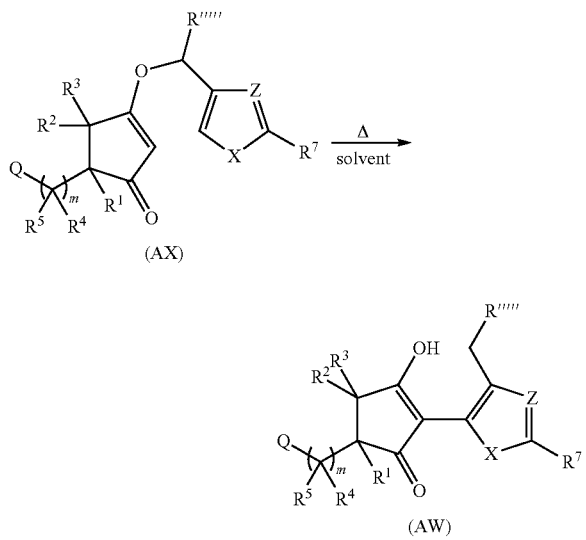

(AX)

(AW)

Compounds of formula (AV) may be prepared from compounds of formula (AN) by alkylation with compounds of formula (R), wherein L is a suitable leaving group such as a halogen or an alkyl- or aryl-sulfonate, optionally in the presence of a suitable base and optionally in a suitable solvent as described above for the alkylation of compounds of formula (A)

Similarly, compounds of formula (AX) may be prepared from compounds of formula (AN) by alkylation with compounds of formula (S), wherein L is a suitable leaving group such as a halogen or an alkyl- or aryl-sulfonate, under similar conditions.

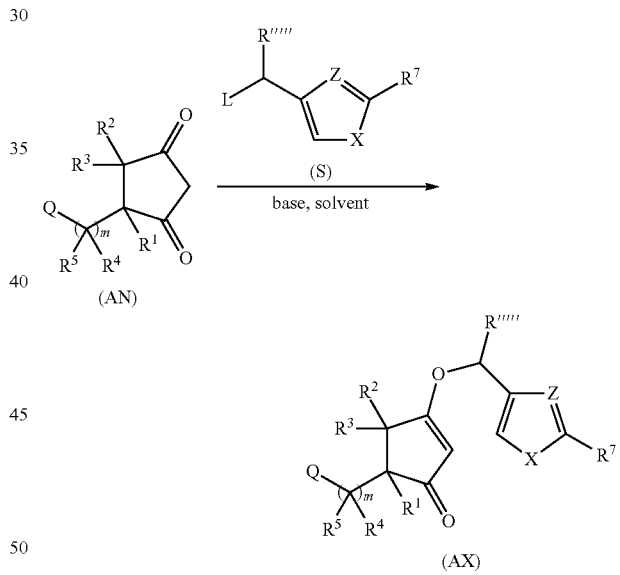

(AN)

(AX)

In an alternative approach, compounds of formula (AV) may be prepared from compounds of formula (AN) by condensation with alcohols of formula (T), optionally in the presence of a suitable acid catalyst such as p-toluenesulfonic acid, or a Lewis acid catalyst, for example, ytterbium (III) trifluoromethanesulfonate, lanthanum (III) trifluoromethanesulfonate, sodium tetrachloroaurate (III) dihydrate, titanium (IV) chloride, indium (III) chloride or aluminium chloride, and optionally in a suitable solvent. Suitable solvents are selected to be compatible with the reagents used, and include, for example, toluene, ethanol or acetonitrile. Similar approaches have been described by, for example, M. Curini; F. Epifano, S. Genovese, Tetrahedron Lett. (2006), 47, 4697-700; A. Arcadi, G. Bianchi, S. Di Giuseppe, F. Marinelli, Green Chemistry (2003), 5, 64-7.

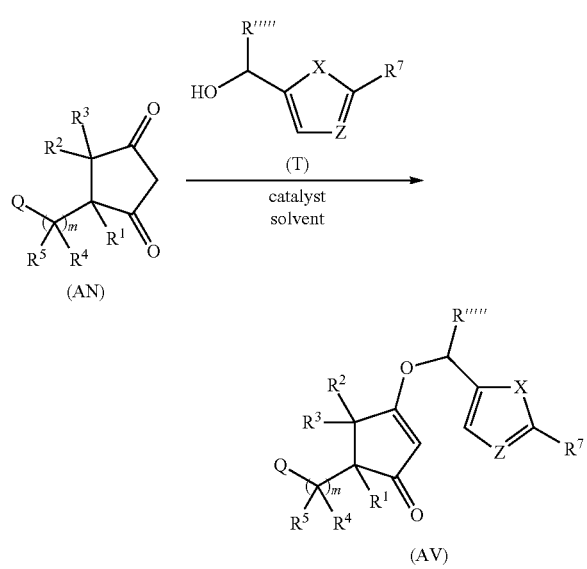

(AN) + (T) →catalyst, solvent→ (AV)

Alternatively, the condensation may be effected in the presence of suitable coupling agents such as 2-chloro-1-methylpyridinium iodide, N,N'-dicyclohexylcarbodiimide, 1,(3-dimethylaminopropyl)-3-ethylcarbodiimimde and N,N-carbodiimidazole and a suitable base such a triethylamine or pyridine in a suitable solvent such as tetrahydrofuran, acetonitrile or dichloromethane, or in the presence of a triaryiphosphine (such as triphenylphosphine) and a dialkyl azidodicarboxylate (preferably diethyl azidodicarboxylate or diisopropyl azidodicarboxylate) and in a suitable solvent such as diethyl ether, tetrahydrofuran or 1,4-dioxane as described, for example, by O. Mitsunobu, Synthesis (1981), 1, 1-28.

Using similar processes, compounds of formula (AX) may be prepared by reaction of compounds of formula (AN) with compounds of formula (U).

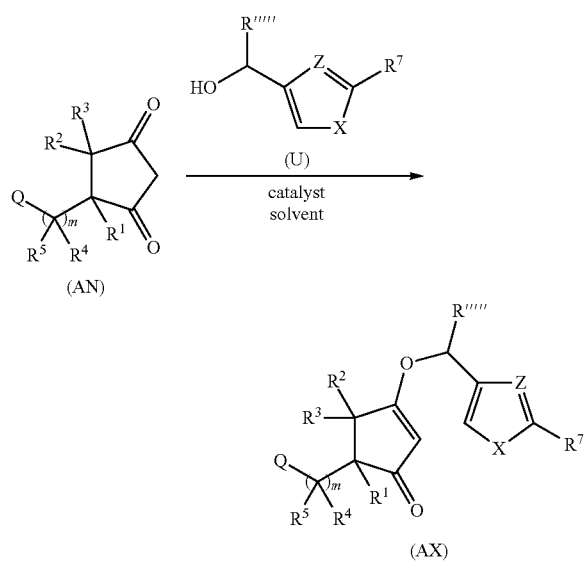

(AN) + (U) →catalyst, solvent→ (AX)

Additional compounds of formula (AV) wherein $R^7$ is an aromatic or heteroaromatic moiety, or is an alkyl, alkenyl or alkynyl group, may be prepared by the reaction of compounds of formula (AY), wherein A is an atom or group suitable for undergoing cross-coupling reactions (for example A is chlorine, bromine or iodine, or a haloalkylsulfonate such as trifluoromethanesulfonate), and R''''' is as defined for compound of formula (O), with a suitable coupling partner under conditions described in the literature for Suzuki-Miyaura, Sonogashira, Stille and related cross-coupling reactions.

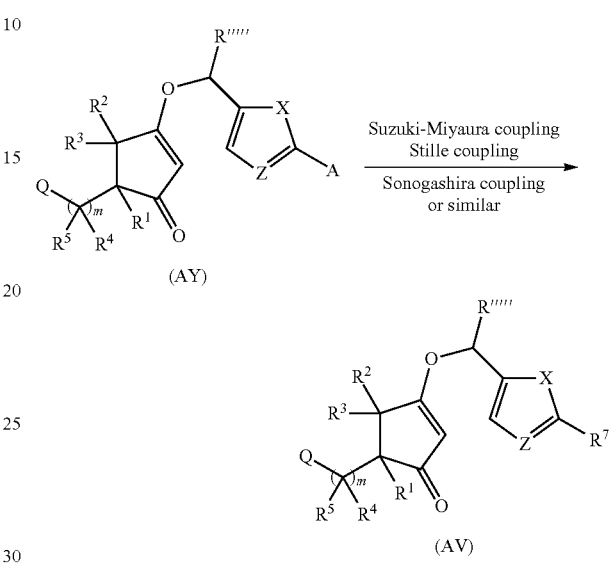

(AY) →Suzuki-Miyaura coupling / Stille coupling / Sonogashira coupling or similar→ (AV)

For example, compounds of formula (AY) may be treated with aryl-, heteroaryl-, alkyl-, alkenyl- or alkynylboronic acids, $R^7$—$B(OH)_2$, boronate esters, $R^7$—$B(OR''''')_2$, wherein R''''' is $C_1$-$C_6$alkyl or $R^7$—$B(OR''''')_2$ represents cyclic boronate esters derived from a $C_1$-$C_6$diol (especially preferred are cyclic boronate esters derived from pinacol), or a metal (especially potassium) aryl-, heteroaryl, alkyl-, alkenyl- and alkynyltrifluoroborate salts, $M^+[R^7$—$BF_3]^-$ in the presence of a suitable palladium catalyst, a suitable ligand and a suitable base in the presence of a suitable solvent, under Suzuki-Miyaura conditions (see, for example K. Billingsley and S. Buchwald, J. Am. Chem. Soc. (2007), 129, 3358-3366; H. Stefani, R. Cella and A. Vieira, Tetrahedron (2007), 63, 3623-3658; N. Kudo, M. Perseghini and G. Fu, Angew. Chem. Int. Ed. (2006), 45, 1282-1284; A. Roglans, A. Pla-Quintana and M. Moreno-Mañas, Chem. Rev. (2006), 106, 4622-4643; J-H Li, Q-M Zhu and Y-X Xie, Tetrahedron (2006), 10888-10895; S, Nolan et al., J. Org. Chem. (2006), 71, 685-692; M. Lysén and K. Köhler, Synthesis (2006), 4, 692-698; K. Anderson and S. Buchwald, Angew. Chem. Int. Ed. (2005), 44, 6173-6177; Y. Wang and D. Sauer, Org. Lett. (2004), 6 (16), 2793-2796; I. Kondolff, H. Doucet and M, Santelli, Tetrahedron, (2004), 60, 3813-3818; F. Bellina, A. Carpita and R. Rossi, Synthesis (2004), 15, 2419-2440; H. Stefani, G. Molander, C-S Yun, M. Ribagorda and B. Biolatto, J. Org. Chem. (2003), 68, 5534-5539; A. Suzuki, Journal of Organometallic Chemistry (2002), 653, 83; G. Molander and C-S Yun, Tetrahedron (2002), 58, 1465-1470; G. Zou, Y. K. Reddy and J. Falck, Tetrahedron Lett. (2001), 42, 4213-7215; S. Darses, G. Michaud and J-P, Genet, Eur. J. Org. Chem. (1999), 1877-1883).

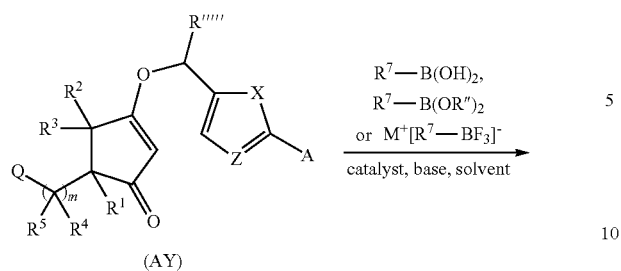

(AY)

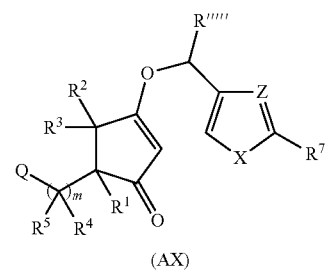

(AX)

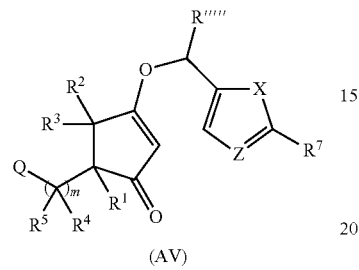

(AV)

Compounds of formula (AY) may be prepared from compounds of formula (AN), by reaction with compounds of formula (Z) wherein L is a suitable leaving group such as a halogen or an alkyl- or aryl-sulfonate, by processes analogous to those described above for the preparation of compounds of formula (AV) from compounds of formula (AN). Alternatively, compounds of formula (AY) may be prepared by reaction of compounds of formula (AN) with compounds of formula (AA) by processes analogous to those described above for the preparation of compounds of formula (AV) from compounds of formula (AN).

Alternatively, compounds of formula (AV), wherein $R^7$ is an optionally substituted acetylene, may be prepared from compounds of formula (AY) by reacting with a terminal alkyne, $R^7$—H, in the presence of a suitable palladium catalyst and optionally in the presence of a suitable copper co-catalyst, a suitable ligand, a suitable base and a suitable additive under conditions known to effect the Sonogashira coupling (see, for example, U. Sorenson and E Pombo-Villar, Tetrahedron (2005), 2697-2703; N. Leadbeater and B. Tominack, Tetrahedron Lett. (2003), 44, 8653-8656; K. Sonogashira, J. Organomet. Chem. (2002), 653, 46-49).

In a further approach, compounds of formula (AV), wherein $R^7$ is alkyl, optionally substituted vinyl, optionally substituted ethynyl, optionally substituted aryl or optionally substituted heteroaryl, may be prepared from compounds of formula (AY) by reaction with a suitable organnostannane under Stille conditions (see, for example, R. Bedford, C. Cazin and S. Hazlewood (2002), 22, 2608-2609; S. Ley et al., Chem. Commun. (2002), 10, 1134-1135; G. Grasa and S, Nolan, Org. Lett. (2001), 3 (1), 119-122; T. Weskamp, V. Boehm, J. Organomet. Chem. (1999), 585 (2), 348-352; A. Littke and G. Fu, Angew. Chem. Int. Ed. (1999), 38 (16), 2411-2413; J. Stille et al., Org. Synth. (1992), 71, 97).

Compounds of formula (AX) may be prepared from compounds of formula (AZ), wherein A and R'''' are as defined for compounds of formula (AY), by analogous methods using appropriate starting materials.

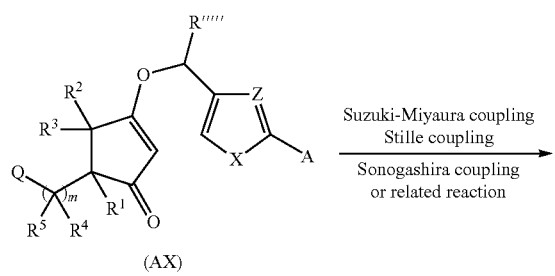

(AX)

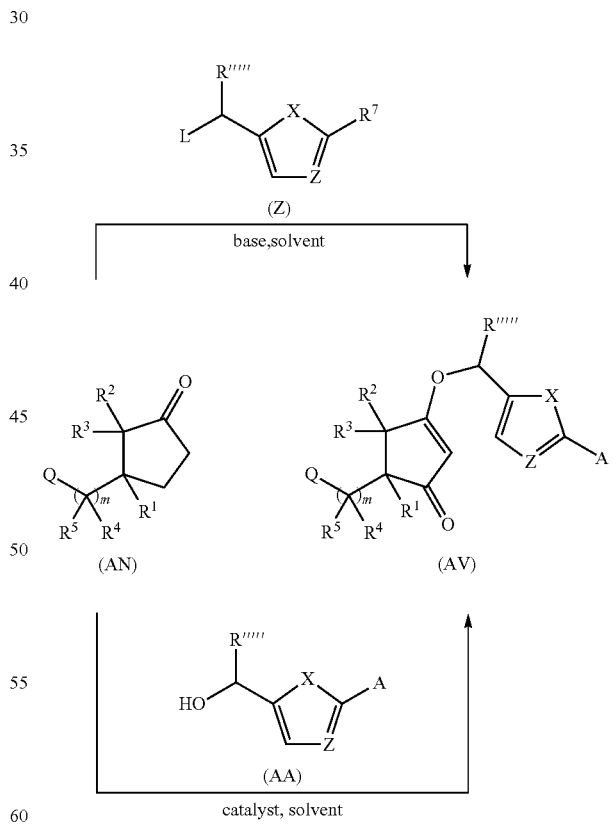

Compounds of formula (AZ) may be prepared from compounds of formula (AN), by reaction with compounds of formula (AB) wherein L is a suitable leaving group such as a halogen or an alkyl- or aryl-sulfonate, by processes analogous to those described above for the preparation of compounds of formula (AV) from compounds of formula (AN). Alternatively, compounds of formula (AZ) may be prepared by reaction of compounds of formula (AN) with compounds of formula (AB) by processes analogous to those described above for the preparation of compounds of formula (AV) from compounds of formula (AN).

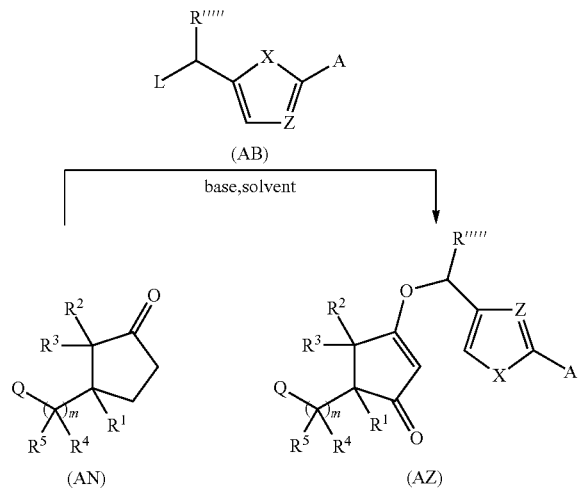

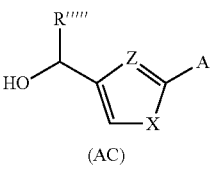

In an alternative approach, compounds of formula (AN) may be treated with a halogenating agent such as phosphorus oxychloride, phosphorus pentachloride, phosphorus pentabromide, phosphorus oxybromide, oxalyl chloride or oxalyl bromide, optionally in a suitable solvent such as toluene, chloroform, dichloromethane with optionally the presence of dimethylformamide, and the resulting vinyl halides of formula (BA), wherein Hal is chlorine or bromine may be converted by reaction with alcohols of formula (T), or of formula (U), or of formula (AA) or of formula (AC) optionally in the presence of a suitable base such as sodium hydride, sodium tert-butoxide, potassium tert-butoxide and a suitable solvent such as tetrahydrofuran, 1,4-dioxane, diethylene glycol dimethyl ether to give compounds of formula (AV), formula (AX), formula (AY) and formula (AZ) respectively:

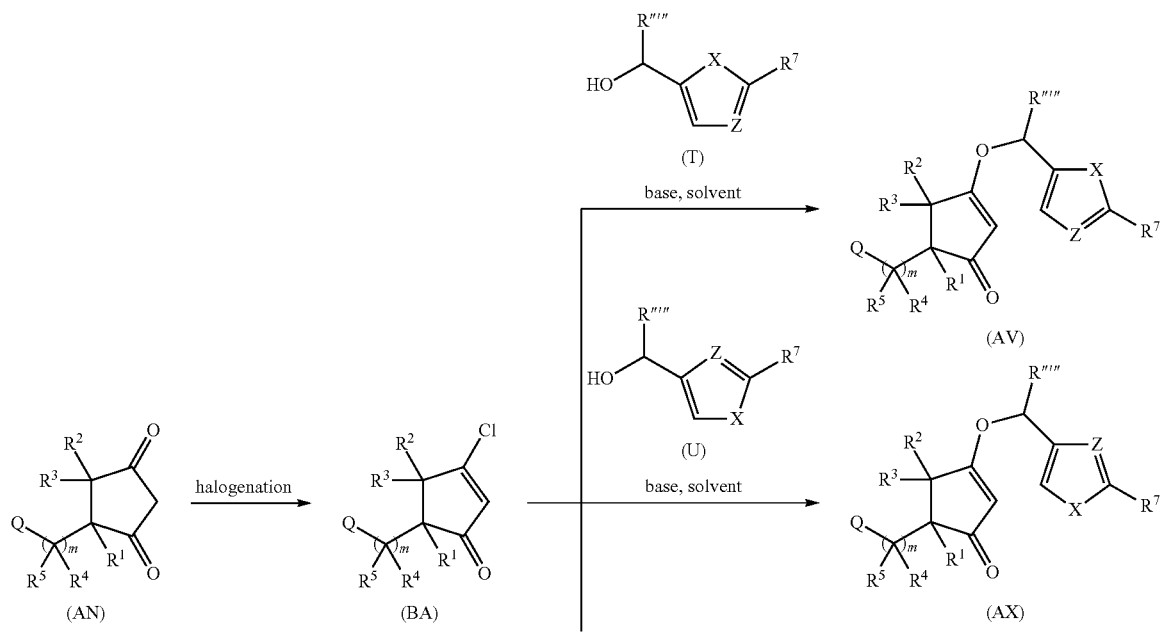

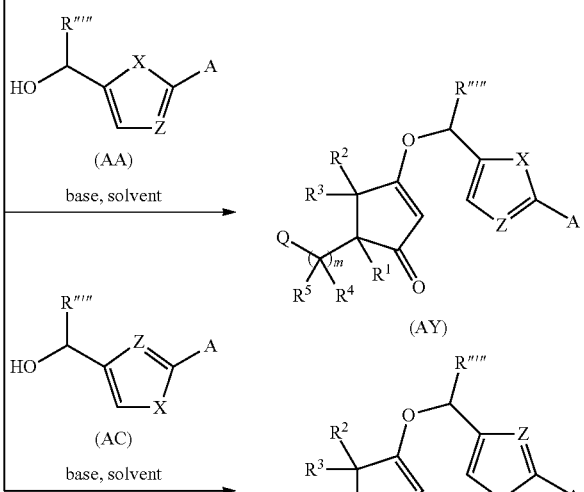

Compounds of formula (BA) may be also prepared from compounds of formula (BB) by an intramolecular Friedel-Crafts-type cyclisation by treating the carboxylic acid (BB) with halogenating agent, such as phosphorus oxychloride, phosphorus pentachloride, phosphorus pentabromide, phosphorus oxybromide, oxalyl chloride or oxalyl bromide, optionally in a suitable solvent such as toluene, chloroform, dichloromethane with optionally the presence of dimethylformamide, treating the reaction mixture with a Lewis acid, preferably $AlCl_3$ and subsequently doing a standard aqueous workup, using, for example, a saturated aqueous solution of sodium bicarbonate (see, for example, Y. Xu et al. J. Org. Chem. 2009, DOI: 10.1021/jo900696k).

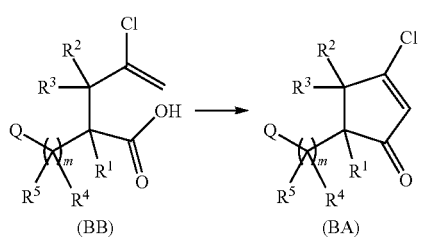

Compounds of formula (BB) may be prepared from compounds of formula (BC), by reaction 2-chloro-3-iodopropene derivates under basic conditions. Suitable bases include sodium bis(trimethylsilyl)amide, lithium diisopropylamide, n-butyl lithium and the reaction is preferably conducted in a suitable solvent (such as tetrahydrofuran or toluene) at a temperature of between −80° C. and 30° C. (see, for example, Y. Xu et al. J. Org. Chem. 2009, DOI: 10.1021/jo900696k).

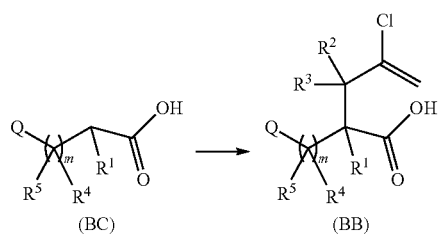

Compounds of formula (BC) are known or may be made from known compounds by known methods.

In a further approach to compounds of formula (A), wherein Het is a group of formula ($Het_2$), X is S, and Z is N, compounds of formula (BD) wherein L is a suitable leaving group such as a halogen or an alkyl- or haloalkylsulfonate, may be treated with compounds of formula (BE) in the presence of a suitable base (such as triethylamine or pyridine), and optionally in a suitable solvent (such as water, acetone, ethanol or isopropanol) according to known procedures, (see, for example, E. Knott, J. Chem. Soc. (1945), 455; H. Brederick, R. Gompper, Chem. Ber. (1960), 93, 723; B. Friedman, M. Sparks and R. Adams, J. Am. Chem. Soc. (1937), 59, 2262).

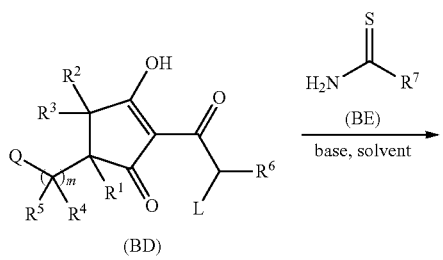

-continued

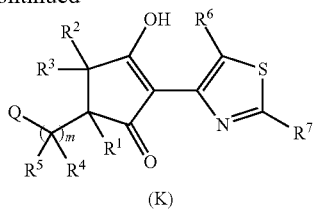

(K)
where G is H and
Het is Het$_2$
X is S and Z is N

Alternatively, compounds of formula (BD) may be treated with thiourea, by known procedures (see, for example, V. Pshenichniya, O. Gulyakevich and V. Kripach, Chemistry of Heterocyclic Compounds (1990), 10, 1409-1412), and the resulting products of formula (BF) may be converted into additional compounds of formula (I) by conversion to halides of formula (BG), wherein Hal is chlorine, bromine or iodine, under Sandmeyer conditions, and compounds of formula (BG) may be converted to compounds of formula (I) by cross-coupling under known conditions for the Suzuki-Miyaura, Sonogashira, Stille and related reactions, as described previously.

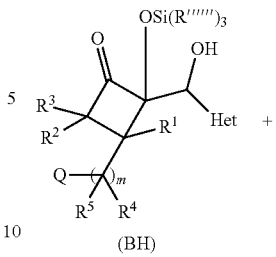

(BH)

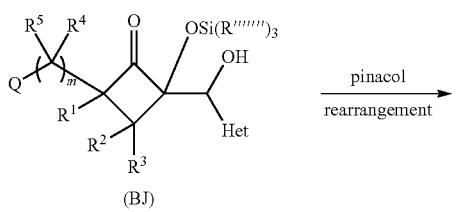

(BJ)

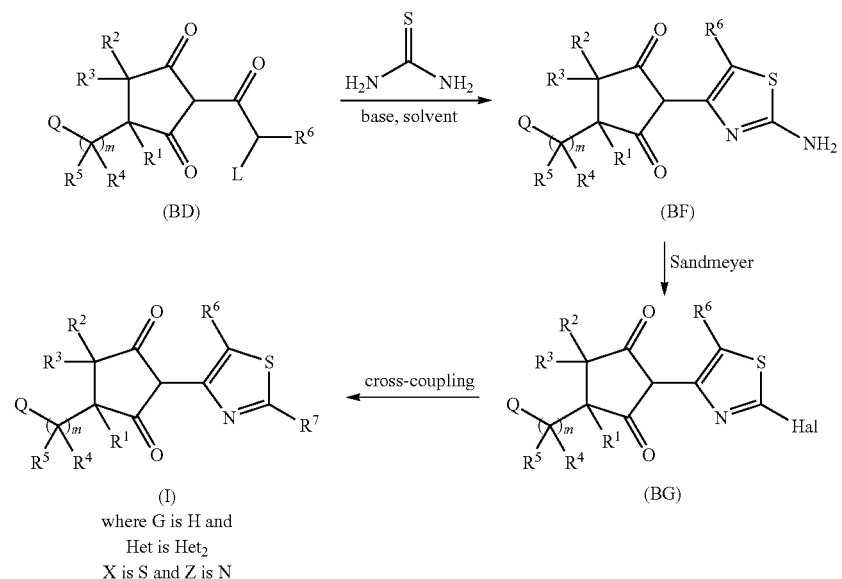

(I)
where G is H and
Het is Het$_2$
X is S and Z is N

Compounds of formula (BD) may be prepared from compounds of formula (AN) under known conditions (see, for example, V. Pshenichniya, O. Gulyakevich and V. Kripach, Chemistry of Heterocyclic Compounds (1990), 10, 1409-1412; V. Pshenichniya, O. Gulyakevich and V. Kripach, Russian Journal of Organic Chemistry (1989), 25 (9), 1882-1888).

Additional compounds of formula (A) may be prepared by the pinacol rearrangement of compounds of formula (BG) or compounds of formula (BJ) wherein R'''''' is $C_1$-$C_4$ alkyl (preferably methyl) under acidic conditions (see, for example, Eberhardt, U. et. al. Chem. Ber. (1983), 116(1), 119-35 and Wheeler, T. N. U.S. Pat. No. 4,283,348)

-continued

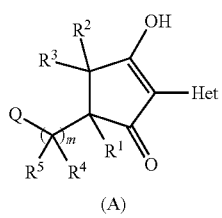

(A)

Compounds of formula (BH) and compounds of formula (BJ) may be prepared by treating compounds of formula (BK) with compounds of formula (BL) in the presence of an acid (such as titanium tetrachloride or magnesium iodide) optionally in a suitable solvent (such as dichloromethane) at a temperature between −80° C. and 30° C. (see, for example, Li, W.-D. Z. and Zhang, X.-X. Org. Lett. (2002), 4(20), 3485-3488; Shimada, J. et al. J. Am. Chem. Soc. (1984), 106(6), 1759-73; Eberhardt, U. et. al. Chem. Ber. (1983), 116(1), 119-35 and Wheeler, T. N. U.S. Pat. No. 4,283,348).

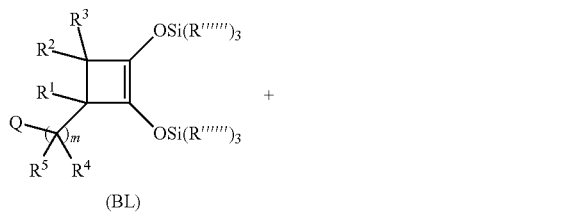

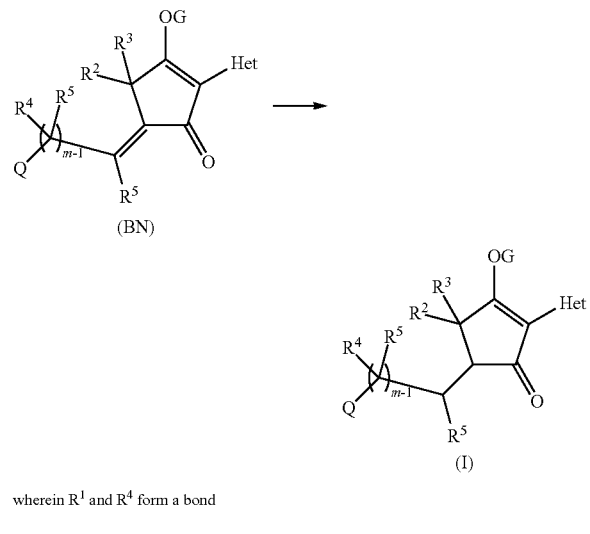

wherein $R^1$ and $R^4$ form a bond

Compounds of formula (BM) may be prepared from compounds of formula (BO) under basic or acidic conditions. For example of a procedure see G. Quinkert et al. Helv. Chim. Acta, 1986, 69(3), 469-537.

Compounds of formula (BK) are known or may be made from known compounds by known methods.

Compounds of formula (BL) may be prepared from compounds of formula (BM) where in R''' is an alkyl group (preferably methyl) in the presence of chloro tri-$C_1$-$C_4$alkyl silyl and a metal (preferably sodium) in a suitable solvent (such as toluene or diethyl ether) at a temperature between 20° C. and 150° C. (see, for example, Blanchard, A. N. and Burnell, D. J. Tetrahedron Lett. (2001), 42(29), 4779-4781 and Salaun, J. et al. Tetrahedron (1989), 45(10), 3151-62).

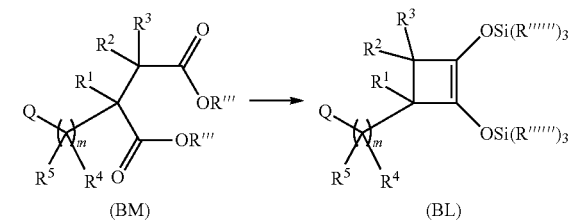

Compounds of formula (BM) are analogous to compounds of formula (H) and compounds of formula (G) and may be prepared by know methods analogous to those describe for compounds of formula (H) and compounds of formula (G).

Additional compounds of formula (I) may be prepared wherein $R^1$ and $R^4$ form a bond and $R^5$ is $C_1$-$C_6$alkylsulfonate (preferably mesylate) or $C_1$-$C_6$haloalkylsulfonate (preferably triflate) or an arylsulfonate (preferable tosylate) may be prepared from compounds of formula (BN) following known procedures (Specklin et al. J. Org. Chem. 2008, 73(19), 7845-7848).

Compounds of formula (BO) may be prepared by reaction of compounds of formula (K) wherein $R^5$ is hydrogen with acids chloride of formula (BP) in the presence of a base.

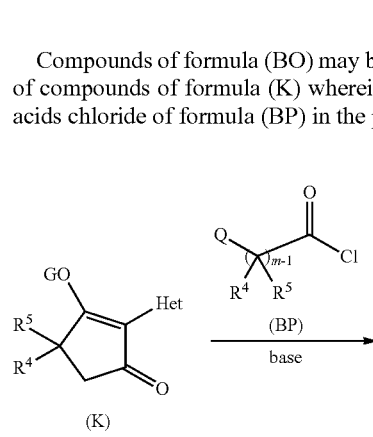

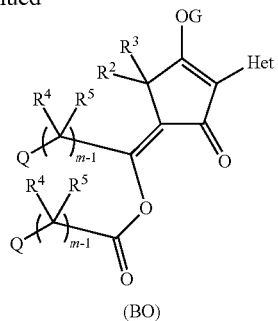

(BO)

Compounds of formula (BP) are known or may be made by known methods from known compounds.

Alternatively, compounds of formula (BN) can be prepared from compounds of formula (AJ) using known oxidative procedures (see for example D. B. Dess and J. C. Martin J. Org. Chem. 1983, 48 (22), 4155-4156).

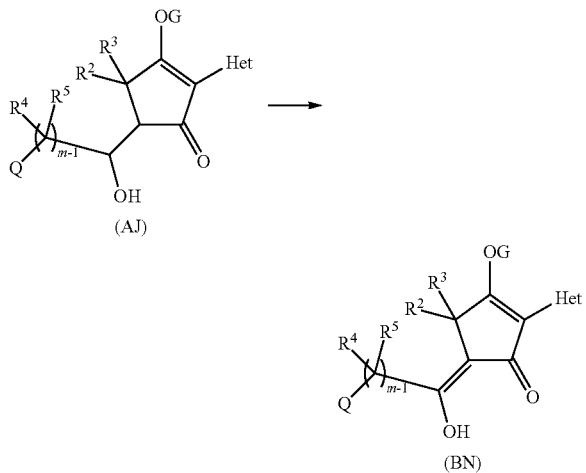

wherein $R^5$ is hydrogen

The compounds of formula I according to the invention can be used as crop protection agents in unmodified form, as obtained in the synthesis, but they are generally formulated into crop protection compositions in a variety of ways using formulation adjuvants, such as carriers, solvents and surface-active substances.

Hence, the invention also provides a herbicidal composition, which comprises a herbicidally effective amount of a compound of formula I as defined herein.

The formulations (compositions) can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or microrods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means.

Diluted formulations can be prepared, for example, with water, liquid fertilisers, micro-nutrients, biological organisms, oil or solvents.

The formulations can be prepared, for example, by mixing the active ingredient with formula-tion adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, or chemically modified cellulose esters like carboxymethyl cellulose, methyl cellulose, or hydroxyethyl cellulose. Examples of suitable waxes are polyethylene wax, oxidized polyethylene wax, ester waxes like montan waxes, waxes of natural origin like carnauba wax, candelilla wax, or beeswax etc. Other suitable matrix materials for slow release formulations are starch, stearin, or lignin.

The formulation adjuvants suitable for the preparation of the compositions according to the invention are generally known per se.

As liquid carriers there may be used: water, aromatic solvents such as toluene, m-xylene, o-xylene, p-xylene and mixtures thereof, cumene, aromatic hydrocarbon blends with boiling ranges between 140 and 320° C. known under various trademarks like Solvesso®, Shellsol A®, Caromax®, Hydrosol®, paraffinic and isoparaffinic carriers such as paraffin oils, mineral oils, de-aromatized hydrocarbon solvents with boiling ranges between 50 and 320° C. known for instance under the trademark Exxsol®, non-dearomatized hydrocarbon solvents with boiling ranges between 100 and 320° C. known under the tradename Varsol®, isoparaffinic solvents with boiling ranges between 100 and 320° C. known under tradenames like Isopar® or Shellsol T®, hydrocarbons such as cyclohexane, tetrahydronaphthalene (tetralin), decahydronaphthalene, alpha-pinene, d-limonene, hexadecane, isooctane, ester solvents such as ethyl acetate, n/i-butyl acetate, amyl acetate, i-bornyl acetate, 2-ethylhexyl acetate, $C_6$-$C_{18}$ alkyl esters of acetic acid known under the tradename Exxate®, lactic acid ethylester, lactic acid propylester, lactic acid butylester, benzyl benzoate, benzyl lactate, dipropyleneglycol dibenzoate, dialkyl esters of succinic, maleic and fumaric acid and polar solvents like N-methylpyrrolidone, N-ethyl pyrrolidone, $C_3$-$C_{18}$-alkyl pyrrolidones, gamma-butyrolactone, dimethylsulfoxide, N,N-dimethylformamide, N,N-dimethylacetamide, N,N-dimethyllactamide, $C_4$-$C_{18}$ fatty acid dimethylamides, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, butylene carbonate, alcoholic solvents and diluents such as methanol, ethanol, propanol, n/iso-butanol, n/iso-pentanol, 2-ethyl hexanol, n-octanol, tetrahydrofurfuryl alkohol, 2-methyl-2,4-pentanediol, 4-hydroxy-4-methyl-2-pentanon, cyclohexanol, benzyl alcohol, ethylene glycol, ethylene glycol butyl ether, ethylene glycol methyl ether, diethylene glycol, diethylene glycol butyl ether, diethylene glycol ethyl ether, diethylene glycol methyl ether, propylene glycol, dipropylene glycol, dipropylene glycol methyl ether and other similar glycol ether solvents based on ethylene glycol, propylene glycol and butylene glycol feedstocks, triethylene glycol, polyethylene glycol (PEG 400), polypropylenglycols with molecular masses of 400-4000, glycerol, glycerol acetate, glycerol diacetate, glycerol triacetate, 1,4-dioxane, diethylene glycol abietate, chlorobenzene, chlorotoluene, fatty acid esters such as methyl octanoate, isopropyl myristate, methyl laurate, methyl oleate, mixture of $C_8$-$C_{10}$ fatty acid methyl esters, rape seed oil methyl and ethyl esters, soy bean oil methyl and ethyl esters, vegetable oils, fatty acids such as oleic acid, linoleic acid, linolenic acid, esters of phosphoric and phosphonic acid such as triethyl phosphate, $C_3$-$C_{18}$-tris-alkyl phosphates, alkylaryl phosphates, bis-octyl-octyl phosphonates.

Water is generally the carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations, especially in those formulations which can be diluted with a carrier prior to use. Surface-active substances may be anionic, cationic, amphoteric, non-ionic or polymeric and they may be used as emulsifiying, wetting, dispersing or suspending agents or for other purposes. Typical surface-active substances include, for example, salts of alkyl sulfates, such as diethanolammonium lauryl sulphate; Sodium lauryl sulphate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, antifoams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, compatibility agents and solubilisers and also liquid and solid fertilisers.

The formulations may also comprise additional active substances, for example further herbicides, herbicide safeners, plant growth regulators, fungicides or insecticides.

Therefore, the invention also provides a herbicidal composition, which comprises a herbicidally effective amount of a compound of formula I as defined herein, and optionally (or preferably) a further herbicide as mixture partner for the compound of formula I, or optionally (or preferably) a safener, or both.

The invention also provides a herbicidal composition, which comprises a herbicidally effective amount of a compound of formula I as defined herein, a safener, and optionally (or preferably) a further herbicide as mixture partner for the compound of formula I, wherein the safener is benoxacor, cloquintocet-mexyl, cyprosulfamide, mefenpyr-diethyl or N-(2-methoxybenzoyl)-4-[(methylaminocarbonyl)amino]benzenesulfonamide.

The compositions according to the invention can additionally include an additive (commonly referred to as an adjuvant), comprising a mineral oil, an oil of vegetable or animal origin, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsifiable vegetable oil, such as AMIGO® (Loveland Products Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is AGNIQUE ME 18 RD- F® (Cognis). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic, cationic or amphoteric surfactants. Examples of suitable anionic, non-ionic, cationic or amphoteric surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total additive is generally from 1 to 50% by weight. Examples of oil additives that consist of mixtures of oils or mineral oils or derivatives thereof with surfactants are TURBOCHARGED, ADIGOR® (both (Syngenta Crop Protection AG), ACTIPRON® (BP Oil UK Limited), AGRIDEX® (Helena Chemical Company).

The said surface-active substances may also be used in the formulations alone, that is to say without oil additives.

Furthermore, the addition of an organic solvent to the oil additive/surfactant mixture can contribute to a further enhancement of action. Suitable solvents are, for example, SOLVESSO® and AROMATIC® solvents (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF). Further oil additives that are preferred according to the invention are SCORE® and ADIGOR® (both Syngenta Crop Protection AG).

In addition to the oil additives listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

Such adjuvant oils as described in the preceding paragraphs may be employed as the carrier liquid in which an active compound is dissolved, emulsified or dispersed as appropriate to the physical form of the active compound.

The pesticidal (e.g. herbicidal) formulations generally contain from 0.1 to 99% by weight, especially from 0.1 to 95% by weight, of a compound of formula I, and preferably from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1 to 2000g/ha, preferably 1 to 1000g/ha, most preferably at 1 to 500g/ha, and most preferably at 10 to 250g/ha (in particular at 10, 15, 16, 20, 30, 50, 60, 62.5, 100, 125 or 250g/ha).

Preferred formulations have especially the following representative compositions:
(%=percent by weight):
Emulsifiable Concentrates:
active ingredient: 1 to 95%, preferably 60 to 90%
surface-active agents: 1 to 30%, preferably 5 to 20%
solvents as liquid carrier: 1 to 80%, preferably 1 to 35%
Dusts:
active ingredient: 0.1 to 10%, preferably 0.1 to 5%
solid carriers: 99.9 to 90%, preferably 99.9 to 99%
Suspension Concentrates:
active ingredient: 5 to 75%, preferably 10 to 50
water: 94 to 24%, preferably 88 to 30%
surface-active agents: 1 to 40%, preferably 2 to 30%
Wettable Powders:
active ingredient: 0.5 to 90%, preferably 1 to 80%
surface-active agents: 0.5 to 20%, preferably 1 to 15%
solid carriers: 5 to 95%, preferably 15 to 90%
Granules:
active ingredient: 0.1 to 30%, preferably 0.1 to 15%
solid carriers: 99.5 to 70%, preferably 97 to 85%
Waterdispersible Granules:
active ingredient: 1 to 90%, preferably 10 to 80%
surface-active agents: 0.5 to 80%, preferably 5 to 30%
solid carriers: 90 to 10%, preferably 70 to 30%

The following Examples further illustrate, but do not limit, the invention.

F1. Emulsifiable Concentrates

|  | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | 10% | — | 20% |
| arom. hydrocarbon mixture $C_9$-$C_{12}$ | 85% | 68% | 65% | 16% |

Emulsions of any desired concentration can be prepared from such concentrates by dilution with water.

F2. Solutions

|  | a) | b) | c) | d) |
|---|---|---|---|---|
| active ingredient | 5% | 10% | 50% | 90% |
| 1-methoxy-3-(3-methoxy-propoxy)-propane | 40% | 50% | — | — |
| polyethylene glycol MW 400 | 20% | 10% | — | — |
| NMP | — | — | 50% | 10% |
| arom. hydrocarbon mixture $C_9$-$C_{12}$ | 35% | 30% | — | — |

The solutions are suitable for application undiluted or after dilution with water.

F3. Wettable Powders

|  | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |

-continued

|  | a) | b) | c) | d) |
|---|---|---|---|---|
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

F4. Coated Granules

|  | a) | b) | c) |
|---|---|---|---|
| active ingredient | 0.1% | 5% | 15% |
| highly dispersed silica | 0.9% | 2% | 2% |
| inorg. carrier (diameter 0.1-1 mm) | 99.0% | 93% | 83% | e.g. CaCO$_3$ or SiO$_2$

The active ingredient is dissolved in methylene chloride, the solution is sprayed onto the carrier and the solvent is subsequently evaporated off in vacuo.

F5. Coated Granules

|  | a) | b) | c) |
|---|---|---|---|
| active ingredient | 0.1% | 5% | 15% |
| polyethylene glycol MW 200 | 1.0% | 2% | 3% |
| highly dispersed silica | 0.9% | 1% | 2% |
| inorg. carrier (diameter 0.1-1 mm) | 98.0% | 92% | 80% | e.g. CaCO$_3$ or SiO$_2$

The finely ground active ingredient is applied uniformly, in a mixer, to the carrier moistened with polyethylene glycol. Non-dusty coated granules are obtained in this manner.

F6. Extruded Granules

|  | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

F7. Water-Dispersible Granules

|  | a) | b) | c) | d) |
|---|---|---|---|---|
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% |  |
| Sodium sulphate |  | 4% | 5% |  |
| kaolin | 48% | 30% | 30% |  |

The active ingredient is mixed and ground with the adjuvants and the mixture is moistened with water. The resulting mixture is extruded and then dried in a stream of air.

F8. Dusts

|  | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

F9. Suspension Concentrates

|  | a) | b) | c) | d) |
|---|---|---|---|---|
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-Benzisothiazolin-3-on | 0.1% | 0.1% | 0.1% | 0.1% |
| silicone oil emulsion | 0.7% | 0.7% | 0.7% | 0.7% |
| water | 87% | 79% | 62% | 38% |

The finely ground active ingredient is intimately mixed with the adjuvants, yielding a suspension concentrate from which suspensions of any desired concentration can be prepared by dilution with water.

The invention also provides a method of controlling grasses and weeds in crops of useful plants, which comprises applying a herbicidally effective amount of a compound of formula I as defined herein, or of a composition comprising such a compound, to the plants or to the locus thereof.

Crops of useful plants, in which the compositions and/or the methods of controlling grasses and weeds according to the invention can be used, are typically cereals (in particular wheat, barley, rye or triticale; preferably wheat or barley), rice, corn (i.e. maize), rape, sugarbeet, sugarcane, soybean, cotton, sunflower, peanut, or plantation crops. Alternatively, the crops of useful plants can be oats (e.g. *Avena sativa*, the common oat). The crops of useful plants are preferably cereals (e.g. wheat, barley, rye or triticale), rice, corn or soybean; or more preferably are wheat, barley, rice, corn or soybean; or most preferably are rice.

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®.

The weeds to be controlled may be monocotyledonous and/or dicotyledonous weeds, such as, for example, *Stellaria, Nasturtium, Agrostis, Digitaria* (e.g. *Digitaria sanguinalis* (DIGSA)), *Avena* (e.g. *Avena* species other than *Avena sativa* (the common oat); preferably *Avena fatua* (AVEFA), also known as the common wild oat), *Setaria* (e.g. *Setaria faberi* (SETFA)), *Sinapis, Lolium* (e.g. *Lolium perenne* (LOLPE)), *Solanum, Echinochloa* (e.g. *Echinochloa crus-galli* (ECHCG)), *Scirpus, Monochoria, Sagittaria, Bromus, Alopecurus* (e.g. *Alopecurus myosuroides* (ALOMY)), *Sor-* ghum, *Rottboellia, Cyperus, Abutilon, Sida, Xanthium, Amaranthus, Chenopodium, Ipomoea, Chrysanthemum, Galium, Viola* and/or *Veronica*. The weeds to be controlled may alternatively be *Phalaris, Apera, Leptochloa, Geranium, Beta, Brassica, Kochia, Poa, Sinapis, Polygonum, Brachiaria, Eriochloa, Bidens, Euphorbia*, and/or *Panicum*.

Control of monocotyledonous weeds (e.g. weedy grasses) is preferred; in particular *Agrostis, Avena* (e.g. *Avena* species other than *Avena sativa* (the common oat); preferably *Avena fatua* (AVEFA), also known as the common wild oat), *Setaria* (e.g. *Setaria faberi* (SETFA)), *Lolium* (e.g. *Lolium perenne* (LOLPE)), *Echinochloa* (e.g. *Echinochloa crus-galli* (ECHCG)), *Bromus, Alopecurus* (e.g. *Alopecurus myosuroides* (ALOMY)), and/or *Sorghum*. Alternatively, the monocotyledonous weeds to be controlled are, in particular, *Phalaris, Apera, Panicum, Digitaria, Brachiaria, Poa, Eriochloa, Rottboellia*, and/or *Leptochloa*; and/or can be volunteer (non-crop) cereals and/or volunteer (non-crop) maize. The monocotyledonous weeds, to be controlled by compound of formula I, can be either sensitive to or partially or wholly resistant to one or more herbicides, not being a compound of formula I, which are already approved and commercially-available for herbicidal use (and/or which are already used in agriculture as herbicides).

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with further herbicides. Preferably, in these mixtures, the compound of the formula I is one of those compounds listed in Tables 1 to 54 and/or in Table A1 hereinbelow. The following mixtures of the compound of formula I may be important:
compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS RN 335104-84-2), compound of formula I+topramezone (CAS RN 210631-68-8), compound of formula I+4-hydroxy-3-[[2-[(2-methoxyethoxy)methyl]-6-(trifluoro-methyl)-3-pyridinyl]carbonyl]-bicyclo[3.2.1] oct-3-en-2-one (CAS RN 352010-68-5), and compound of formula I+4-hydroxy-3-[[2-(3-methoxypropyl)-6-(difluoromethyl)-3-pyridinyl]carbonyl]-bicyclo[3.2.1]oct-3-en-2-one.

The following alternative mixtures of the compound of formula I may be important (preferably, in these mixtures, the compound of the formula I is one of those compounds listed in Tables 1 to 54 and/or in Table A1 hereinbelow):
compound of formula I+one of the herbicidal compounds disclosed in WO2010/059676 (Dow, e.g. for use with cereal crops, e.g. can be plus cloquintocet-mexyl),
compound of formula I+one of the herbicidal compounds disclosed in WO2010/059680 (Dow, e.g. for use with cereal crops, e.g. can be plus a safener other than cloquintocet-mexyl), and
compound of formula I+one of the herbicidal compounds disclosed in WO2010/059671 (Dow, e.g. for use with rice crops, e.g. can be plus a safener).

The mixing partners for the compound of formula I may also be in the form of esters or salts, as mentioned e.g. in The Pesticide Manual, 12th Edition (BCPC) 2000.

The compounds of formula I according to the invention can also be used in combination with safeners. Preferably, in these mixtures, the compound of the formula I is one of those compounds listed in Tables 1 to 54 below. The following mixtures with safeners, especially, come into consideration: compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+diciclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecopropand compound of the formula I+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

Benoxacor, cloquintocet-mexyl, cyprosulfamide, mefenpyr-diethyl and N-(2-methoxybenzoyl)-4-[(methylaminocarbonyl)amino]benzenesulfonamide are especially preferred safeners. Cloquintocet-mexyl is particularly valuable and is the most preferred safener.

Therefore, the invention also provides a herbicidal composition, which comprises a herbicidally effective amount of a compound of formula I as defined herein, and optionally (or preferably) a further herbicide as mixture partner for the compound of formula I, or optionally (or preferably) a safener, or both.

The invention also provides a herbicidal composition, which comprises a herbicidally effective amount of a compound of formula I as defined herein, a safener, and optionally (or preferably) a further herbicide as mixture partner for the compound of formula I,
wherein the safener is benoxacor, cloquintocet-mexyl, cyprosulfamide, mefenpyr-diethyl or N-(2-methoxybenzoyl)-4-[(methylaminocarbonyl)amino]benzenesulfonamide.

The rate of application of safener, relative to the herbicide (e.g. the compound of formula I), is largely dependent upon the mode of application. In the case of field treatment:
a) generally from 0.001 to 5.0 kg of safener/ha, preferably from 0.001 to 0.5 kg of safener/ha, more preferably 2 to 100g of safener/ha (in particular at 2.5, 5, 7.5, 10, 20 or 50g of safener/ha); and
b) generally from 0.001 to 2 kg of herbicide/ha, but preferably from 0.005 to 1 kg of herbicide/ha, more preferably 5 to 500g of herbicide/ha, and most preferably at 10 to 250 g of herbicide/ha (in particular at 10, 15, 16, 20, 30, 50, 60, 62.5, 100, 125 or 250g of herbicide/ha);
are applied.

The safener and the herbicide (e.g. the compound of formula I) can for example be used (e.g. when together in a mixture formulation) at a herbicide:safener ratio of from 16:1 to 1:1, such as 8:1, 4:1 or 2:1, measured on the basis of the rates of application of herbicide and safener in g I ha; in particular where the safener is cloquintocet-mexyl.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. In the case of seed dressing, generally from 0.001 to 10g of safener/kg of seed, preferably from 0.05 to 2g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

It is preferred to apply the mixture partner of the compound of formula I together with one of the safeners mentioned above.

The following Examples illustrate the invention further but do not limit the invention.

PREPARATION EXAMPLES

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds shown below, and in Table A1 are drawn as an arbitrary single enol tautomer, but it should be inferred that this description covers both the diketone form and any possible enols which could arise through tautomerism. Where more than one tautomer is observed in proton NMR, the data shown are for the mixture of tautomers. Furthermore, some of the compounds shown below are drawn as single enantiomers for the purposes of simplicity, but unless specified as single enantiomers, these structures should be construed as representing a mixture of enantiomers. Additionally, some of the compounds can exist as diastereoisomers, and it should be inferred that these can be present as a mixture of diastereoisomers or as any possible single diastereoisomer.

Example 1

Preparation of 2-[3-(4-chloro-phenyl)-5-methyl-pyrazol-1-yl]-4-[1-(tetrahydro-pyran-4-yl)-meth-(E)-ylidene]-cyclopentane-1,3-dione

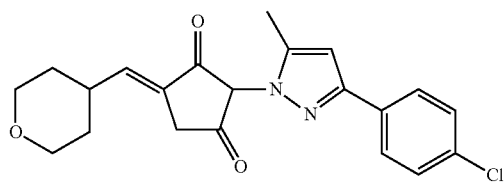 [SMILES: Cc1cc(-c2ccc(Cl)cc2)nn1C1C(=O)C/C(=C\C2CCOCC2)C1=O]

Step 1

Preparation of 5-bromo-4-oxo-pentanoic acid methyl ester

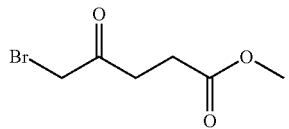

30 ml of trimethylsilyldiazomethane (2 M solution in diethyl ether) was added drop wise to a solution of 3-carbomethoxy propionylchloride (3.75 g, 30.5 mmol) in acetonitrile (75 ml) over a period of 10 mins at room temperature. The mixture was then stirred for 1 h. The reaction was cooled to 0° C. and 10g of 33% HBr in acetic acid was added slowly over 20 min, then the reaction was warmed to room temperature and stirred for 16 h. The solvent was removed in vacuo without heating and the residue was dissolved in ethyl acetate (100 ml), washed with 50 ml of saturated sodium bicarbonate solution and then 50 ml of brine. The organics were passed through a phase separator to remove any water and the solvent removed in vacuo. The resultant crude material was purified by kuglerhor distillation under reduced pressure (~3 mbar, 150° C.) to give 5-bromo-4-oxo-pentanoic acid methyl ester (7g).

Step 2:

Preparation of 5-[3-(4-chloro-phenyl)-5-methyl-pyrazol-1-yl]-4-oxo-pentanoic acid methyl ester

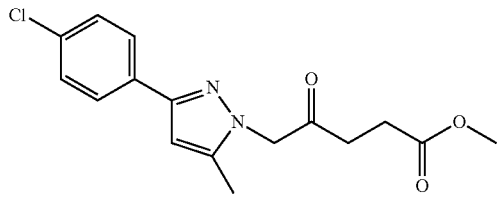 [SMILES: COC(=O)CCC(=O)Cn1nc(-c2ccc(Cl)cc2)cc1C]

3-(4-Chloro-phenyl)-5-methyl-1H-pyrazole (1.84 g, 9.6 mmol) was dissolved in dimethylformamide (20 ml) followed by the addition of sodium hydride (60% dispersion in oil, 384 mg, 9.6 mmol). The reaction was stirred at room temperature for 15 min, followed by the addition of 5-bromo-4-oxo-pentanoic acid methyl ester (2 g, 9.6 mmol). The reaction was stirred at room temperature for a further 30 min, before the addition of water (200 ml). The solution was then extracted with ethyl acetate (2×150 ml). The organics were dried over magnesium sulfate and concentrated in vacuo. The crude product was then purified by column chromatography (120g column, DCM to 90% DCM/EtOAc over 50 mins) to give 5-[3-(4-chloro-phenyl)-5-methyl-pyrazol-1-yl]-4-oxo-pentanoic acid methyl ester (1.84 g).

Step 3

Preparation of 2-[3-(4-Chloro-phenyl)-5-methyl-pyrazol-1-yl]-cyclopentane-1,3-dione

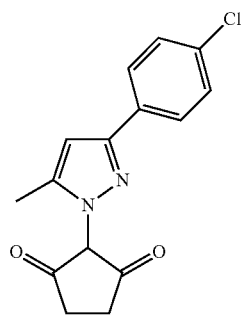 [SMILES: Cc1cc(-c2ccc(Cl)cc2)nn1C1C(=O)CCC1=O]

5-[3-(4-chloro-phenyl)-5-methyl-pyrazol-1-yl]-4-oxo-pentanoic acid methyl ester (1.7 g, 5.5 mmol) was dissolved in dimethylformamide (16 ml) and anhydrous potassium carbonate (3 g, 22 mmol) added. The mixture was then heated to 200° C. for 10 mins in the microwave (using "normal" absorbtion). The reaction was reduced in vacuo, and partitioned between 2 M hydrochloric acid (50 ml) and dichloromethane (100 ml). The layers were separated, and the aqueous layer saturated with sodium chloride and extracted with dichloromethane (100 ml). The organics were combined, dried over magnesium sulfate and the solvent removed in vacuo. The reaction was then purified by column chromatography (using DCM:EtOAc:AcOH (9:1:0.01%) to (3:7:0.01%)) to give 2-[3-(4-chloro-phenyl)-5-methyl-pyrazol-1-yl]-cyclopentane-1,3-dione (0.8 g).

Step 4

Preparation of 2-[3-(4-Chloro-phenyl)-5-methyl-pyrazol-1-yl]-3-methoxy-cyclopent-2-enone

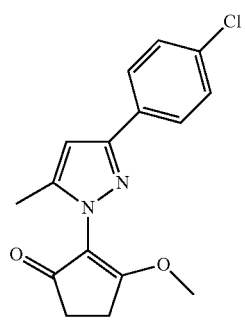 [SMILES: COC1=C(n2nc(-c3ccc(Cl)cc3)cc2C)C(=O)CC1]

Neat dimethyl sulfate (0.12 ml, 1.3 mmol) was added at room temperature to a vigorously stirred suspension of 2-[3-(4-chloro-phenyl)-5-methyl-pyrazol-1-yl]-cyclopentane-1,3-dione (374 mg, 1.3 mmol) and potassium carbonate (180 mg, 1.3 mmol) in acetone (10 ml). The mixture was then heated to 60° C. for 3 h with continued stirring, then cooled and the solvent removed in vacuo. The residue was partitioned between ethyl acetate (30 ml) and 1M sodium hydroxide solution (20 ml), the layers were separated, and the aqueous phase was further extracted with ethyl acetate (2×20 ml). The combined organics were washed with brine (20 ml), dried over magnesium sulfate and concentrated. The crude product was then purified by flash chromatography (using 20% to 100% EtOAc in DCM) to give 2-[3-(4-chloro-phenyl)-5-methyl-pyrazol-1-yl]-3-methoxy-cyclopent-2-enone (253.2 mg).

Step 5

Preparation of 2-[3-(4-chloro-phenyl)-5-methyl-pyrazol-1-yl]-4-[1-(tetrahydro-pyran-4-yl)-meth-(E)-ylidene]-cyclopentane-1,3-dione

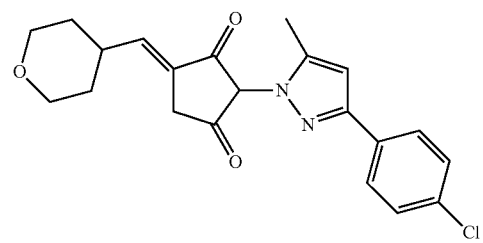 [SMILES: Cc1cc(-c2ccc(Cl)cc2)nn1C1C(=O)C/C(=C\C2CCOCC2)C1=O]

A solution of lithium diisopropylamide (1.8 M in tetrahydrofuran/heptane/ethylbenzene, 0.25 ml, 0.45 mmol) was added drop wise to a solution of 2-[3-(4-chloro-phenyl)-5-methyl-pyrazol-1-yl]-3-methoxy-cyclopent-2-enone (124 mg, 0.41 mmol) in anhydrous tetrahydrofuran (1 ml) at −78° C., under nitrogen, and allowed to stir at this temperature for 30 minutes. Tetrahydropyranyl-4-carbaldehyde (51.5 mg, 0.45 mmol) was added drop wise and the reaction stirred at −78° C. for a further 30 minutes. The reaction was allowed to warm to room temperature over 30 mins and quenched by the addition of 1 M hydrochloric acid (5 ml) and extracted with dichlormethane (3×10 ml) to give 223.5 mg of crude material. The crude material was dissolved in acetone (2 ml) and 2 M hydrochloric acid (2 ml) added. This solution was heated in the microwave (using "normal" absorbtion) for 1 h at 120° C. This solution was extracted with dichloromethane (2×10 ml) and the organics dried over magnesium sulfate and reduced in vacuo. The crude material was purified by reverse phase preparative HPLC (eluting with acetonitrile/water) to give 2-[3-(4-chloro-phenyl)-5-methyl-pyrazol-1-yl]-4-(tetrahydro-pyran-4-ylmethyl)-cyclopentane-1,3-dione (32.2 mg).

Preparation of 2-[3-(4-chloro-phenyl)-5-methyl-pyrazol-1-yl]-4-(tetrahydro-pyran-4-ylmethyl)-cyclopentane-1,3-dione

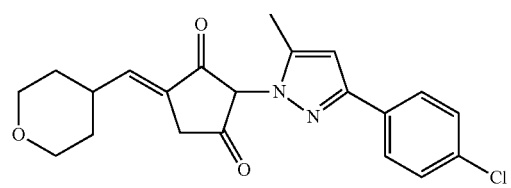 [SMILES: Cc1cc(-c2ccc(Cl)cc2)nn1C1C(=O)C/C(=C\C2CCOCC2)C1=O]

To a solution of 2-[3-(4-chloro-phenyl)-5-methyl-pyrazol-1-yl]-4-[1-(tetrahydro-pyran-4-yl)-meth-(E)-ylidene]-cyclopentane-1,3-dione (9 mg, 0.02 mmol) in methanol (0.1 ml) was added 5% palladium on activated charcoal (1 mg) and the reaction stirred for 6 hours under 1.5 bar of hydrogen. The solution was then filtered through a pad of Celite, washed with methanol (10 ml) and concentrated in vacuo to give a white solid, which was purified by reverse phase preparative HPLC (eluting with acetonitrile/water) to give 2-[3-(4-chloro-phenyl)-5-methyl-pyrazol-1-yl ]-4-(tetrahydro-pyran-4-ylmethyl)-cyclopentane-1,3-dione (4 mg).

Preparation of 2-[3-(4-chloro-phenyl)-5-methyl-pyrazol-1-yl]-4-[1-(5-fluoro-pyridin-2-yl)-meth-(Z)-ylidene]-cyclopentane-1,3-dione and 2-[3-(4-chloro-phenyl)-5-methyl-pyrazol-1-yl]-4-[1-(5-fluoro-pyridin-2-yl)-meth-(E)-ylidene]-cyclopentane-1,3-dione

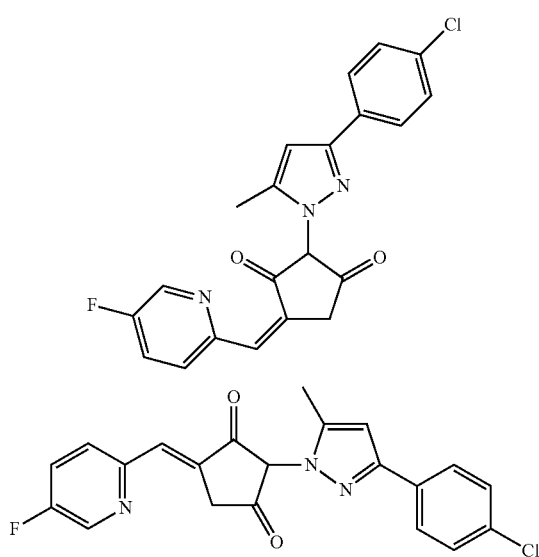

A solution of lithium diisopropylamide (1.8 M in tetrahydrofuran/heptane/ethylbenzene, 0.25 ml, 0.45 mmol) was added drop wise to a solution of 2-[3-(4-chloro-phenyl)-5-methyl-pyrazol-1-yl]-3-methoxy-cyclopent-2-enone (124 mg, 0.41 mmol) in anhydrous tetrahydrofuran (1 ml) at −78° C., under nitrogen, and allowed to stir at this temperature for 30 minutes. 5-Fluoro-pyridine-2-carbaldehyde (56 mg, 0.45 mmol) was then added drop wise and the reaction stirred at −78° C. for a further 30 minutes. The reaction was then allowed to warm to room temperature over 30 mins and quenched by the addition of 1 M hydrochloric acid (5 ml) and extracted with dichlormethane (3×10 ml) to give 186 mg of crude material. The crude material was dissolved in acetone (2 ml) and 2 M hydrochloric acid (2 ml) added. This solution was heated in the microwave (using "normal" absorbtion) for 1 h at 120° C. This solution was extracted with dichloromethane (2×10 ml) and the organics dried over magnesium sulfate and reduced in vacuo. The crude material was purified by reverse phase preparative HPLC (eluting with acetonitrile/water) to give 2-[3-(4-chloro-phenyl)-5-methyl-pyrazol-1-yl]-4-[1-(5-fluoro-pyridin-2-yl)-meth-(Z)-ylidene]-cyclopentane-1,3-dione (22 mg) and 2-[3-(4-chloro-phenyl)-5-methyl-pyrazol-1-yl]-4-[1-(5-fluoro-pyridin-2-yl)-meth-(E)-ylidene]-cyclopentane-1,3-dione (5 mg).

Preparation of 2-[3-(4-chloro-phenyl)-5-methyl-pyrazol-1-yl]-4-(5-fluoro-pyridin-2-ylmethyl)-cyclopentane-1,3-dione

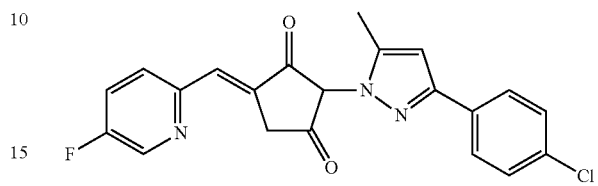

To a solution of 2-[3-(4-chloro-phenyl)-5-methyl-pyrazol-1-yl]-4-[1-(5-fluoro-pyridin-2-yl)-meth-(Z)-ylidene]-cyclopentane-1,3-dione (17 mg, 0.04 mmol) in methanol (0.4 ml) was added 5% palladium on activated charcoal (2 mg) and the reaction stirred for 6 hours under 1.5 bar of hydrogen. The solution was then filtered through a pad of Celite, washed with methanol (10 ml) and concentrated in vacuo to give a white solid, which was purified by column chromatography using DCM:EtOAc:AcOH (9:1:0.01%) to (3:7:0.01%) to give 2-[3-(4-chloro-phenyl)-5-methyl-pyrazol-1-yl]-4-(5-fluoro-pyridin-2-ylmethyl)-cyclopentane-1,3-dione (15.7 mg).

Preparation of 2-(1,5-Dimethyl-1H-indazol-4-yl)-4-(tetrahydro-pyran-4-ylmethyl)-cyclopentane-1,3-dione

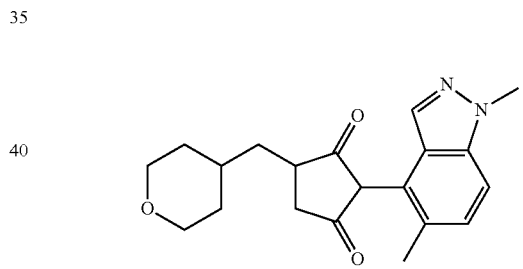

Step 1

Preparation of 5-[hydroxy-(tetrahydro-pyran-4-yl)-methyl]-3-methoxy-cyclopent-2-enone

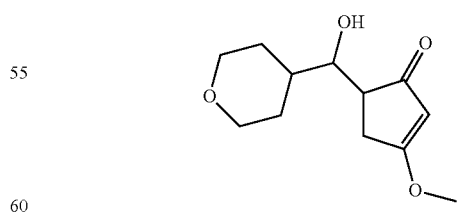

A solution of 3-methoxy-cyclopent-2-enone (18.8 g, 0.17 mol) in THF (200 ml) was added drop wise over 30 minutes (using an addition funnel) to a solution of lithium diisopropylamide solution (1.8 M in tetrahydrofuran/heptane/ethylbenzene, 103 ml, 0.18 mol) in THF (150 ml) at −78° C., under nitrogen and allowed to stir at this temperature for 30 minutes.

Tetrahydropyranyl-4-carbaldehyde (21 g, 0.18 mol) was then added drop wise and the reaction stirred at −78° C. for 30 minutes, before being allowed to warm to room temperature overnight (18 h). The reaction was then quenched by the addition of 1 M hydrochloric acid (500 ml) and extracted with ethyl acetate (3×500 ml). The aqueous layer was then saturated with sodium chloride and extracted with ethyl acetate (2×250 ml). The combined organics were evaporated and the crude product was purified using column chromatography (EtOAc:hexane, 3:7 to 100% EtOAc) to give 5-[hydroxy-(tetrahydro-pyran-4-yl)-methyl]-3-methoxy-cyclopent-2-enone (20.8 g).

Step 2

Preparation of 3-methoxy-5-[1-(tetrahydro-pyran-4-yl)-methylidene]-cyclopent-2-enone

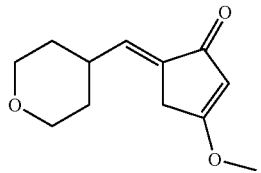

5-[hydroxy-(tetrahydro-pyran-4-yl)-methyl]-3-methoxy-cyclopent-2-enone (1.1 g, 5 mmol) was dissolved in dichloromethane (25 ml) in a 50 ml round bottom flask fitted with a reflux condenser. Triethylamine (1.4 ml, 10 mmol) and then methane sulfonyl chloride (0.8 ml, 10 mmol) was added dropwise which caused the reaction to warm to reflux. After 10 minutes the reaction was quenched by the addition of 1 M hydrochloric acid (10 ml). The layers were separated and the organics collected, passed through a phase separation cartridge and the solvent removed in vacuo. The crude product was dissolved in methanol (25 ml) and anhydrous potassium carbonate (1.4 g, 10 mmol) added and the mixture was stirred at room temperature for 72 h. The solvent was then removed in vacuo and the residue dissolved in ethyl acetate (25 ml) and filtered to remove any solid. The filtrate was evaporated to dryness and the residue purified on by column chromatography (Hexane/EtOAc (7:3) to 100% EtOAc) to give 3-methoxy-5-[1-(tetrahydro-pyran-4-yl)-methylidene]-cyclopent-2-enone (938 mg).

Step 3

Preparation of 3-methoxy-5-(tetrahydro-pyran-4-ylmethyl)-cyclopent-2-enone

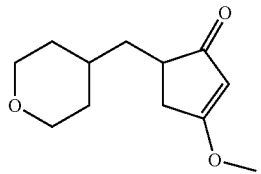

A solution of 3-methoxy-5-[1-(tetrahydro-pyran-4-yl)-methylidene]-cyclopent-2-enone (938 mg, 4.5 mmol) in ethanol (45 ml) was added to 5% palladium on activated charcoal (94 mg) and the reaction stirred for 7.5 hours under 3 bar of hydrogen. The reaction was then filtered through a pad of Celite, washed with ethanol and concentrated in vacuo to give 3-methoxy-5-(tetrahydro-pyran-4-ylmethyl)-cyclopent-2-enone (906 mg).

Step 4

Preparation of 2-bromo-3-methoxy-5-(tetrahydro-pyran-4-ylmethyl)-cyclopent-2-enone

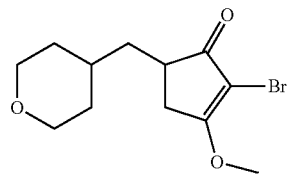 [SMILES: COC1=C(Br)C(=O)C(CC2CCOCC2)C1]

To a stirred solution of 3-methoxy-5-(tetrahydro-pyran-4-ylmethyl)-cyclopent-2-enone (906 mg, 4.7 mmol) in 1,2-dichloroethane (15 ml) at 0° C. in an amber flask was added portion wise over one hour N-bromosuccinimide (890 mg, 5 mmol). The reaction was stirred at 0° C. for a further 90 minutes and then any remaining solid was removed by filtration. The filtrate was evaporated to dryness under reduced pressure, the resultant solid dissolved in warm toluene (50 ml) and washed quickly with ice-cold water (2×20 ml). The organic phase was dried over magnesium sulfate and the solvent evaporated in vacuo. The residue was purified using column chromatography (40% to 80% EtOAc in hexane) to give 2-bromo-3-methoxy-5-(tetrahydro-pyran-4-ylmethyl)-cyclopent-2-enone (1.1 g).

Step 5

Preparation of 2-(1,5-dimethyl-1H-indazol-4-yl)-4-(tetrahydro-pyran-4-ylmethyl)-cyclopentane-1,3-dione

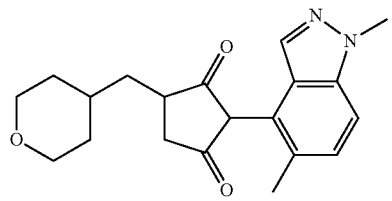 [SMILES: Cc1ccc2c(cnn2C)c1C1C(=O)CC(CC2CCOCC2)C1=O]

To a stirred suspension of the 2-bromo-3-methoxy-5-(tetrahydro-pyran-4-ylmethyl)-cyclopent-2-enone (150 mg, 0.5 mmol), 1,5-dimethyl-1H-indazole-4-boronic acid (148 mg, 0.78 mmol) and freshly powdered potassium phosphate tribasic (221 mg, 1 mmol) in anhydrous, de-gassed toluene (1.5 ml) under a nitrogen atmosphere were added palladium acetate (6 mg, 0.03 mmol) and 2-dicyclohexylphosphino-2′,6′-dimethoxybiphenyl (21 mg, 0.05 mmol). The reaction was heated to 140° C. for 30 minutes in the microwave (using "normal" absorbtion). The reaction was diluted with water (10 ml) and extracted with ethyl acetate (3×15 ml). The combined organic extracts were washed with brine (10 ml), dried over magnesium sulfate and evaporated to dryness under reduced pressure to give a brown oil. The crude product was purified by column chromatography (30% EtOAc/hexane to 100% EtOAc as eluent) to give 2-(1,5-Dimethyl-1H-indazol-4-yl)-3-methoxy-5-(tetrahydro-pyran-4-ylmethyl)-cyclopent-2-enone (41 mg). This material was dissolved in acetone (2 ml) and 2 M hydrochloric acid (2 ml) added. This solution was heated in the microwave (using "normal" absorbtion) for 1 h at 120° C. This solution was then extracted with dichloromethane (2×10 ml) and the organics dried over magnesium sulfate and reduced in vacuo. The crude material was purified by reverse phase preparative HPLC (eluting with acetonitrile/water) to give 2-(1,5-dimethyl-1H-indazol-4-yl)-4-(tetrahydro-pyran-4-ylmethyl)-cyclopentane-1,3-dione (4 mg).

Example 2

Preparation of 2-[2-(4-Chloro-phenyl)-5-methyl-pyrimidin-4-yl]-4-(tetrahydro-pyran-4-ylmethyl)-cyclopentane-1,3-dione

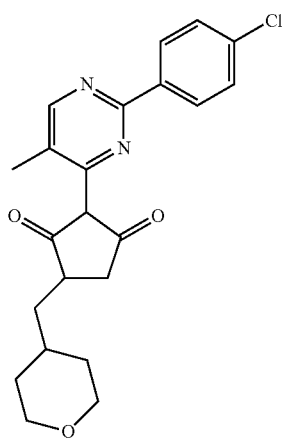 [SMILES: Cc1cnc(-c2ccc(Cl)cc2)nc1C1C(=O)CC(CC2CCOCC2)C1=O]

Step 1

Preparation of 2-(4-Chloro-phenyl)-5-methyl-3H-pyrimidin-4-one

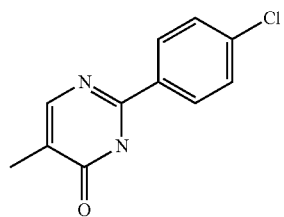

Sodium metal (276 mg, 12 mmol) was added portion wise to ethanol (15 ml) under a nitrogen atmosphere and the mixture allowed to stir at room temperature for 30 minutes until the reaction became homogeneous. 4-Chloro-benzamidine (hydroiodide salt) (1.41 g, 5 mmol) was then added in one portion and the reaction stirred at room temperature for a further 60 minutes. 2-Methyl-3-oxo-propionic acid ethyl ester (716 mg, 5.5 mmol) was finally added drop wise. The reaction was left to stir at room temperature overnight before quenching the reaction slowly with 2M Hydrochloric acid until reaction pH measured pH 1. The resulting precipitate was filtered and air dried, to give 2-(4-Chloro-phenyl)-5-methyl-3H-pyrimidin-4-one as a white solid (570 mg, 2.58 mmol, 52% yield).

Step 2

Preparation of 6-Chloro-2-(4-chloro-phenyl)-5-methyl-1,6-dihydro-pyrimidine

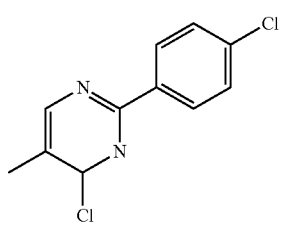

2-(4-Chloro-phenyl)-5-methyl-3H-pyrimidin-4-one (570 mg, 2.58 mmol) was suspended in phosphorus oxychloride (2 ml) and heated to reflux for 2 hours. The mixture was cooled before being stripped to dryness in vacuo. The resulting crude product was solubilised in water (10 ml) and ethyl acetate (10 ml) and the biphasic mixture separated. The aqueous layer was further extracted with ethyl acetate (10 ml) before the combined organics were dried with magnesium sulphate, filtered and stripped to dryness in vacuo to give 6-Chloro-2-(4-chloro-phenyl)-5-methyl-1,6-dihydro-pyrimidine as a white solid (567 mg, 2.38 mmol, 92% yield).

Step 3

Preparation of 2-[2-(4-Chloro-phenyl)-5-methyl-pyrimidin-4-yl]-cyclopentane-1,3-dione

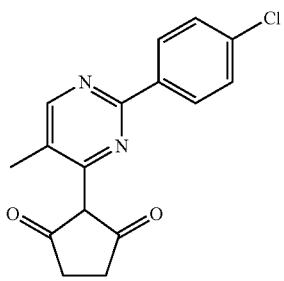 [SMILES: Cc1cnc(-c2ccc(Cl)cc2)nc1C1C(=O)CCC1=O]

To a microwave vial was added 1,3-cyclopentadione (0.5 g, 5.1 mmol), 6-Chloro-2-(4-chloro-phenyl)-5-methyl-1,6-dihydro-pyrimidine (1.04 g, 4.3 mmol), palladium acetate (58 mg, 0.26 mmol), 2-Dicyclohexylphosphino-2',4',6'-triisopropylbiphenyl (183 mg, 0.38 mmol), potassium phosphate tribasic (2.49 g, 11.7 mmol) and 1,4-dioxane (10 ml). This was heated in the microwave for 30 minutes at 150° C. on a normal setting with a pre-stir of 25 seconds. The resulting slurry was diluted with ethyl acetate (10 ml) and 2M hydrochloric acid (10 ml) before filtering through celite. The filter cake was washed with further ethyl acetate (10 ml) and 2M hydrochloric acid (10 ml). The resulting biphasic mixture was separated and the aqueous layer was extracted with further ethyl acetate (2×10 ml). The combined organic layers were then dried with magnesium sulphate, filtered and stripped to dryness to yield a dark yellow solid. This was purified by normal phase chromatography (gradient system of 100% dichloromethane–5% methanol:dichloromethane) to give 2-[2-(4-Chloro-phenyl)-5-methyl-pyrimidin-4-yl]-cyclopentane-1,3-dione as a yellow solid (348 mg, 1.16 mmol, 22% yield).

Step 4

Preparation of 2-[2-(4-Chloro-phenyl)-5-methyl-pyrimidin-4-yl]-3-methoxy-cyclopent-2-enone

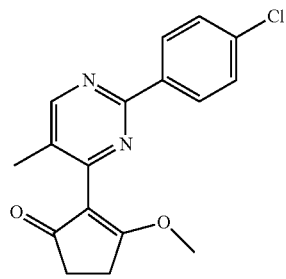 [SMILES: COC1=C(c2nc(-c3ccc(Cl)cc3)ncc2C)C(=O)CC1]

2-[2-(4-Chloro-phenyl)-5-methyl-pyrimidin-4-yl]-cyclopentane-1,3-dione (650 mg, 2.16 mmol) was slurried in acetone (20 ml) and potassium carbonate (300 mg, 2.16 mmol) was added. After stirring at room temperature for 5 minutes, dimethyl sulphate (0.20 ml, 2.16 ml) was added in one portion and the reaction was heated to reflux. After 3 hours at reflux the reaction was complete and subsequently cooled to room temperature, before stripping to dryness. The resulting orange solid was re-solubilised in ethyl acetate (20 ml) and 1M sodium hydroxide (20 ml) and the biphasic mixture separated. The aqueous layer was further extracted with ethyl acetate (2×10 ml) before combining the organic layers, drying over magnesium sulphate, filtering and stripping to dryness to isolate a brown solid. This was purified by normal phase chromatography (gradient system of 100% dichloromethane–5% methanol:dichloromethane) to isolate 2-[2-(4-Chloro-phenyl)-5-methyl-pyrimidin-4-yl]-3-methoxy-cyclopent-2-enone as a yellow foam (526 mg, 1.67 mmol, 77% yield).

Step 5

Preparation of 2-[2-(4-Chloro-phenyl)-5-methyl-pyrimidin-4-yl]-5-[hydroxy-(tetrahydro-pyran-4-yl)-methyl]-3-methoxy-cyclopent-2-enone

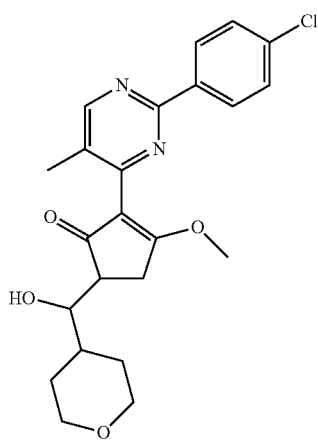 [SMILES: COC1=C(c2nc(-c3ccc(Cl)cc3)ncc2C)C(=O)C(C(O)C2CCOCC2)C1]

A solution of 2-[2-(4-Chloro-phenyl)-5-methyl-pyrimidin-4-yl]-3-methoxy-cyclopent-2-enone (69.5 mg, 0.22 mmol) in anhydrous tetrahydrofuran (3 ml), under nitrogen, was cooled to −78° C. and stirred for 10 minutes before the drop wise addition of lithium diisopropylamide (as a 2.0M solution in hexane/tetrahydrofuran/ethylbenzene) (0.14 ml, 0.28 mmol). The resulting brown solution was stirred at −78° C. for a further 45 minutes before the drop wise addition of 4-formyltetrahydropyran (34 mg, 0.30 mmol). The orange solution was then warmed to room temperature. After 2.5 h the reaction was shown to have reached a steady state and was therefore quenched with saturated ammonium chloride (5 ml), ethyl acetate (5 ml) and water (1 ml). The biphasic mixture was separated and the aqueous layer further extracted with ethyl acetate (2×5 ml). Combined organics were dried over magnesium sulphate, filtered and stripped to dryness to yield a yellow oil. This was purified by normal phase chromatography (100% dichloromethane–5% methanol:dichloromethane) to give 2-[2(4-Chloro-phenyl)-5-methyl-pyrimidin-4-yl]-5-[hydroxy-(tetrahydro-pyran-4-yl)-methyl]-3-methoxy-cyclopent-2-enone as a dark yellow oil (50.3 mg, 0.12 mmol, 53% yield).

Step 6

Preparation of 2-[2-(4-Chloro-phenyl)-5-methyl-pyrimidin-4-yl]-4-[1-(tetrahydro-pyran-4-yl)-methyl-(E)ylidene-cyclopentane-1,3-dione

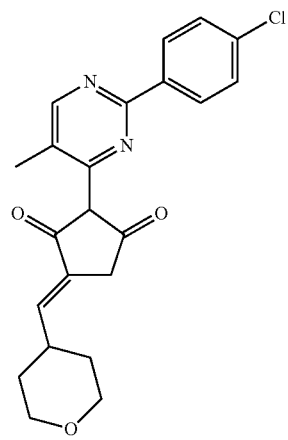 [SMILES: Cc1cnc(-c2ccc(Cl)cc2)nc1C1C(=O)C/C(=C\C2CCOCC2)C1=O]

2-[2-(4-Chloro-phenyl)-5-methyl-pyrimidin-4-yl]-5-[hydroxy-(tetrahydro-pyran-4-yl)-methyl]-3-methoxy-cyclopent-2-enone (50 mg, 0.12 mmol) was solubilised in 1,4-dioxane (2.0 ml) to form a yellow solution. Concentrated hydrochloric acid (20 μl) was then added in one portion and the resulting orange solution was heated to 60° C. It was stirred at this temperature for 6 hours, adding more concentrated hydrochloric acid after 3 hours (20 μl) and 4 hours (20 μl), before reaction completion was seen. Reaction was cooled to room temperature and then stripped to dryness to yield 2-[2-(4-Chloro-phenyl)-5-methyl-pyrimidin-4-yl]-4-[1-(tetrahydro-pyran-4-yl)-meth-(E)-ylidene-cyclopentane-1,3-dione as a dark orange oil (88 mg, 0.22 mmol, 185% yield).

Step 7

Preparation of 2-[2-(4-Chloro-phenyl)-5-methyl-pyrimidin-4-yl]-4-(tetrahydro-pyran-4-ylmethyl)-cyclopentane-1,3-dione

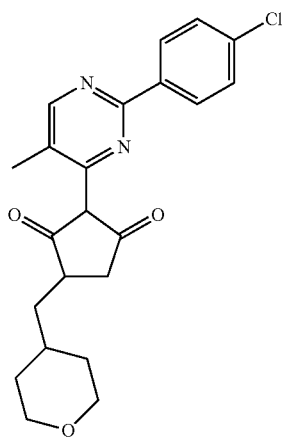 [SMILES: Cc1cnc(-c2ccc(Cl)cc2)nc1C1C(=O)CC(CC2CCOCC2)C1=O]

2-[2-(4-Chloro-phenyl)-5-methyl-pyrimidin-4-yl]-4-[1-(tetrahydro-pyran-4-yl]-meth-(E)-ylidene-cyclopentane-1,3-dione (88 mg, 0.22 mmol) was solubilised in ethanol (2.5 ml) and 5% palladium on activated charcoal (4.4 mg, 5% weight relative to starting material) was added. The reaction was stirred at room temperature under 1.5 bar pressure of hydrogen for 14.5 hours, adding more 5% palladium on activated charcoal (4.4 mg, 5% weight relative to starting material) after 7.5 hours. Reaction was then filtered through celite, washing the filter pad with ethanol (10 ml). The resulting solution was stripped to dryness to yield a yellow oil which was purified by reverse phase preparative HPLC (using water, acetonitrile) to give 2-[2-(4-Chloro-phenyl)-5-methyl-pyrimidin-4-yl]-4-(tetrahydro-pyran-4-ylmethyl)-cyclopentane-1,3-dione as a pale yellow oil (9.8 mg, 0.025 mmol, 11% yield).

Example 3

Preparation of 2-[2-(4-Chloro-phenyl)-5-methyl-thiazol-4-yl]-4-(tetrahydro-pyran-4-ylmethyl)-cyclopentane-1,3-dione

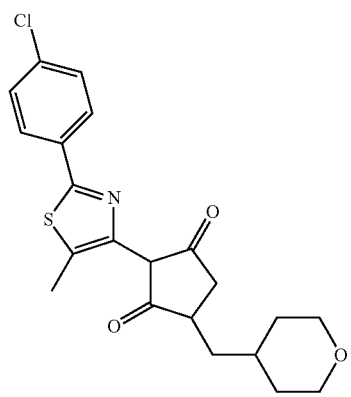 [SMILES: Cc1sc(-c2ccc(Cl)cc2)nc1C1C(=O)CC(CC2CCOCC2)C1=O]

Step 1

Preparation of 2-(4-Chloro-phenyl)-thiazole-5-carbaldehyde

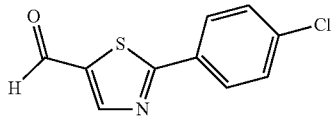 [SMILES: O=Cc1cnc(-c2ccc(Cl)cc2)s1]

To a suspension of 4-chlorophenyl thioamide (10 g, 58.2 mmol) in 1,2-dimethoxyethane (80 ml) was added 2-chloromalonaldehyde (11.3 g, 87.3 mmol), followed by magnesium carbonate hexahydate (14.12 g, 30.8 mmol), and the reaction heated to 60° C. under nitrogen for 3 hours. The crude reaction mixture was filtered through a plug of silica (50g), washed with ethyl acetate, and the combined filtrate concentrated under reduced pressure to give 2-(4-Chloro-phenyl)-thiazole-5-carbaldehyde (7.66 g).

Step 2

Preparation of [2-(4-Chloro-phenyl)-thiazol-5-yl]-methanol

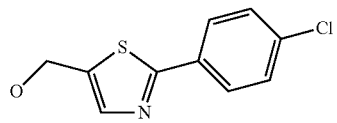 [SMILES: OCc1cnc(-c2ccc(Cl)cc2)s1]

To a solution of 2-(4-Chloro-phenyl)-thiazole-5-carbaldehyde (5.59 g, 25 mmol) in methanol (65 ml) at 0° C. was added sodium borohydride (1.04 g, 27.5 mmol) portionwise over a period of 5 minutes. The reaction was then allowed to warm to room temperature and stirred under nitrogen for 3 hours. The reaction was quenched with saturated aqueous ammonium chloride solution (100 ml) and stirred for 5 minutes, before the methanol was removed under reduced pressure. The resulting heterogeneous mixture was then extracted with ethyl acetate (2×100 ml), the combined organics dried over magnesium sulphate and the solvent removed under reduced pressure to give [2-(4-Chloro-phenyl)-thiazol-5-yl]-methanol (5.27 g).

Step 3

Preparation of 3-[2-(4-Chloro-phenyl)-thiazol-5-ylmethoxy]-cyclopent-2-enone

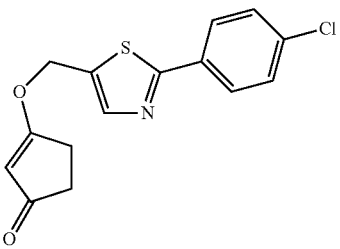 [SMILES: O=C1C=C(OCc2cnc(-c3ccc(Cl)cc3)s2)CC1]

To a solution of [2-(4-Chloro-phenyl)-thiazol-5-yl]-methanol (2 g, 8.8 mmol) in anhydrous THF (50 ml), at 0° C., under an atmosphere of nitrogen was added cyclopentane-1,3-dione (1.12 g, 11.4 mmol), followed by triphenylphosphine (2.99 g, 11.4 mmol). Diisopropylazodicarboxylate (2.2 ml, 11.4 mmol) was then added dropwise over a period of 5 minutes and the reaction allowed to warm to room temperature and stirred for 2 hours. The crude reaction mixture was dry loaded onto silica and purified by flash chromatography to give 3-[2-(4-Chloro-phenyl)-thiazol-5-ylmethoxy]-cyclopent-2-enone (2.12 g).

Step 4

Preparation of 2-[2-(4-Chloro-phenyl)-5-methyl-thiazol-4-yl]-cyclopentane-1,3-dione

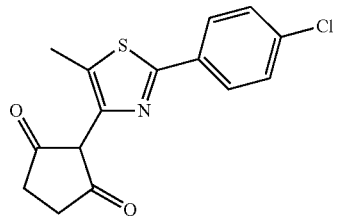 [SMILES: Cc1sc(-c2ccc(Cl)cc2)nc1C1C(=O)CCC1=O]

To a solution of 3-[2-(4-Chloro-phenyl)-thiazol-5-yl-methoxy]-cyclopent-2-enone (1.29 g, 4.22 mmol) in ethylene glycol dimethyl ether (10 ml) was added 1-butyl-3-methylimidazolium bis(trifluoromethylsulphonyl)imide (100 µl) and the reaction heated to 230° C. by microwave irradiation for 30 minutes. The crude reaction mixture was dry loaded onto silica and purified by flash chromatography to give 2-[2-(4-Chloro-phenyl)-5-methyl-thiazol-4-yl]-cyclopentane-1,3-dione (1.12 g).

Step 5

Preparation of 2-[2-(4-Chloro-phenyl)-5-methyl-thiazol-4-yl]-3-methoxy-cyclopent-2-enone

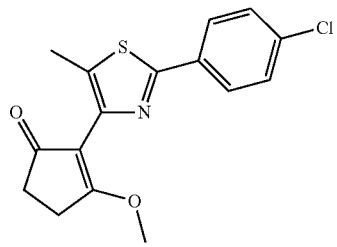 [SMILES: COC1=C(c2nc(-c3ccc(Cl)cc3)sc2C)C(=O)CC1]

To a solution of 2-[2-(4-Chloro-phenyl)-5-methyl-thiazol-4-yl]-cyclopentane-1,3-dione (1.12 g, 3.66 mmol) in acetone (20 ml) was added potassium carbonate (1.04 g, 7.32 mmol), followed by iodomethane (455 µl, 7.32 mmol), and the reaction heated to 40° C. for 6 hours. The solvent was then removed from the crude reaction mixture under reduced pressure and the residue partitioned between water (100 ml) and ethyl acetate (100 ml). The organic layer was separated, dry loaded onto silica and purified by flash chromatography to give 2-[2-(4-Chloro-phenyl)-5-methyl-thiazol-4-yl]-3-methoxy-cyclopent-2-enone (780 mg).

Step 6

Preparation of 2-[2-(4-Chloro-phenyl)-5-methyl-thiazol-4-yl]-3-methoxy-5-[1-(tetrahydro-pyran-4-yl)-meth-(E)-ylidene]-cyclopent-2-enone

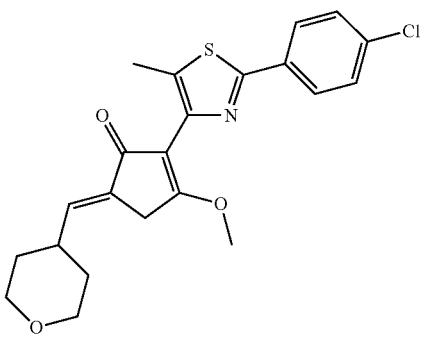 [SMILES: COC1=C(c2nc(-c3ccc(Cl)cc3)sc2C)C(=O)/C(=C/C2CCOCC2)C1]

To a solution of 2-[2-(4-Chloro-phenyl)-5-methyl-thiazol-4-yl]-3-methoxy-cyclopent-2-enone (640 mg, 2 mmol) in anhydrous tetrahydrofuran (12 ml) at −78° C. under an atmosphere of nitrogen was added lithium diisopropylamide (1.8M in THF/heptanes/ethylbenzene; 1.1 ml, 2 mmol) dropwise over a period of 5 minutes, and the reaction allowed to stir at 78° C. for 30 minutes. A solution of tetrahydro-pyran-4-carbaldehyde (228 mg, 2 mmol) in anhydrous tetrahydrofuran (1 ml) was then added dropwise over a period of 5 minutes before the reaction is allowed to warm to room temperature and stirred for a further 30 minutes. Potassium tert-butoxide (337 mg, 3 mmol) was then added in one portion and the reaction stirred for a further 90 minutes. The reaction was quenched by the addition of saturated aqueous ammonium chloride solution (50 ml) and extracted with ethyl acetate (50 ml) and the organic later separated, dry loaded onto silica and purified by flash chromatography to give 2-[2-(4-Chloro-phenyl)-5-methyl-thiazol-4-yl]-3-methoxy-5-[1-(tetrahydro-pyran-4-yl)-meth-(E)-ylidene]-cyclopent-2-enone (195 mg).

Step 7

Preparation of 2-[2-(4-Chloro-phenyl)-5-methyl-thiazol-4-yl]-4-[1-(tetrahydro-pyran-4-yl)-meth-(E)-ylidene]-cyclopentane-1,3-dione

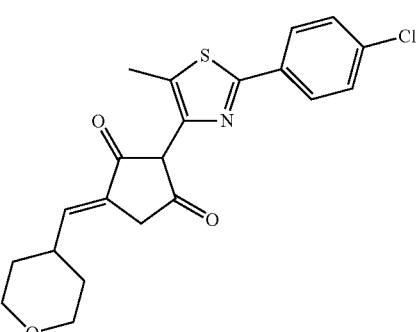

To a solution of 2-[2-(4-Chloro-phenyl)-5-methyl-thiazol-4-yl]-3-methoxy-5-[1-(tetrahydro-pyran-4-yl)-meth-(E)-ylidene]-cyclopent-2-enone (190 mg, 0.45 mmol) in acetone (2 ml) was added 2N hydrochloric acid (2 ml) and the reaction heated to 120° C. for 30 minutes by microwave irradiation. The crude reaction was diluted with ethyl acetate (25 ml) and washed with saturated aqueous ammonium chloride solution (25 ml), brine (25 ml) and the organic later separated, dried over magnesium sulphate and the solvent removed under reduced pressure to give 2-[2-(4-Chloro-phenyl)-5-methyl-thiazol-4-yl]-4-[1-(tetrahydro-pyran-4-yl)-meth-(E)-ylidene]-cyclopentane-1,3-dione (168 mg).

Step 8

Preparation of 2-[2-(4-Chloro-phenyl)-5-methyl-thiazol-4-yl]-4-(tetrahydro-pyran-4-ylmethyl)-cyclopentane-1,3-dione

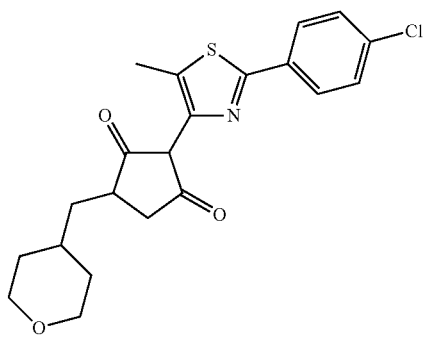 [SMILES: Cc1sc(-c2ccc(Cl)cc2)nc1C1C(=O)CC(CC2CCOCC2)C1=O]

To a solution of 2-[2-(4-Chloro-phenyl)-5-methyl-thiazol-4-yl]-4-[1-(tetrahydro-pyran-4-yl)-meth-(E)-ylidene]-cyclopentane-1,3-dione (130 mg, 0.32 mmol) in ethanol (2 ml) was added 5% palladium on carbon (13 mg), and the reaction stirred under an atmosphere hydrogen at a pressure of 2 bar for 4 hours. The crude reaction mixture was filtered through a pad of Celite and purified by preparative mass-directed HPLC to give 2-[2-(4-Chloro-phenyl)-5-methyl-thiazol-4-yl]-4-(tetrahydro-pyran-4-ylmethyl)-cyclopentane-1,3-dione (30 mg).

Preparation of 2-[2-(4-Chloro-phenyl)-5-methyl-thiazol-4-yl]-4-(5-fluoro-pyridin-2-ylmethyl)-cyclopentane-1,3-dione

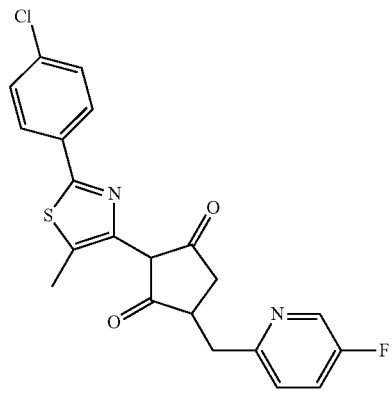 [SMILES: Cc1sc(-c2ccc(Cl)cc2)nc1C1C(=O)CC(Cc2ccc(F)cn2)C1=O]

Step 1

Preparation of 2-[2-(4-Chloro-phenyl)-5-methyl-thiazol-4-yl]-5-[(5-fluoro-pyridin-2-yl)-hydroxy-methyl]-3-methoxy-cyclopent-2-enone

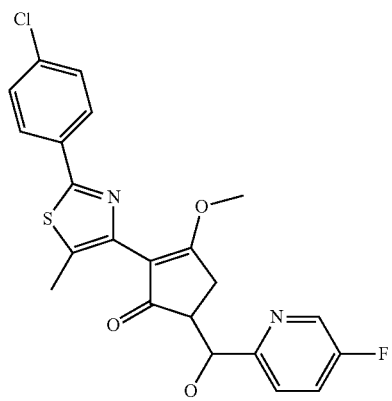 [SMILES: COC1=C(c2nc(-c3ccc(Cl)cc3)sc2C)C(=O)C(C(O)c2ccc(F)cn2)C1]

To a solution of 2-[2-(4-Chloro-phenyl)-5-methyl-thiazol-4-yl]-3-methoxy-cyclopent-2-enone (400 mg, 1.25 mmol) in anhydrous tetrahydrofuran (10 ml) at −78° C. under an atmosphere of nitrogen was added lithium diisopropylamide (1.8M in THF/heptanes/ethylbenzene; 0.76 m, 1.37 mmol) dropwise over a period of 5 minutes, and the reaction allowed to stir at 78° C. for 30 minutes. A solution of 5-fluoro-pyridine-2-carbaldehyde (171 mg, 1.37 mmol) in anhydrous tetrahydrofuran (1 ml) was then added dropwise over a period of 5 minutes before the reaction was allowed to warm to room temperature and stirred for a further 30 minutes. The reaction was quenched by the addition of saturated aqueous ammonium chloride solution (50 ml) and extracted with ethyl acetate (50 ml) and the organic later separated, dry loaded onto silica and purified by flash chromatography to give 2-[2-(4-Chloro-phenyl)-5-methyl-thiazol-4-yl]-5-[(5-fluoro-pyridin-2-yl)-hydroxy-methyl]-3-methoxy-cyclopent-2-enone (400 mg).

Step 2

Preparation of 2-[2-(4-Chloro-phenyl)-5-methyl-thiazol-4-yl]-4-[1-(5-fluoro-pyridin-2-yl)-meth-(E)-ylidene]-cyclopentane-1,3-dione

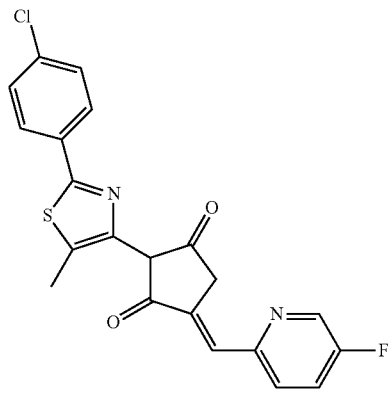 [SMILES: Cc1sc(-c2ccc(Cl)cc2)nc1C1C(=O)C/C(=C\c2ccc(F)cn2)C1=O]

To a solution of 2-[2-(4-Chloro-phenyl)-5-methyl-thiazol-4-yl]-3-methoxy-5-[1-(tetrahydro-pyran-4-yl)-meth-(E)-ylidene]-cyclopent-2-enone (190 mg, 0.45 mmol) in acetone (2 ml) was added 2N hydrochloric acid (2 ml) and the reaction heated to 130° C. for 90 minutes by microwave irradiation. The crude reaction is then dry loaded onto silica and purified by flash chromatography to give 2-[2-(4-Chloro-phenyl)-5-methyl-thiazol-4-yl]-4-[1-(5-fluoro-pyridin-2-yl)-meth-(E)-ylidene]-cyclopentane-1,3-dione (93 mg).
Step 3

Preparation of 2-[2-(4-Chloro-phenyl)-5-methyl-thiazol-4-yl]-4-(5-fluoro-pyridin-2-ylmethyl)-cyclopentane-1,3-dione

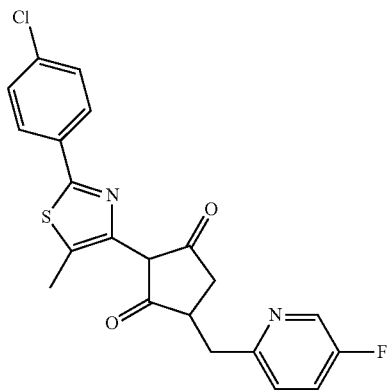 [SMILES: Cc1sc(-c2ccc(Cl)cc2)nc1C1C(=O)CC(Cc2ccc(F)cn2)C1=O]

To a solution of 2-[2-(4-Chloro-phenyl)-5-methyl-thiazol-4-yl]-4-[1-(5-fluoro-pyridin-2-yl)-meth-(E)-ylidene]-cyclopentane-1,3-dione (70 mg, 0.17 mmol) in glacial acetic acid (2 ml) was added zinc powder (10 mg), and the reaction heated to 80° C. for 17 hours. The crude reaction mixture was then dry loaded onto silica and purified by flash chromatography to give 2-[2-(4-Chloro-phenyl)-5-methyl-thiazol-4-yl]-4-(5-fluoro-pyridin-2-ylmethyl)-cyclopentane-1,3-dione (55 mg).

Preparation of 2-[2-(4-Chloro-phenyl)-5-ethyl-thiazol-4-yl]-4-[1-(tetrahydro-pyran-4-yl)-meth-(E)-ylidene]-cyclopentane-1,3-dione

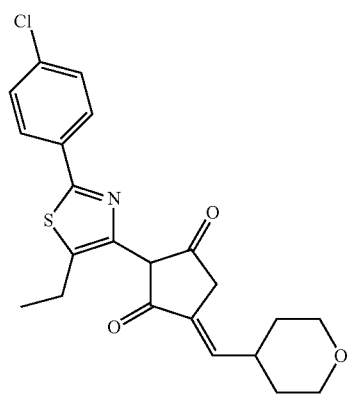 [SMILES: CCc1sc(-c2ccc(Cl)cc2)nc1C1C(=O)C/C(=C\C2CCOCC2)C1=O]

Step 1

Preparation of 2-(4-Chloro-phenyl)-thiazole-5-carbaldehyde

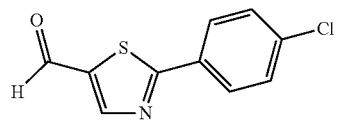 [SMILES: O=Cc1cnc(-c2ccc(Cl)cc2)s1]

To a suspension of 4-chlorophenyl thioamide (10 g, 58.2 mmol) in 1,2-dimethoxyethane (80 ml) was added 2-chloromalonaldehyde (11.3 g, 87.3 mmol), followed by magnesium carbonate hexahydrate (14.12 g, 30.8 mmol), and the reaction heated to 60° C. under an atmosphere of nitrogen for 3 hours. The crude reaction mixture is filtered through a plug of silica (50g), which was washed with ethyl acetate, and the combined filtrate concentrated under reduced pressure to give 2-(4-Chloro-phenyl)-thiazole-5-carbaldehyde (7.66 g).
Step 2

Preparation of 1-[2-(4-Chloro-phenyl)-thiazol-5-yl]-ethanol

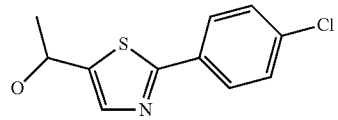

To a solution of 2-(4-Chloro-phenyl)-thiazole-5-carbaldehyde (4.95 g, 22.14 mmol) in THF (65 ml) at 0° C. under an atmosphere of nitrogen was added methyl magnesium chloride (3M in THF; 8.11 ml, 24.35 mmol) dropwise over a period of 5 minutes. The reaction was then allowed to warm to room temperature and stirred for a further 2 hours. The reaction was quenched with saturated aqueous ammonium chloride solution (100 ml) and stirred for 5 minutes, before the methanol is removed under reduced pressure. The resulting heterogeneous mixture was then extracted with ethyl acetate (2×100 ml), the combined organics dried over magnesium sulphate and the solvent removed under reduced pressure to give 1-[2-(4-Chloro-phenyl)-thiazol-5-yl]-ethanol (4.71 g).
Step 3

Preparation of 3-{1-[2-(4-Chloro-phenyl)-thiazol-5-yl]-ethoxy}-cyclopent-2-enone

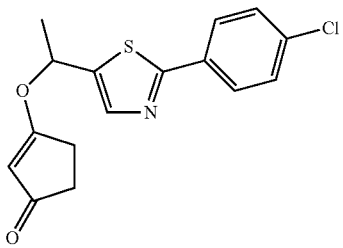 [SMILES: CC(OC1=CC(=O)CC1)c1cnc(-c2ccc(Cl)cc2)s1]

To a solution of 1-[2-(4-Chloro-phenyl)-thiazol-5-yl]-ethanol (4.1 g, 17.1 mmol) in anhydrous THF (100 ml), at 0° C. under an atmosphere of nitrogen was added cyclopentane-1,3-dione (2.18 g, 22.23 mmol), followed by triphenylphosphine (5.83 g, 22.23 mmol). Diisopropylazodicarboxylate (4.31 ml, 22.23 mmol) was then added dropwise over a period of 5 minutes and the reaction allowed to warm to room temperature and stirred for 2 hours. The crude reaction mixture was dry loaded onto silica and purified by flash chromatography to give 3-{1-[2-(4-Chloro-phenyl)-thiazol-5-yl]-ethoxy}-cyclopent-2-enone (2.29 g).

Step 4

Preparation of 2-[2-(4-Chloro-phenyl)-5-ethyl-thiazol-4-yl]-cyclopentane-1,3-dione

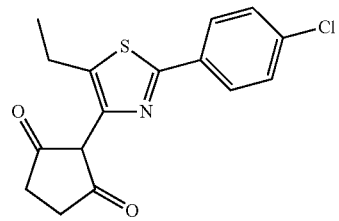 [SMILES: CCc1sc(-c2ccc(Cl)cc2)nc1C1C(=O)CCC1=O]

To a solution of 3-{1-[2-(4-Chloro-phenyl)-thiazol-5-yl]-ethoxy}-cyclopent-2-enone (2.29 g, 7.16 mmol) in ethylene glycol dimethyl ether (10 ml) was added 1-butyl-3-methylimidazolium bis(trifluoromethylsulphonyl)imide (100 µl) and the reaction heated to 230° C. by microwave irradiation for 30 minutes. The crude reaction mixture was dry loaded onto silica and purified by flash chromatography to give 2-[2-(4-Chloro-phenyl)-5-ethyl-thiazol-4-yl]-cyclopentane-1,3-dione (681 mg).

Step 5

Preparation of 2-[2-(4-Chloro-phenyl)-5-ethyl-thiazol-4-yl]-3-methoxy-cyclopent-2-enone

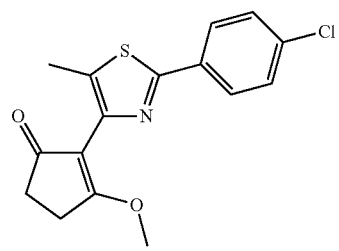 [SMILES: COC1=C(c2nc(-c3ccc(Cl)cc3)sc2C)C(=O)CC1]

To a solution of 2-[2-(4-Chloro-phenyl)-5-ethyl-thiazol-4-yl]-cyclopentane-1,3-dione (650 mg, 2.03 mmol) in acetone (10 ml) was added potassium carbonate (553 mg, 4 mmol), followed by iodomethane (248 µl, 4 mmol), and the reaction heated to 40° C. for 6 hours. The solvent was then removed from the crude reaction mixture under reduced pressure and the residue partitioned between water (100 ml) and ethyl acetate (100 ml). The organic layer was separated, dry loaded onto silica and purified by flash chromatography to give 2-[2-(4-Chloro-phenyl)-5-ethyl-thiazol-4-yl]-3-methoxy-cyclopent-2-enone (395 mg).

Step 6

Preparation of 2-[2-(4-Chloro-phenyl)-5-ethyl-thiazol-4-yl]-5-[hydroxy-(tetrahydro-pyran-4-yl)-methyl]-3-methoxy-cyclopent-2-enone

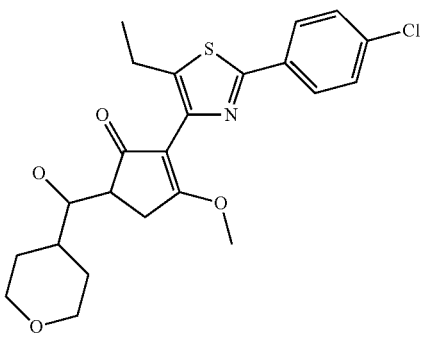 [SMILES: CCc1sc(-c2ccc(Cl)cc2)nc1C1=C(OC)CC(C(O)C2CCOCC2)C1=O]

To a solution of 2-[2-(4-Chloro-phenyl)-5-ethyl-thiazol-4-yl]-3-methoxy-cyclopent-2-enone (175 mg, 0.52 mmol) in anhydrous tetrahydrofuran (5 ml) at −78° C. under an atmosphere of nitrogen was added lithium diisopropylamide (1.8M in THF/heptanes/ethylbenzene; 1.1 ml, 2 mmol) dropwise over a period of 1 minute and the reaction allowed to stir at 78° C. for 40 minutes. A solution of tetrahydro-pyran-4-carbaldehyde (228 mg, 2 mmol) in anhydrous tetrahydrofuran (1 ml) was then added dropwise over a period of 30 seconds before the reaction was allowed to warm to room temperature and stirred for a further 30 minutes. The reaction was quenched by the addition of saturated aqueous ammonium chloride solution (50 ml) and extracted with ethyl acetate (50 ml) and the organic layer separated, dry loaded onto silica and purified by flash chromatography to give 2-[2-(4-Chloro-phenyl)-5-ethyl-thiazol-4-yl]-5-[hydroxy-(tetrahydro-pyran-4-yl)-methyl]-3-methoxy-cyclopent-2-enone (86 mg).

Step 7

Preparation of 2-[2-(4-Chloro-phenyl)-5-ethyl-thiazol-4-yl]-4-[1-(tetrahydro-pyran-4-yl)-meth-(E)-ylidene]-cyclopentane-1,3-dione

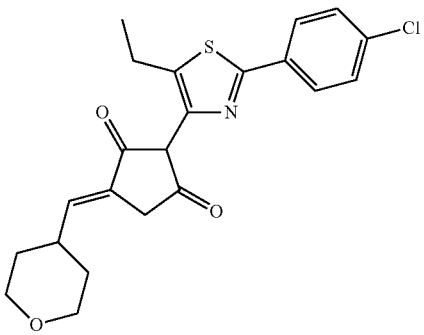 [SMILES: CCc1sc(-c2ccc(Cl)cc2)nc1C1C(=O)C/C(=C\C2CCOCC2)C1=O]

To a stirred solution of 2-[2-(4-Chloro-phenyl)-5-ethyl-thiazol-4-yl]-3-methoxy-5-[1-(tetrahydro-pyran-4-yl)-meth-(E)-ylidene]-cyclopent-2-enone (85 mg, 0.19 mmol) in 1,4-dioxane (3 ml) was added 12M hydrochloric acid (32 µl, 0.38 mmol) and the reaction heated to 60° C. for 12 hours. The solvent was removed under reduced pressure and the residue purified by mass-directed preparative HPLC to give 2-[2-(4-Chloro-phenyl)-5-ethyl-thiazol-4-yl]-4-[1-(tetrahydro-pyran-4-yl)-meth-(E)-ylidene]-cyclopentane-1,3-dione (4 mg).

Example 4

Preparation of 2-[5-(4-Chloro-phenyl)-2-methyl-thiophen-3-yl]-4-(tetrahydro-pyran-4-ylmethyl)-cyclopentane-1,3-dione

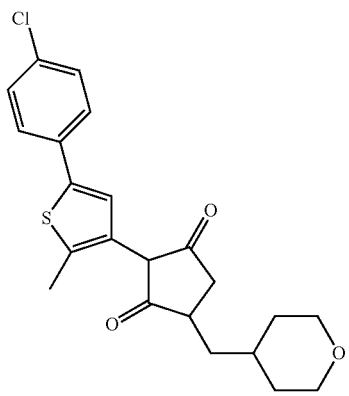

Step 1

Preparation of [5-(4-Chloro-phenyl)-thiophen-2-yl]-methanol

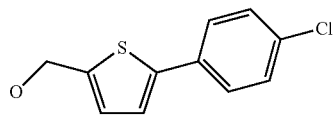 [SMILES: OCc1ccc(-c2ccc(Cl)cc2)s1]

To a solution of 5-(4-Chloro-phenyl)-thiophene-2-carbaldehyde (5 g, 22.45 mmol) in methanol (250 ml) at 0° C. under an atmosphere of nitrogen was added sodium borohydride (1.02 g, 26.94 mmol) portionwise over a period of 5 minutes. The reaction was then allowed to warm to room temperature and stirred for 3 hours. The reaction was quenched with saturated aqueous ammonium chloride solution (100 ml) and stirred for 5 minutes, before the methanol is removed under reduced pressure. The resulting heterogeneous mixture was then extracted with ethyl acetate (2×100 ml), the combined organics dried over magnesium sulphate and the solvent removed under reduced pressure to give [5-(4-Chloro-phenyl)-thiophen-2-yl]-methanol (4.89 g).

Step 2

Preparation of 3-[5-(4-Chloro-phenyl)-thiophen-2-ylmethoxy]-cyclopent-2-enone

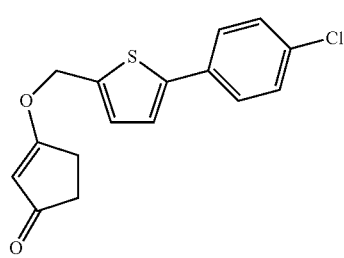 [SMILES: O=C1C=C(OCc2ccc(-c3ccc(Cl)cc3)s2)CC1]

To a solution of [2-(4-Chloro-phenyl)-thiazol-5-yl]-methanol (4.89 g, 21.75 mmol) in anhydrous THF (100 ml), at 0° C. under an atmosphere of nitrogen was added cyclopentane-1,3-dione (2.78 g, 28.27 mmol) followed by triphenylphosphine (7.41 g, 28.27 mmol). Diisopropylazodicarboxylate (5.48 ml, 28.27 mmol) was then added dropwise over a period of 5 minutes and the reaction allowed to warm to room temperature and stirred for 2 hours. The crude reaction mixture was dry loaded onto silica and purified by flash chromatography to give 3-[5-(4-Chloro-phenyl)-thiophen-2-ylmethoxy]-cyclopent-2-enone (5.1 g).

Step 3

Preparation of 2-[5-(4-Chloro-phenyl)-2-methyl-thiophen-3-yl]-cyclopentane-1,3-dione

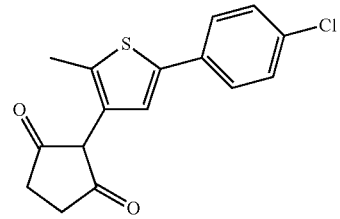 [SMILES: Cc1sc(-c2ccc(Cl)cc2)cc1C1C(=O)CCC1=O]

To a solution of 3-[5-(4-Chloro-phenyl)-thiophen-2-ylmethoxy]-cyclopent-2-enone (4.89, 4.22 mmol) in 1,2-diemethoxyethane (10 ml) was added 1-butyl-3-methylimidazolium bis(trifluoromethylsulphonyl)imide (100 µl) and the reaction heated to 180° C. by microwave irradiation for 30 minutes. The crude reaction mixture was dry loaded onto silica and purified by flash chromatography to give 2-[5-(4-Chloro-phenyl)-2-methyl-thiophen-3-yl]-cyclopentane-1,3-dione (2.21 g).

Step 4

Preparation of 2-[5-(4-Chloro-phenyl)-2-methyl-thiophen-3-yl]-3-methoxy-cyclopent-2-enone

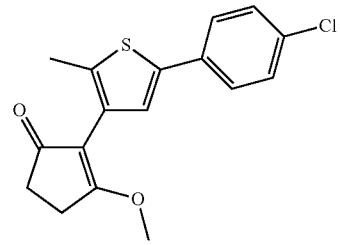 [SMILES: COC1=C(c2cc(-c3ccc(Cl)cc3)sc2C)C(=O)CC1]

To a solution of 2-[5-(4-Chloro-phenyl)-2-methyl-thiophen-3-yl]-cyclopentane-1,3-dione (2.21 g, 7.25 mmol) in acetone (50 ml) was added potassium carbonate (1514 g, 10.87 mmol) followed by iodomethane (670 µl, 10.87 mmol) and the reaction heated to 40° C. for 6 hours. The solvent was then removed from the crude reaction mixture under reduced pressure and the residue partitioned between water (100 ml) and ethyl acetate (100 ml). The organic layer was separated, dry loaded onto silica and purified by flash chromatography to give 2-[5-(4-Chloro-phenyl)-2-methyl-thiophen-3-yl]-3-methoxy-cyclopent-2-enone (818 mg).

Step 5

Preparation of 2-[5-(4-Chloro-phenyl)-2-methyl-thiophen-3-yl]-5-[hydroxy-(tetrahydro-pyran-4-yl)-methyl]-3-methoxy-cyclopent-2-enone

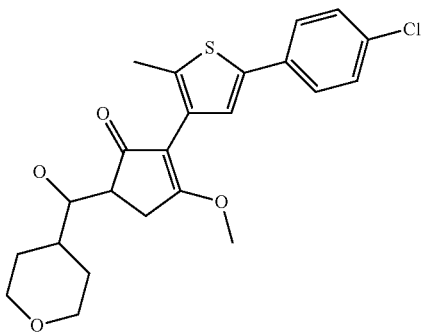 [SMILES: COC1=C(c2cc(-c3ccc(Cl)cc3)sc2C)C(=O)C(C(O)C2CCOCC2)C1]

To a solution of 2-[5-(4-Chloro-phenyl)-2-methyl-thiophen-3-yl]-3-methoxy-cyclopent-2-enone (255 mg, 0.8 mmol) in anhydrous tetrahydrofuran (6 ml) at −78° C. under an atmosphere of nitrogen was added lithium diisopropylamide (1.8M in THF/heptanes/ethylbenzene; 0.49 ml, 0.89 mmol) dropwise over a period of 5 minutes and the reaction allowed to stir at 78° C. for 30 minutes. A solution of tetrahydro-pyran-4-carbaldehyde (102 mg, 0.89 mmol) in anhydrous tetrahydrofuran (1 ml) was then added dropwise over a period of 5 minutes before the reaction was allowed to warm to room temperature and stirred for a further 30 minutes. The reaction was quenched by the addition of saturated aqueous ammonium chloride solution (50 ml) and extracted with ethyl acetate (50 ml) and the organic later separated, dry loaded onto silica and purified by flash chromatography to give 2-[5-(4-Chloro-phenyl)-2-methyl-thiophen-3-yl]-5-[hydroxy-(tetrahydro-pyran-4-yl)-methyl]-3-methoxy-cyclopent-2-enone (292 mg).

Step 6

Preparation of 2-[5-(4-Chloro-phenyl)-2-methyl-thiophen-3-yl]-4-[1-(tetrahydro-pyran-4-yl)-meth-(E)-ylidene]-cyclopentane-1,3-dione

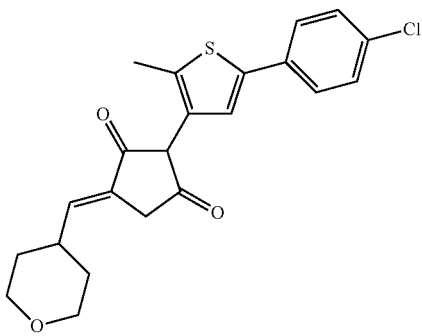 [SMILES: Cc1sc(-c2ccc(Cl)cc2)cc1C1C(=O)C/C(=C\C2CCOCC2)C1=O]

To a solution of 2-[5-(4-Chloro-phenyl)-2-methyl-thiophen-3-yl]-5-[hydroxy-(tetrahydro-pyran-4-yl)-methyl]-3-methoxy-cyclopent-2-enone (280 mg, 0.65 mmol) in acetone (2 ml) was added 2N hydrochloric acid (2 ml) and the reaction heated to 120° C. for 60 minutes by microwave irradiation. The crude reaction was diluted with ethyl acetate (25 ml) and washed with saturated aqueous ammonium chloride solution (25 ml), brine (25 ml) and the organic layer dry loaded onto silica and purified by flash chromatography to give 2-[5-(4-Chloro-phenyl)-2-methyl-thiophen-3-yl]-4-[1-(tetrahydro-pyran-4-yl)-meth-(E)-ylidene]-cyclopentane-1,3-dione (88 mg).

Step 7

Preparation of 2-[5-(4-Chloro-phenyl)-2-methyl-thiophen-3-yl]-4-(tetrahydro-pyran-4-ylmethyl)-cyclopentane-1,3-dione

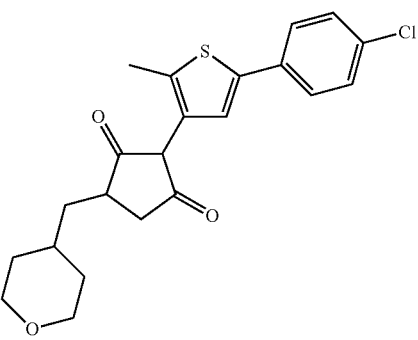 [SMILES: Cc1sc(-c2ccc(Cl)cc2)cc1C1C(=O)CC(CC2CCOCC2)C1=O]

To a solution of 2-[5-(4-Chloro-phenyl)-2-methyl-thiophen-3-yl]-4-[1-(tetrahydro-pyran-4-yl)-meth-(E)-ylidene]-cyclopentane-1,3-dione (88 mg, 0.22 mmol) in ethanol (2 ml) was added 5% palladium on carbon (9 mg) and the reaction stirred under an atmosphere of hydrogen at a pressure of 2 bar for 4 hours. The crude reaction mixture was filtered through a pad of Celite and purified by preparative mass-directed HPLC to give 2-[5-(4-Chloro-phenyl)-2-methyl-thiophen-3-yl]-4-(tetrahydro-pyran-4-ylmethyl)-cyclopentane-1,3-dione (43 mg).

Preparation of 2-[5-(4-Chloro-phenyl)-2-methyl-thiophen-3-yl]-4-(tetrahydro-furan-3-ylmethyl)-cyclopentane-1,3-dione

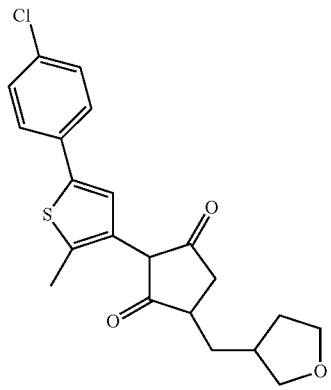 [SMILES: Cc1sc(-c2ccc(Cl)cc2)cc1C1C(=O)CC(CC2CCOC2)C1=O]

Step 1

Preparation of 2-[5-(4-Chloro-phenyl)-2-methyl-thiophen-3-yl]-3-methoxy-5-(tetrahydro-furan-3-ylmethyl)-cyclopent-2-enone

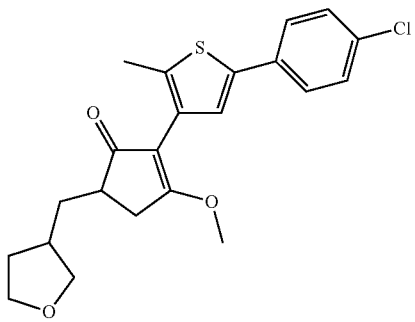 [SMILES: COC1=C(c2cc(-c3ccc(Cl)cc3)sc2C)C(=O)C(CC2CCOC2)C1]

To a solution of 2-[5-(4-Chloro-phenyl)-2-methyl-thiophen-3-yl]-3-methoxy-cyclopent-2-enone (285 mg, 0.89 mmol) in anhydrous tetrahydrofuran (6 ml) at −78° C. under an atmosphere of nitrogen is added lithium diisopropylamide (1.8M in THF/heptanes/ethylbenzene; 0.55 ml, 1.0 mmol) dropwise over a period of 5 minutes and the reaction allowed to stir at −78° C. for 30 minutes. A solution of 3-iodomethyl tetrahydrofuran (212 mg, 1 mmol) in anhydrous tetrahydrofuran (1 ml) was then added dropwise over a period of 5 minutes before the reaction was allowed to warm to room temperature and stirred for a further 30 minutes. The reaction was quenched by the addition of saturated aqueous ammonium chloride solution (50 ml) and extracted with ethyl acetate (50 ml) and the organic later separated, dry loaded onto silica and purified by flash chromatography to give 2-[5-(4-Chloro-phenyl)-2-methyl-thiophen-3-yl]-3-methoxy-5-(tetrahydro-furan-3-ylmethyl)-cyclopent-2-enone (150 mg)

Step 2

Preparation of 2-[5-(4-Chloro-phenyl)-2-methyl-thiophen-3-yl]-4-(tetrahydro-furan-3-ylmethyl)-cyclopentane-1,3-dione

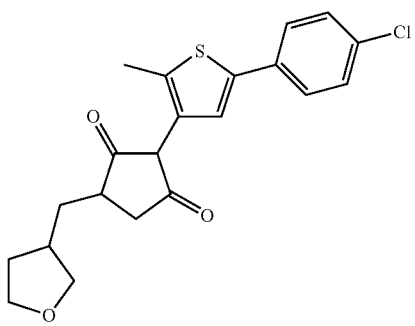 [SMILES: Cc1sc(-c2ccc(Cl)cc2)cc1C1C(=O)CC(CC2CCOC2)C1=O]

To a solution of 2-[5-(4-Chloro-phenyl)-2-methyl-thiophen-3-yl]-3-methoxy-5-(tetrahydro-furan-3-ylmethyl)-cyclopent-2-enone (150 mg, 0.37 mmol) in acetone (2 ml) was added 2N hydrochloric acid (2 ml) and the reaction heated to 120° C. for 60 minutes by microwave irradiation. The crude reaction was diluted with ethyl acetate (25 ml) and washed with saturated aqueous ammonium chloride solution (25 ml), brine (25 ml). The solvent was removed under reduce pressure and the residue purified by mass-directed preparative HPLC to give 2-[5-(4-Chloro-phenyl)-2-methyl-thiophen-3-yl]-4-(tetrahydro-furan-3-ylmethyl)-cyclopentane-1,3-dione (15 mg).

Compounds characterised by HPLC-MS were analysed using one of three methods described below.

Method A

Compounds characterised by HPLC-MS were analysed using a Waters 2795 HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using a three minutes run time, according to the following gradient table:

| Time (mins) | Solvent A (%) | Solvent B (%) | Flow (ml/mn) |
|---|---|---|---|
| 0.00 | 90.0 | 10.0 | 2.00 |
| 0.25 | 90.0 | 10.0 | 2.00 |
| 2.00 | 10.0 | 90.0 | 2.00 |
| 2.50 | 10.0 | 90.0 | 2.00 |
| 2.60 | 90.0 | 10.0 | 2.00 |
| 3.0 | 90.0 | 10.0 | 2.00 |

Solvent A: H₂O containing 0.1% HCOOH
Solvent B: CH₃CN containing 0.1% HCOOH

Method B

Compounds characterised by HPLC-MS were analysed using an Waters 2777 injector with a 1525 micro pump HPLC equipped with a Waters Atlantis dC18 IS column (column length 20 mm, internal diameter of column 3 mm, particle size 3 micron), Waters 2996 photodiode array, Waters 2420 ELSD and Micromass ZQ2000. The analysis was conducted using a three minutes run time, according to the following gradient table:

| Time (mins) | Solvent A (%) | Solvent B (%) | Flow (ml/mn) |
|---|---|---|---|
| 0.00 | 95.0 | 5 | 1.300 |
| 2.50 | 0.00 | 100 | 1.300 |
| 2.80 | 0.00 | 100 | 1.300 |
| 2.90 | 95.0 | 5 | 1.300 |

Solvent A: H₂O with 0.05% TFA
Solvent B: CH₃CN with 0.05% TFA

Method C:

Compounds characterised by HPLC-MS were analysed using a Finnigan Surveyor MSQ Plus equipped with a Waters Xterra column (column length 50 mm, internal diameter of column 4.6 mm, particle size 3.5 micron, temperature 40° C.), Waters photodiode array and Micromass ZQ2000. The analysis was conducted using a six minutes run time, according to the following gradient table:

| Time (mins) | Solvent A (%) | Solvent B (%) | Flow (ml/mn) |
|---|---|---|---|
| 0.00 | 90.0 | 10.0 | 1.30 |
| 3.80 | 0.00 | 100 | 1.30 |
| 4.80 | 0.00 | 100 | 1.30 |
| 5.00 | 90.0 | 10.0 | 1.30 |
| 6.00 | 90.0 | 10.0 | 1.30 |

Solvent A: H₂O containing 0.05% HCOOH
Solvent B: CH₃CN containing 0.05% HCOOH

Method D

Compounds characterised by HPLC-MS were analysed using a Waters Acquity UPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using a two minute run time, according to the following gradient table:

| Time (mins) | Solvent A (%) | Solvent B (%) | Flow (ml/mn) |
|---|---|---|---|
| 0.00 | 90.0 | 10.0 | 2.00 |
| 1.50 | 10.0 | 90.0 | 2.00 |
| 1.75 | 10.0 | 90.0 | 2.00 |
| 1.9 | 90.0 | 10.0 | 2.00 |
| 2.00 | 90.0 | 10.0 | 2.00 |

Solvent A: $H_2O$ containing 0.1% HCOOH
Solvent B: $CH_3CN$ containing 0.1% HCOOH

TABLE A1

| Compound Number | Structure | LC/MS, NMR or other physical data |
|---|---|---|
| A1 | 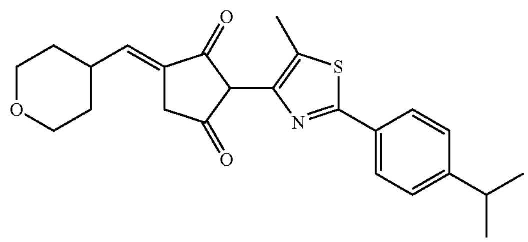 [SMILES: Cc1sc(-c2ccc(C(C)C)cc2)nc1C1C(=O)C/C(=C\C2CCOCC2)C1=O] | LC/MS (Method D) ES$^+$: MH$^+$ = 410 rt = 1.43 min |
| A2 | 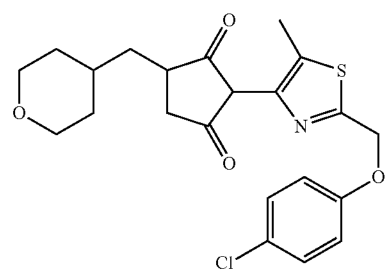 [SMILES: Cc1sc(COc2ccc(Cl)cc2)nc1C1C(=O)CC(CC2CCOCC2)C1=O] | LC/MS (Method D) ES$^+$: MH$^+$ = 434, 436 rt = 1.03 min |
| A3 | 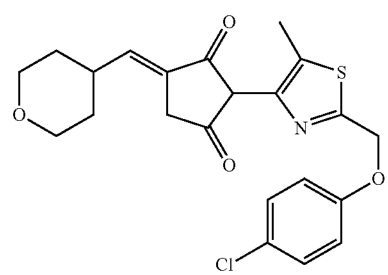 [SMILES: Cc1sc(COc2ccc(Cl)cc2)nc1C1C(=O)C/C(=C\C2CCOCC2)C1=O] | LC/MS (Method D) ES$^+$: MH$^+$ = 432, 434 rt = 1.16 min |
| A4 | 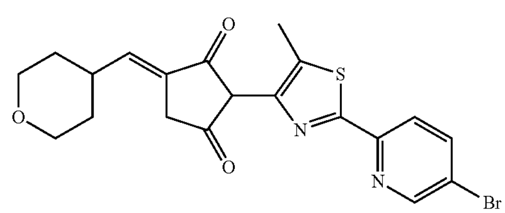 [SMILES: Cc1sc(-c2ccc(Br)cn2)nc1C1C(=O)C/C(=C\C2CCOCC2)C1=O] | LC/MS (Method D) ES$^+$: MH$^+$ = 447, 449 rt = 1.12 min |
| A5 | 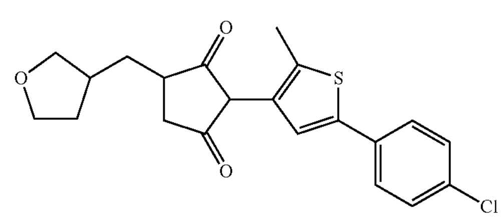 [SMILES: Cc1sc(-c2ccc(Cl)cc2)cc1C1C(=O)CC(CC2CCOC2)C1=O] | LC/MS (Method D) ES$^+$: MH$^+$ = 389, 391 rt = 0.94 min |

TABLE A1-continued
| Compound Number | Structure | LC/MS, NMR or other physical data |
|---|---|---|
| A6 | 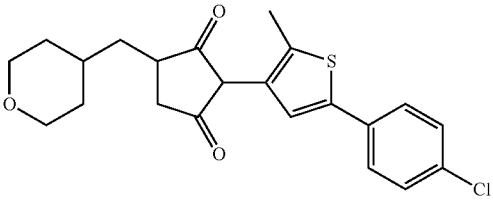 [SMILES: Cc1sc(-c2ccc(Cl)cc2)cc1C1C(=O)CC(CC2CCOCC2)C1=O] | LC/MS (Method D)<br>ES+: MH+ = 403, 405<br>rt = 0.99 min |
| A7 | 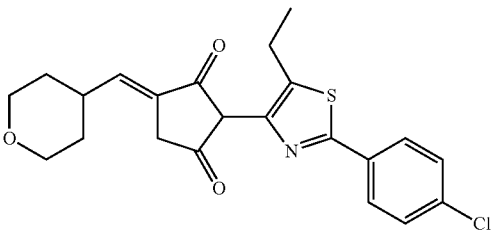 [SMILES: CCc1sc(-c2ccc(Cl)cc2)nc1C1C(=O)C/C(=C\C2CCOCC2)C1=O] | LC/MS (Method D)<br>ES+: MH+ = 416, 418<br>rt = 1.35 min |
| A8 | 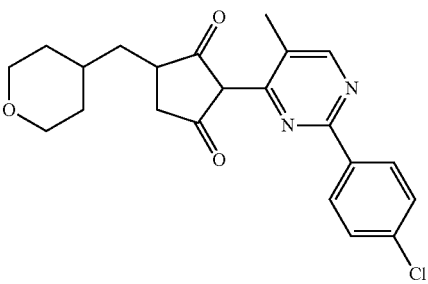 [SMILES: Cc1cnc(-c2ccc(Cl)cc2)nc1C1C(=O)CC(CC2CCOCC2)C1=O] | LC/MS (Method D)<br>ES+: MH+ = 399, 401<br>rt = 1.00 min |
| A9 | 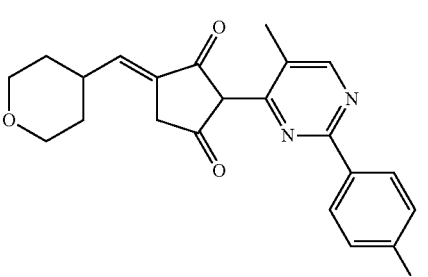 | LC/MS (Method D)<br>ES+: MH+ = 397, 399<br>rt = 1.04 min |
| A10 | 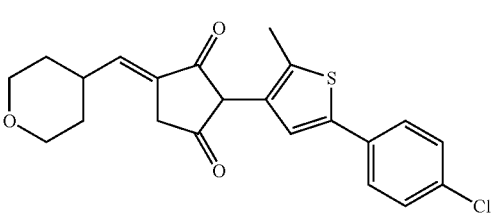 | LC/MS (Method D)<br>ES+: MH+ = 401, 403<br>rt = 1.01 min |
| A11 | 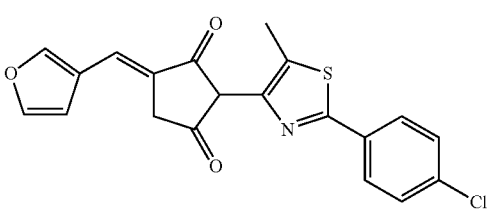 [SMILES: Cc1sc(-c2ccc(Cl)cc2)nc1C1C(=O)C/C(=C\c2ccoc2)C1=O] | LC/MS (Method D)<br>ES+: MH+ = 384, 386<br>rt = 1.36 min |

TABLE A1-continued

| Compound Number | Structure | LC/MS, NMR or other physical data |
|---|---|---|
| A12 | 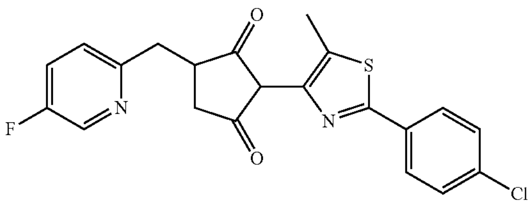 [SMILES: Cc1sc(-c2ccc(Cl)cc2)nc1C1C(=O)CC(Cc2ccc(F)cn2)C1=O] | LC/MS (Method D) ES+: MH+ = 415, 417 rt = 1.03 min |
| A13 | 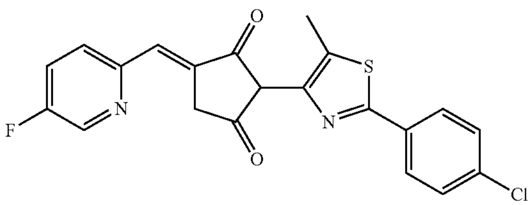 [SMILES: Cc1sc(-c2ccc(Cl)cc2)nc1C1C(=O)C/C(=C\c2ccc(F)cn2)C1=O] | LC/MS (Method D) ES+: MH+ = 413, 415 rt = 1.03 min |
| A14 | 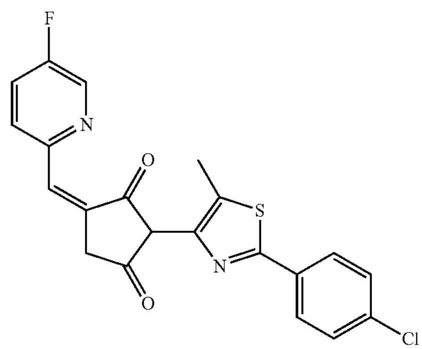 [SMILES: Cc1sc(-c2ccc(Cl)cc2)nc1C1C(=O)C/C(=C/c2ccc(F)cn2)C1=O] | LC/MS (Method D) ES+: MH+ = 413, 415 rt = 1.41 min |
| A15 | 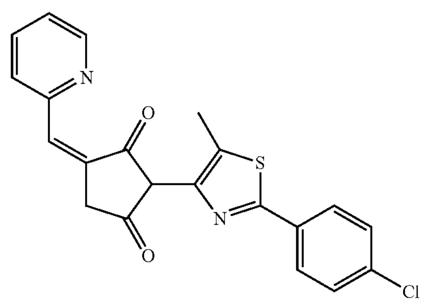 [SMILES: Cc1sc(-c2ccc(Cl)cc2)nc1C1C(=O)C/C(=C/c2ccccn2)C1=O] | LC/MS (Method D) ES+: MH+ = 395, 397 rt = 1.24 min |
| A16 | 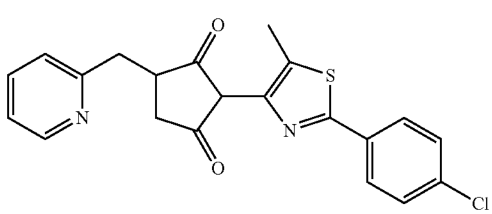 [SMILES: Cc1sc(-c2ccc(Cl)cc2)nc1C1C(=O)CC(Cc2ccccn2)C1=O] | LC/MS (Method D) ES+: MH+ = 397, 399 rt = 0.79 min |
| A17 | 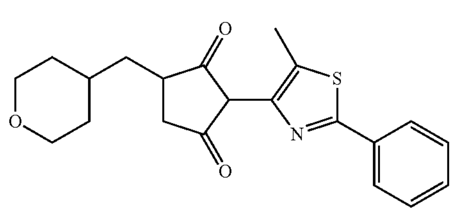 [SMILES: Cc1sc(-c2ccccc2)nc1C1C(=O)CC(CC2CCOCC2)C1=O] | LC/MS (Method D) ES+: MH+ = 370 rt = 1.02 min |

TABLE A1-continued

| Compound Number | Structure | LC/MS, NMR or other physical data |
|---|---|---|
| A18 | 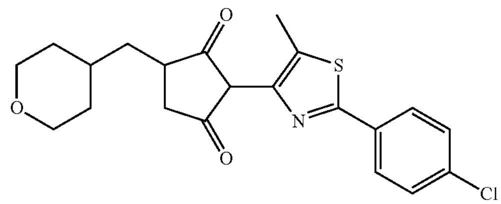 [SMILES: Cc1sc(-c2ccc(Cl)cc2)nc1C1C(=O)CC(CC2CCOCC2)C1=O] | LC/MS (Method D) ES+: MH+ = 404, 406 rt = 1.12 min |
| A19 | 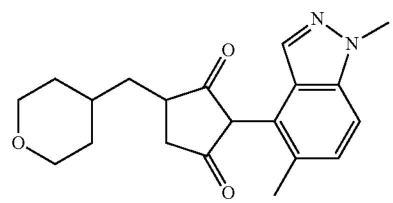 [SMILES: Cc1ccc2c(cnn2C)c1C1C(=O)CC(CC2CCOCC2)C1=O] | LC/MS (Method A) ES+: MH+ = 341, 342 rt = 1.14 min |
| A20 | 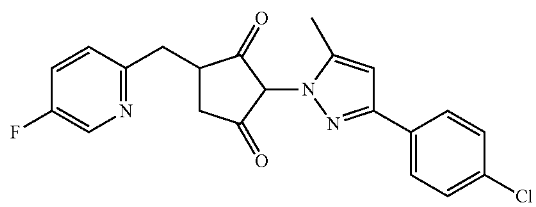 [SMILES: Cc1cc(-c2ccc(Cl)cc2)nn1C1C(=O)CC(Cc2ccc(F)cn2)C1=O] | LC/MS (Method A) ES+: MH+ = 398, 400 rt = 1.41 min |
| A21 | 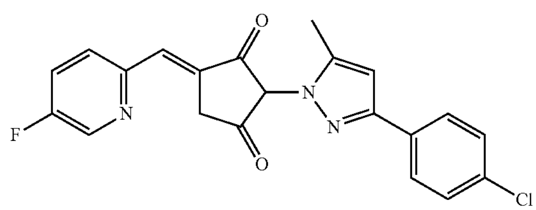 [SMILES: Cc1cc(-c2ccc(Cl)cc2)nn1C1C(=O)C/C(=C\c2ccc(F)cn2)C1=O] | LC/MS (Method A) ES+: MH+ = 396, 398 rt = 1.45 min |
| A22 | 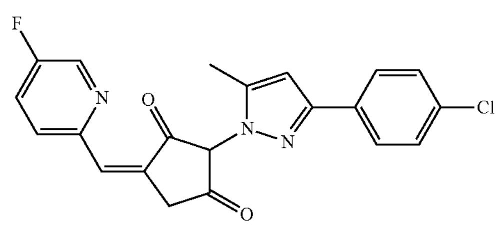 [SMILES: Cc1cc(-c2ccc(Cl)cc2)nn1C1C(=O)C/C(=C/c2ccc(F)cn2)C1=O] | LC/MS (Method A) ES+: MH+ = 396, 398 rt = 1.59 min |
| A23 | 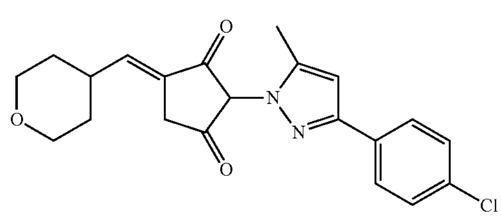 [SMILES: Cc1cc(-c2ccc(Cl)cc2)nn1C1C(=O)C/C(=C\C2CCOCC2)C1=O] | LC/MS (Method A) ES+: MH+ = 385, 387 rt = 1.40 min |
| A24 | 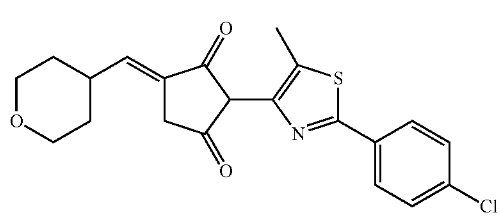 [SMILES: Cc1sc(-c2ccc(Cl)cc2)nc1C1C(=O)C/C(=C\C2CCOCC2)C1=O] | LC/MS (Method D) ES+: MH+ = 402, 404 rt = 1.27 min |

TABLE A1-continued

| Compound Number | Structure | LC/MS, NMR or other physical data |
|---|---|---|
| A25 | (structure shown) | LC/MS (Method A) ES⁺: MH⁺ = 387, 389<br>rt = 1.35 min |

Table 1 covers 98 compounds of the following type:

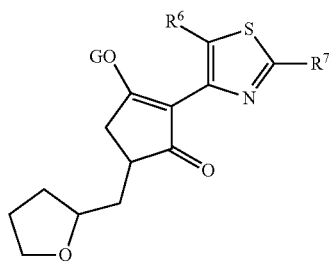

where $G_1$ is hydrogen, and $R^6$ and $R^7$ are as described in Table 1 below:

| Compound Number | $R^6$ | $R^7$ |
|---|---|---|
| 1.001 | CH₃ | H |
| 1.002 | CH₃ | F |
| 1.003 | CH₃ | Cl |
| 1.004 | CH₃ | Br |
| 1.005 | CH₃ | I |
| 1.006 | CH₃ | CH₃ |
| 1.007 | CH₃ | CH₂CH₃ |
| 1.008 | CH₃ | n-Pr |
| 1.009 | CH₃ | i-Pr |
| 1.010 | CH₃ | n-Bu |
| 1.011 | CH₃ | i-Bu |
| 1.012 | CH₃ | t-Bu |
| 1.013 | CH₃ | OCH₃ |
| 1.014 | CH₃ | OCH₂CH₃ |
| 1.015 | CH₃ | On-Pr |
| 1.016 | CH₃ | Oi-Pr |
| 1.017 | CH₃ | —CCH |
| 1.018 | CH₃ | —CH=CH₂ |
| 1.019 | CH₃ | Phenyl |
| 1.020 | CH₃ | 2-fluorophenyl |
| 1.021 | CH₃ | 2-chlorophenyl |
| 1.022 | CH₃ | 2-trifluoromethylphenyl |
| 1.023 | CH₃ | 2-nitrophenyl |
| 1.024 | CH₃ | 2-methylphenyl |
| 1.025 | CH₃ | 2-methanesulfonylphenyl |
| 1.026 | CH₃ | 2-cyanophenyl |
| 1.027 | CH₃ | 3-fluorophenyl |
| 1.028 | CH₃ | 3-chlorophenyl |
| 1.029 | CH₃ | 3-trifluoromethylphenyl |
| 1.030 | CH₃ | 3-nitrophenyl |
| 1.031 | CH₃ | 3-methylphenyl |
| 1.032 | CH₃ | 3-methanesulfonylphenyl |
| 1.033 | CH₃ | 3-cyanophenyl |
| 1.034 | CH₃ | 4-fluorophenyl |
| 1.035 | CH₃ | 4-chlorophenyl |
| 1.036 | CH₃ | 4-bromophenyl |
| 1.037 | CH₃ | 4-difluoromethoxyphenyl |
| 1.038 | CH₃ | 2-fluoro-4-chlorophenyl |
| 1.039 | CH₃ | 3-fluoro-4-chlorophenyl |
| 1.040 | CH₃ | 2-chloro-4-chlorophenyl |
| 1.041 | CH₃ | 2-chloro-4-fluorophenyl |
| 1.042 | CH₃ | 3-chloro-4-chlorophenyl |
| 1.043 | CH₃ | 3-chloro-4-fluorophenyl |
| 1.044 | CH₃ | 2-methyl-4-chlorophenyl |
| 1.045 | CH₃ | 4-trifluoromethylphenyl |
| 1.046 | CH₃ | 4-nitrophenyl |
| 1.047 | CH₃ | 4-methylphenyl |
| 1.048 | CH₃ | 4-methanesulfonylphenyl |
| 1.049 | CH₃ | 4-cyanophenyl |
| 1.050 | CH₂CH₃ | H |
| 1.051 | CH₂CH₃ | F |
| 1.052 | CH₂CH₃ | Cl |
| 1.053 | CH₂CH₃ | Br |
| 1.054 | CH₂CH₃ | I |
| 1.055 | CH₂CH₃ | CH₃ |
| 1.056 | CH₂CH₃ | CH₂CH₃ |
| 1.057 | CH₂CH₃ | n-Pr |
| 1.058 | CH₂CH₃ | i-Pr |
| 1.059 | CH₂CH₃ | n-Bu |
| 1.060 | CH₂CH₃ | i-Bu |
| 1.061 | CH₂CH₃ | t-Bu |
| 1.062 | CH₂CH₃ | OCH₃ |
| 1.063 | CH₂CH₃ | OCH₂CH₃ |
| 1.064 | CH₂CH₃ | On-Pr |
| 1.065 | CH₂CH₃ | Oi-Pr |
| 1.066 | CH₂CH₃ | —CCH |
| 1.067 | CH₂CH₃ | —CH=CH₂ |
| 1.068 | CH₂CH₃ | Phenyl |
| 1.069 | CH₂CH₃ | 2-fluorophenyl |
| 1.070 | CH₂CH₃ | 2-chlorophenyl |
| 1.071 | CH₂CH₃ | 2-trifluoromethylphenyl |
| 1.072 | CH₂CH₃ | 2-nitrophenyl |
| 1.073 | CH₂CH₃ | 2-methylphenyl |
| 1.074 | CH₂CH₃ | 2-methanesulfonylphenyl |
| 1.075 | CH₂CH₃ | 2-cyanophenyl |
| 1.076 | CH₂CH₃ | 3-fluorophenyl |
| 1.077 | CH₂CH₃ | 3-chlorophenyl |
| 1.078 | CH₂CH₃ | 3-trifluoromethylphenyl |
| 1.079 | CH₂CH₃ | 3-nitrophenyl |
| 1.080 | CH₂CH₃ | 3-methylphenyl |
| 1.081 | CH₂CH₃ | 3-methanesulfonylphenyl |
| 1.082 | CH₂CH₃ | 3-cyanophenyl |
| 1.083 | CH₂CH₃ | 4-fluorophenyl |
| 1.084 | CH₂CH₃ | 4-chlorophenyl |
| 1.085 | CH₂CH₃ | 4-bromophenyl |
| 1.086 | CH₂CH₃ | 4-difluoromethoxyphenyl |
| 1.087 | CH₂CH₃ | 2-fluoro-4-chlorophenyl |
| 1.088 | CH₂CH₃ | 3-fluoro-4-chlorophenyl |

-continued

| Compound Number | $R^6$ | $R^7$ |
|---|---|---|
| 1.089 | $CH_2CH_3$ | 2-chloro-4-chlorophenyl |
| 1.090 | $CH_2CH_3$ | 2-chloro-4-fluorophenyl |
| 1.091 | $CH_2CH_3$ | 3-chloro-4-chlorophenyl |
| 1.092 | $CH_2CH_3$ | 3-chloro-4-fluorophenyl |
| 1.093 | $CH_2CH_3$ | 2-methyl-4-chlorophenyl |
| 1.094 | $CH_2CH_3$ | 4-trifluoromethylphenyl |
| 1.095 | $CH_2CH_3$ | 4-nitrophenyl |
| 1.096 | $CH_2CH_3$ | 4-methylphenyl |
| 1.097 | $CH_2CH_3$ | 4-methanesulfonylphenyl |
| 1.098 | $CH_2CH_3$ | 4-cyanophenyl |

Table 2 covers 98 compounds of the following type

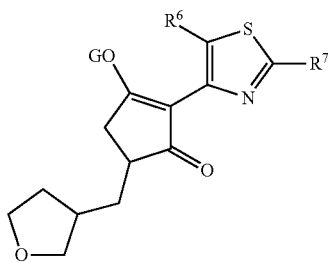

where G, is hydrogen, and $R^6$ and $R^7$ are as described in Table 1.

Table 3 covers 98 compounds of the following type

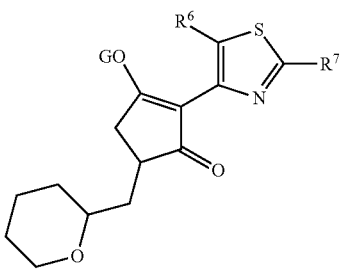

where G, is hydrogen, and $R^6$ and $R^7$ are as described in Table 1.

Table 4 covers 98 compounds of the following type

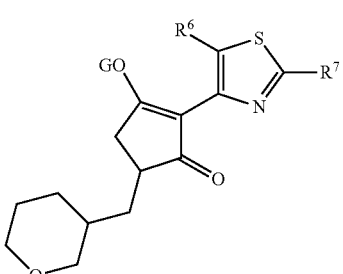

where G, is hydrogen, and $R^6$ and $R^7$ are as described in Table 1.

Table 5 covers 98 compounds of the following type

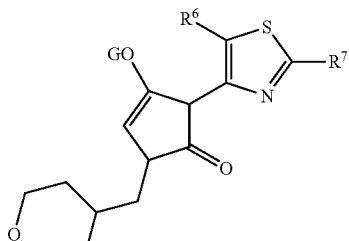

where G, is hydrogen, and $R^6$ and $R^7$ are as described in Table 1.

Table 6 covers 98 compounds of the following type

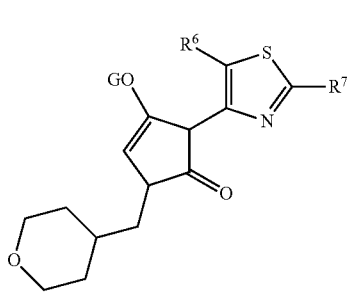

where G, is hydrogen, and $R^6$ and $R^7$ are as described in Table 1.

Table 7 covers 98 compounds of the following type

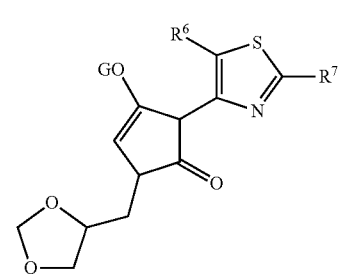

where G, is hydrogen, and $R^6$ and $R^7$ are as described in Table 1.

Table 8 covers 98 compounds of the following type

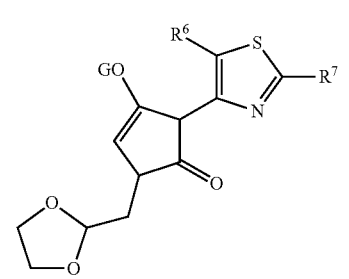

where G, is hydrogen, and $R^6$ and $R^7$ are as described in Table 1.

Table 8 covers 98 compounds of the following type

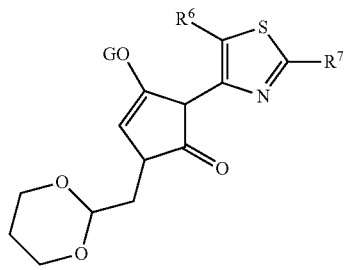

where G, is hydrogen, and $R^6$ and $R^7$ are as described in Table 1.

Table 9 covers 98 compounds of the following type

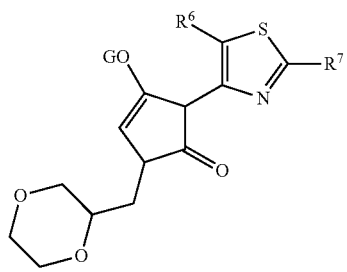

where G, is hydrogen, and $R^6$ and $R^7$ are as described in Table 1.

Table 10 covers 98 compounds of the following type

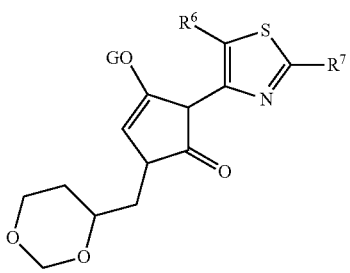

where G, is hydrogen, and $R^6$ and $R^7$ are as described in Table 1.

Table 11 covers 98 compounds of the following type

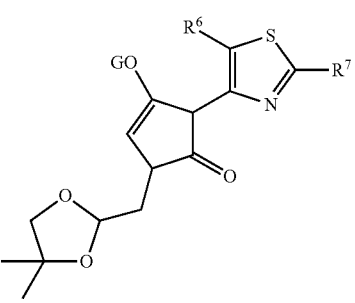

where G, is hydrogen, and $R^6$ and $R^7$ are as described in Table 1.

Table 12 covers 98 compounds of the following type

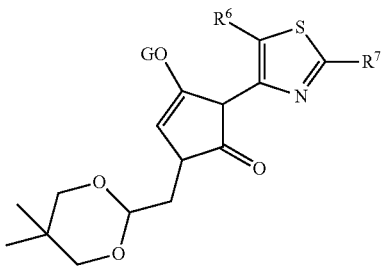

where G, is hydrogen, and $R^6$ and $R^7$ are as described in Table 1.

Table 13 covers 98 compounds of the following type

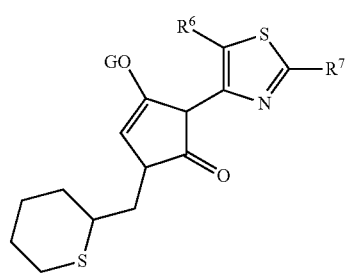

where G, is hydrogen, and $R^6$ and $R^7$ are as described in Table 1.

Table 14 covers 98 compounds of the following type

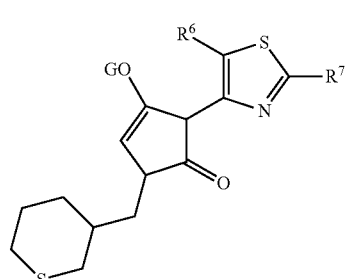

where G, is hydrogen, and $R^6$ and $R^7$ are as described in Table 1.

Table 15 covers 98 compounds of the following type

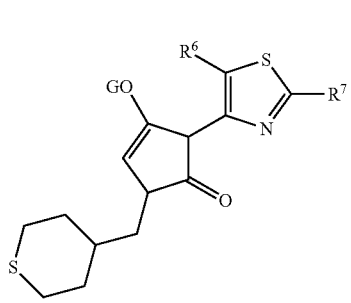

where G, is hydrogen, and $R^6$ and $R^7$ are as described in Table 1.

Table 16 covers 98 compounds of the following type

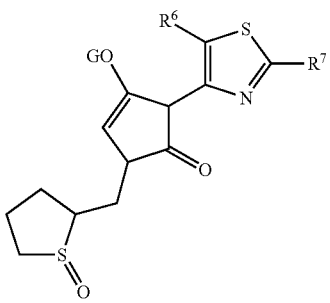

where G, is hydrogen, and $R^6$ and $R^7$ are as described in Table 1.

Table 17 covers 98 compounds of the following type

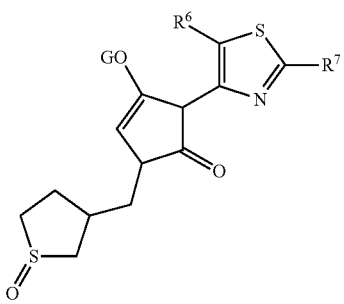

where G, is hydrogen, and $R^6$ and $R^7$ are as described in Table 1.

Table 18 covers 98 compounds of the following type

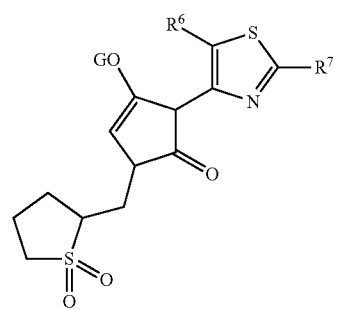

where G, is hydrogen, and $R^6$ and $R^7$ are as described in Table 1.

Table 19 covers 98 compounds of the following type

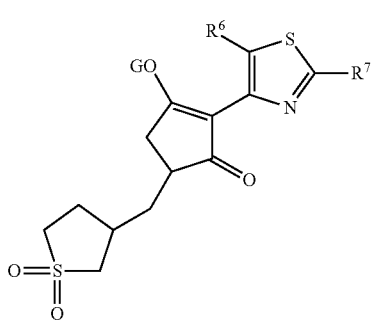

where G, is hydrogen, and $R^6$ and $R^7$ are as described in Table 1.

Table 20 covers 98 compounds of the following type

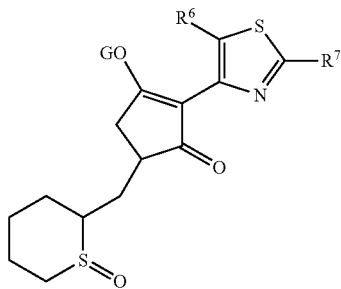

where G, is hydrogen, and $R^6$ and $R^7$ are as described in Table 1.

Table 21 covers 98 compounds of the following type

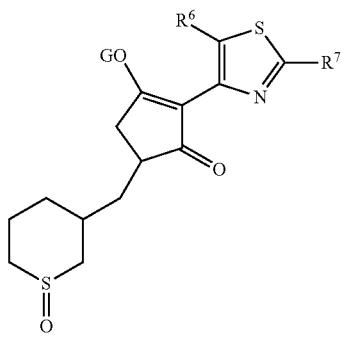

where G, is hydrogen, and $R^6$ and $R^7$ are as described in Table 1.

Table 22 covers 98 compounds of the following type

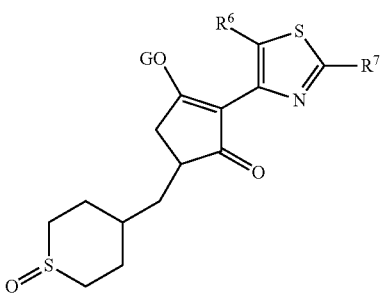

where G, is hydrogen, and $R^6$ and $R^7$ are as described in Table 1.

Table 23 covers 98 compounds of the following type

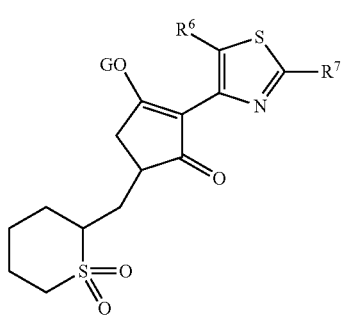

where G, is hydrogen, and $R^6$ and $R^7$ are as described in Table 1.

Table 24 covers 98 compounds of the following type

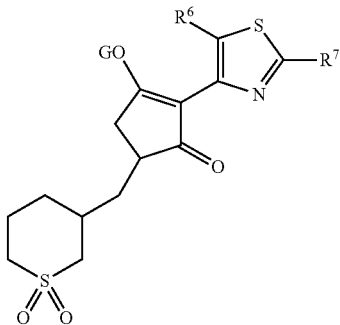

where G, is hydrogen, and $R^6$ and $R^7$ are as described in Table 1.

Table 25 covers 98 compounds of the following type

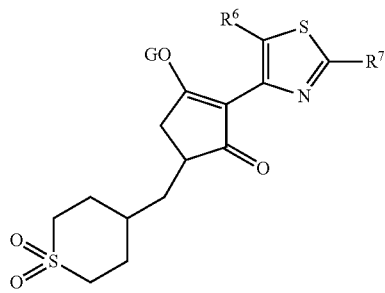

where G, is hydrogen, and $R^6$ and $R^7$ are as described in Table 1.

Table 26 covers 98 compounds of the following type

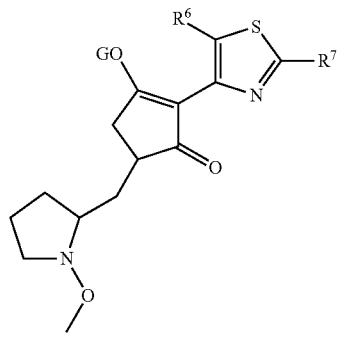

where G, is hydrogen, and $R^6$ and $R^7$ are as described in Table 1.

Table 26 covers 98 compounds of the following type

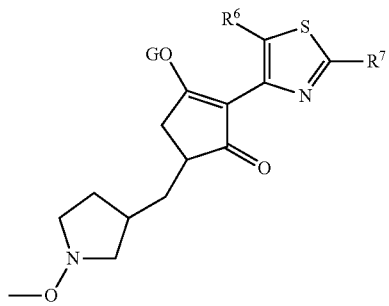

where G, is hydrogen, and $R^6$ and $R^7$ are as described in Table 1.

Table 28 covers 98 compounds of the following type

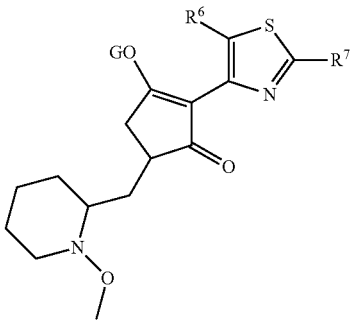

where G, is hydrogen, and $R^6$ and $R^7$ are as described in Table 1.

Table 29 covers 98 compounds of the following type

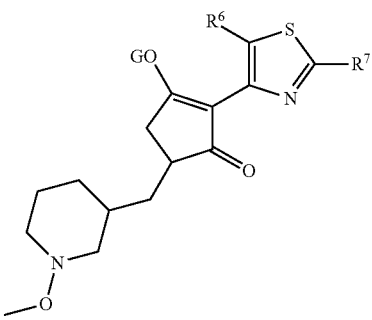

where G, is hydrogen, and $R^6$ and $R^7$ are as described in Table 1.

Table 30 covers 98 compounds of the following type

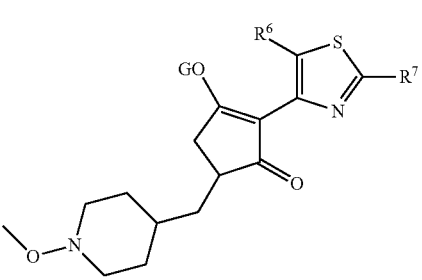

where G, is hydrogen, and $R^6$ and $R^7$ are as described in Table 1.

Table 31 covers 98 compounds of the following type

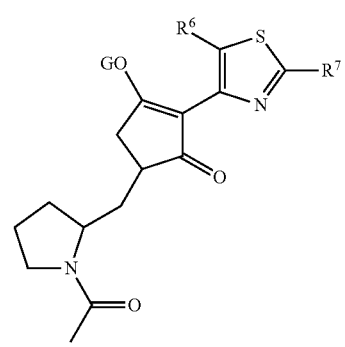

where G, is hydrogen, and $R^6$ and $R^7$ are as described in Table 1.

Table 32 covers 98 compounds of the following type

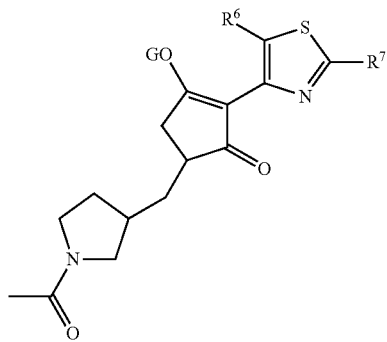

where G, is hydrogen, and $R^6$ and $R^7$ are as described in Table 1.

Table 33 covers 98 compounds of the following type

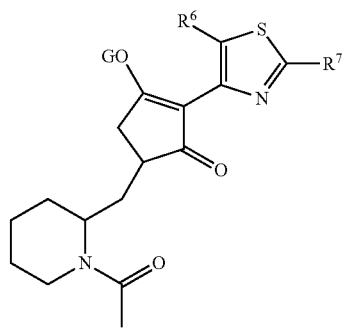

where G, is hydrogen, and $R^6$ and $R^7$ are as described in Table 1.

Table 34 covers 98 compounds of the following type

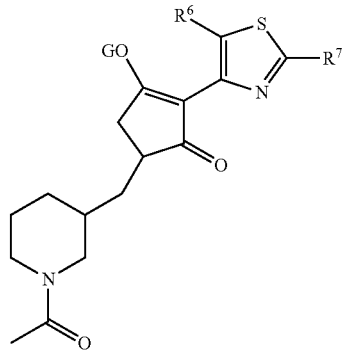

where G, is hydrogen, and $R^6$ and $R^7$ are as described in Table 1.

Table 35 covers 98 compounds of the following type

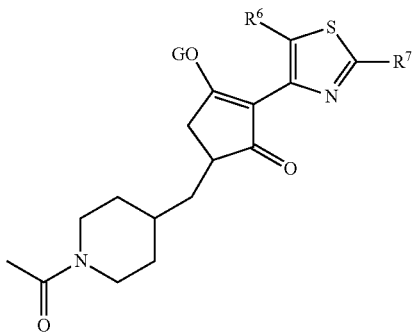

where G, is hydrogen, and $R^6$ and $R^7$ are as described in Table 1.

Table 36 covers 98 compounds of the following type

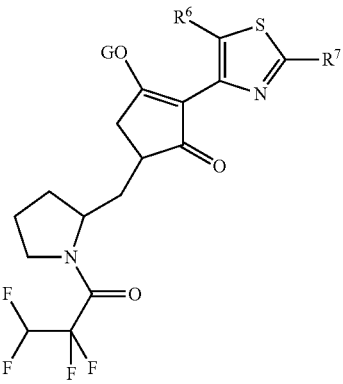

where G, is hydrogen, and $R^6$ and $R^7$ are as described in Table 1.

Table 37 covers 98 compounds of the following type

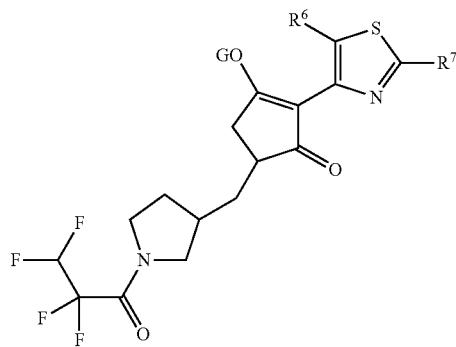

where G, is hydrogen, and $R^6$ and $R^7$ are as described in Table 1.

Table 38 covers 98 compounds of the following type

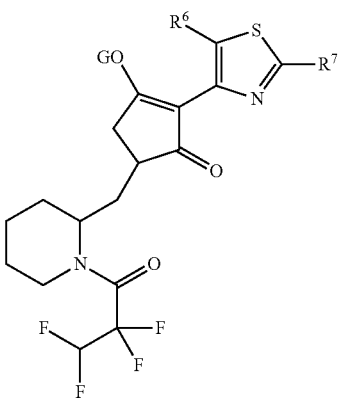

where G, is hydrogen, and $R^6$ and $R^7$ are as described in Table 1.

Table 39 covers 98 compounds of the following type

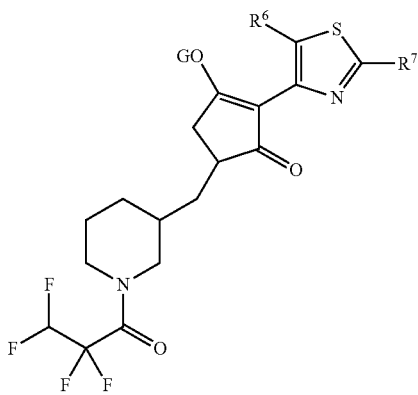

where G, is hydrogen, and $R^6$ and $R^7$ are as described in Table 1.

Table 40 covers 98 compounds of the following type

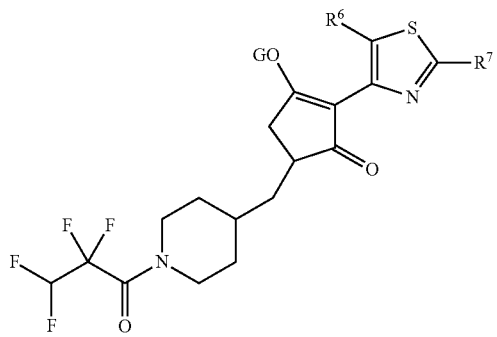

where G, is hydrogen, and $R^6$ and $R^7$ are as described in Table 1.

Table 41 covers 98 compounds of the following type

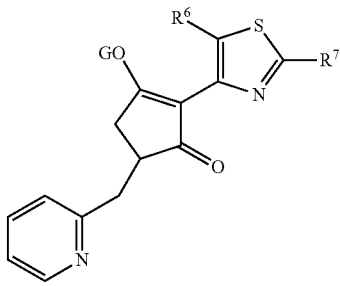

where G, is hydrogen, and $R^6$ and $R^7$ are as described in Table 1.

Table 42 covers 98 compounds of the following type

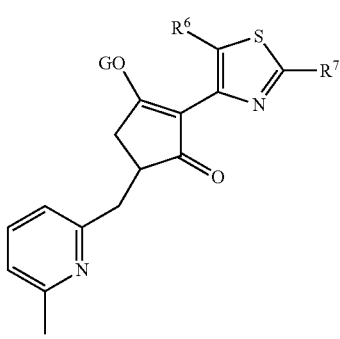

where G, is hydrogen, and $R^6$ and $R^7$ are as described in Table 1.

Table 43 covers 98 compounds of the following type

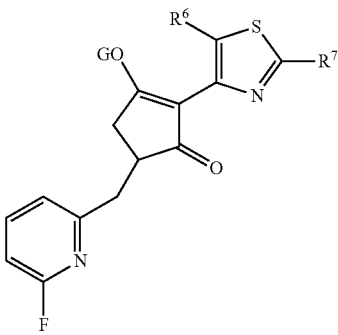

where G, is hydrogen, and $R^6$ and $R^7$ are as described in Table 1.

Table 44 covers 98 compounds of the following type

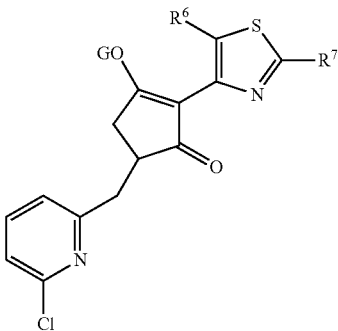

where G, is hydrogen, and $R^6$ and $R^7$ are as described in Table 1.

Table 44 covers 98 compounds of the following type

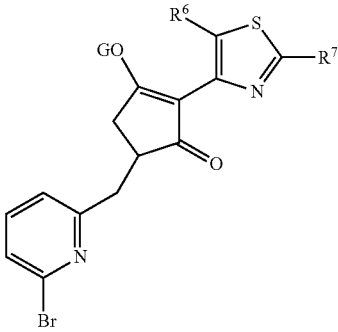

where G, is hydrogen, and $R^6$ and $R^7$ are as described in Table 1.

Table 45 covers 98 compounds of the following type

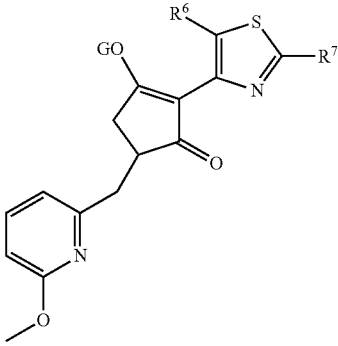

where G, is hydrogen, and $R^6$ and $R^7$ are as described in Table 1.

Table 46 covers 98 compounds of the following type

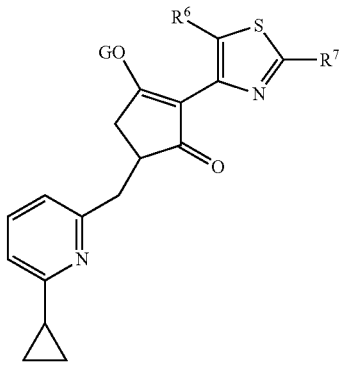

where G, is hydrogen, and $R^6$ and $R^7$ are as described in Table 1.

Table 47 covers 98 compounds of the following type

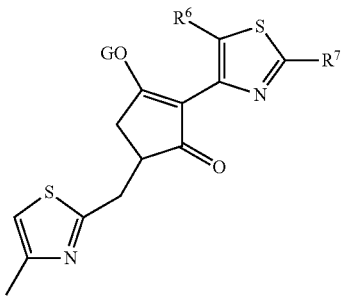

where G, is hydrogen, and $R^6$ and $R^7$ are as described in Table 1.

Table 48 covers 98 compounds of the following type

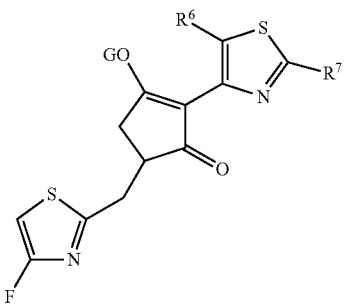

where G, is hydrogen, and $R^6$ and $R^7$ are as described in Table 1.

Table 49 covers 98 compounds of the following type

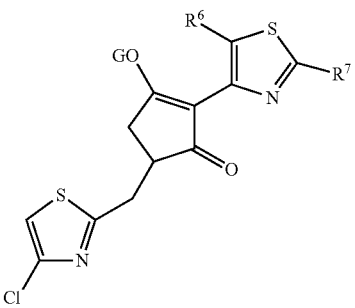

where G, is hydrogen, and $R^6$ and $R^7$ are as described in Table 1.

Table 50 covers 98 compounds of the following type

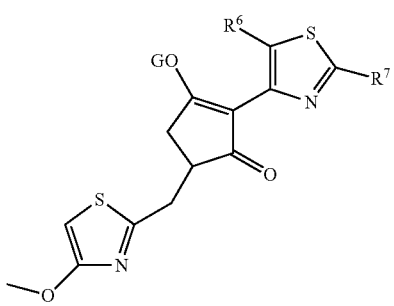

where G, is hydrogen, and $R^6$ and $R^7$ are as described in Table 1.

Table 51 covers 98 compounds of the following type

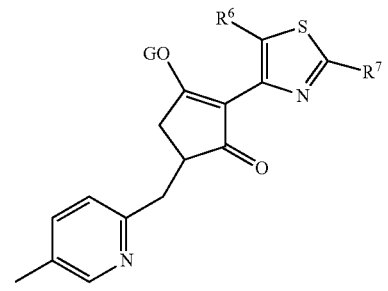

where G, is hydrogen, and $R^6$ and $R^7$ are as described in Table 1.

Table 52 covers 98 compounds of the following type

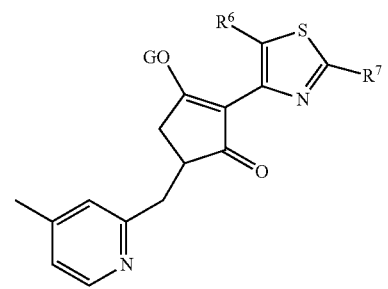

where G, is hydrogen, and $R^6$ and $R^7$ are as described in Table 1.

Table 54 covers 98 compounds of the following type

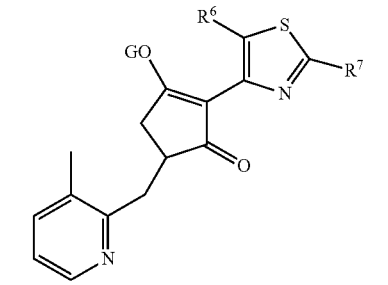

where G, is hydrogen, and $R^6$ and $R^7$ are as described in Table 1.

Table 55 covers 98 compounds of the following type

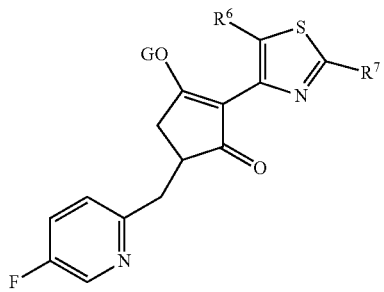

where $G_1$ is hydrogen, and $R^6$ and $R^7$ are as described in Table 1.

BIOLOGICAL EXAMPLES

Example A

Seeds of a variety of test species are sown in standard soil in pots. After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethylene sorbitan monolaurate, CAS RN 9005-64-5).

The test plants are then grown in a glasshouse under controlled conditions in a glasshouse (at 24/16° C., day/night; 14 hours light; 65% humidity) and watered twice daily. After 13 days for pre and post-emergence, the test is evaluated (100=total damage to plant; 0=no damage to plant).

Test Plants:
*Lolium perenne* (LOLPE), *Alopecurus myosuroides* (ALOMY), *Echinochloa crus-galli* (ECHCG), *Avena fatua* (AVEFA)

Post-Emergence Activity

| Compound Number | Rate g/ha | LOLPE | ALOMY | ECHCG | AVEFA |
|---|---|---|---|---|---|
| A1 | 250 | 0 | 10 | 10 | 0 |
| A2 | 250 | 10 | 10 | 20 | 0 |
| A3 | 250 | 0 | 10 | 20 | 0 |
| A4 | 250 | 0 | 20 | 70 | 0 |
| A5 | 250 | 30 | 50 | 80 | 50 |
| A6 | 250 | 0 | 50 | 60 | 0 |
| A7 | 250 | 60 | 90 | 100 | 100 |
| A8 | 250 | 50 | 50 | 90 | 50 |
| A9 | 250 | 40 | 20 | 100 | 60 |
| A10 | 250 | 10 | 20 | 70 | 0 |
| A11 | 250 | 0 | 10 | 80 | 0 |
| A12 | 250 | 100 | 100 | 100 | 90 |
| A13 | 250 | 0 | 10 | 20 | 10 |
| A15 | 250 | 0 | 10 | 20 | 0 |
| A16 | 250 | 100 | 90 | 100 | 100 |
| A17 | 250 | 100 | 90 | 100 | 90 |
| A18 | 250 | 100 | 100 | 100 | 100 |
| A19 | 250 | 0 | 20 | 40 | 10 |
| A20 | 250 | 90 | 80 | 100 | 90 |
| A21 | 250 | 60 | 70 | 90 | 30 |
| A22 | 250 | 50 | 70 | 90 | 60 |
| A23 | 250 | 100 | 90 | 100 | 100 |
| A24 | 250 | 90 | 100 | 100 | 90 |
| A25 | 250 | 100 | 100 | 100 | 100 |

Pre-Emergence Activity

| Compound Number | Rate g/ha | LOLPE | ALOMY | ECHCG | AVEFA |
|---|---|---|---|---|---|
| A1 | 10 | 10 | 50 | 0 | A1 |
| A7 | 80 | 70 | 100 | 70 | A7 |
| A8 | 80 | 50 | 100 | 60 | A8 |
| A9 | 70 | 10 | 100 | 50 | A9 |
| A12 | 100 | 100 | 100 | 90 | A12 |
| A16 | 90 | 90 | 100 | 80 | A16 |
| A17 | 100 | 70 | 100 | 50 | A17 |
| A18 | 100 | 80 | 100 | 90 | A18 |
| A20 | 70 | 40 | 100 | 20 | A20 |
| A21 | 90 | 40 | 90 | 10 | A21 |
| A22 | 60 | 40 | 70 | 20 | A22 |
| A23 | 100 | 90 | 100 | 90 | A23 |
| A24 | 100 | 60 | 100 | 60 | A24 |
| A25 | 90 | 70 | 100 | 70 | A25 |

Example B

Seeds of the Winter Wheat variety 'Hereward' were sown in standard soil in pots. After 8 days cultivation under controlled conditions in a glasshouse (at 24/16° C., day/night; 14 hours light; 65% humidity), the plants were sprayed post-emergence with an aqueous spray solution derived from the formulation of the technical active ingredient in acetone/water (50:50) solution containing 0.5% Tween 20 (polyoxyethylene sorbitan monolaurate, CAS RN 9005-64-5).

Seeds of the Winter Wheat variety 'Hereward' were seed treated with a wettable powder formulation of the cereal herbicide safener, cloquintocet mexyl, at a rate of 0.5 grams per kilogram of dry seed prior to the initiation of glasshouse testing. One seed was sown per 1.5 inch plastic pot into a sandy loam soil at a depth of 1 cm, 8 days prior to application of the test compounds and was watered and grown under controlled conditions in a glasshouse (at 24/16° C., day/night; 14 hours light; 65% humidity). The plants were sprayed post-emergence with an aqueous spray solution derived from the formulation of the technical active ingredient in acetone/water (50:50) solution containing 0.5% Tween 20 (polyoxyethylene sorbitan monolaurate, CAS RN 9005-64-5).

The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

| Compound Number | Rate g/ha | Winter Wheat (Hereward) | Winter Wheat (Hereward) + cloquintocet mexyl |
|---|---|---|---|
| A1 | 250 | 20 | 0 |
| A6 | 250 | 10 | 0 |
| A7 | 250 | 90 | 40 |
| A8 | 250 | 20 | 0 |
| A9 | 250 | 50 | 0 |
| A12 | 250 | 70 | 80 |
| A15 | 250 | 10 | 0 |
| A16 | 250 | 60 | 60 |
| A17 | 250 | 60 | 40 |
| A18 | 250 | 80 | 90 |
| A20 | 250 | 70 | 70 |
| A21 | 250 | 20 | 10 |
| A22 | 250 | 60 | 10 |
| A23 | 250 | 80 | 60 |
| A24 | 250 | 70 | 0 |
| A25 | 250 | 80 | 40 |

The invention claimed is:
1. A compound of formula I

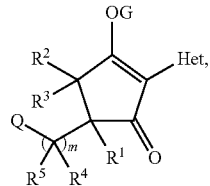

(I)

wherein:
G is hydrogen or an agriculturally acceptable metal, sulfonium, ammonium or latentiating group; and
$R^1$ is hydrogen; and
$R^4$ and $R^5$ independently are hydrogen or methyl; and
$R^2$ and $R^3$ are hydrogen; and
Q is a group selected from formulae $Q_1$, $Q_2$, $Q_3$, $Q_4$, $Q_5$, $Q_6$, $Q_7$, $Q_{25}$, $Q_{26}$, $Q_{27}$, $Q_{28}$, $Q_{29}$, $Q_{31}$, $Q_{32}$, $Q_{33}$, $Q_{34}$, $Q_{35}$, $Q_{36}$, $Q_{37}$, $Q_{38}$, $Q_{39}$, $Q_{40}$, $Q_{41}$, $Q_{42}$, $Q_{43}$, $Q_{44}$, $Q_{45}$, $Q_{46}$, $Q_{47}$, $Q_{86}$, $Q_{87}$, $Q_{88}$, $Q_{89}$, $Q_{90}$, $Q_{106}$, and $Q_{107}$ as defined below:

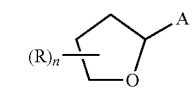 $Q_1$

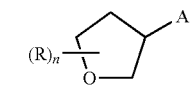 $Q_2$

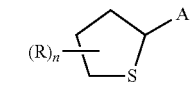 $Q_3$

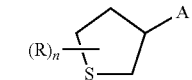 $Q_4$

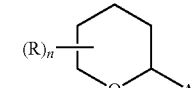 $Q_5$

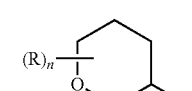 $Q_6$

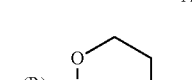 $Q_7$

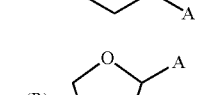 $Q_{25}$

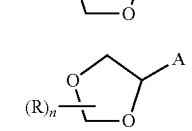 $Q_{26}$

-continued

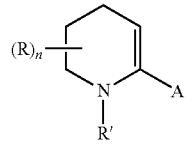 $Q_{16}$

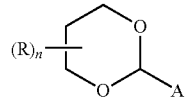 $Q_{27}$

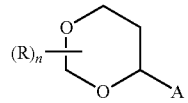 $Q_{28}$

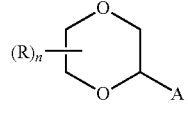 $Q_{29}$

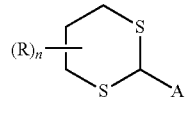 $Q_{31}$

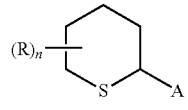 $Q_{32}$

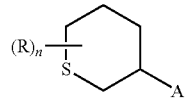 $Q_{33}$

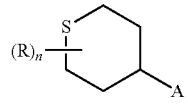 $Q_{34}$

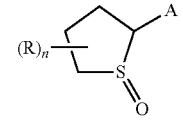 $Q_{35}$

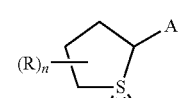 $Q_{36}$

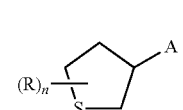 $Q_{37}$

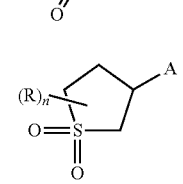 $Q_{38}$

143
-continued

Q39 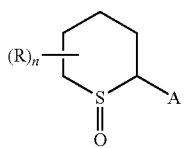

Q40 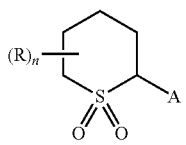

Q41 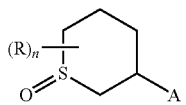

Q42 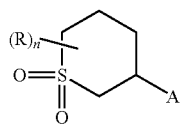

Q43 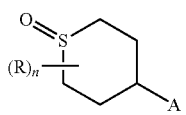

Q44 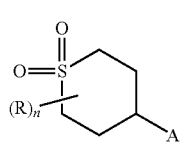

Q46 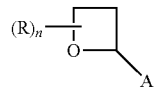

Q47 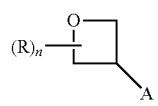

Q86 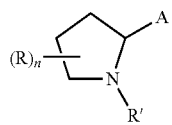

Q87 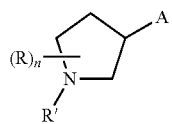

Q88 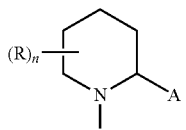

Q89 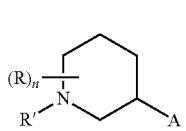

144
-continued

Q90 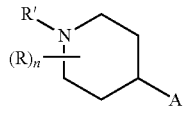

Q106 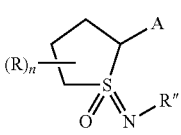

Q107 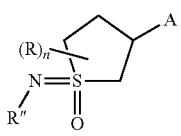

Q107 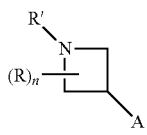

wherein:

R is hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, or nitro; or phenyl or phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl; or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl R' is hydrogen, $C_1$-$C_6$alkyl, $C_1$-$C_6$haloalkyl, $C_3$-$C_7$cycloalkyl, $C_1$-$C_6$alkoxy, $C_1$-$C_6$haloalkoxy, $C_1$-$C_6$alkylsulfinyl, $C_1$-$C_6$alkylsulfonyl, $C_1$-$C_6$alkylcarbonyl, $C_1$-$C_6$haloalkylcarbonyl, $C_1$-$C_6$alkoxycarbonyl, $C_1$-$C_6$alkylaminocarbonyl, $C_2$-$C_8$dialkylaminocarbonyl, $C_6$-$C_{10}$arylsulfonyl, $C_6$-$C_{10}$arylcarbonyl, $C_6$-$C_{10}$arylaminocarbonyl, $C_7$-$C_{16}$arylalkylaminocarbonyl, $C_1$-$C_9$heteroarylsulfonyl, $C_1$-$C_9$heteroarylcarbonyl, $C_1$-$C_9$heteroarylaminocarbonyl, $C_2$-$C_{15}$heteroarylalkylaminocarbonyl;

n is 0, 1 or 2; and

A denotes the position of attachment to the —$(CR^4R^5)_m$— moiety;

or Q is an heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl; and m is 1; and Het is a group selected from the formulae $Het_1$ to $Het_{10}$:

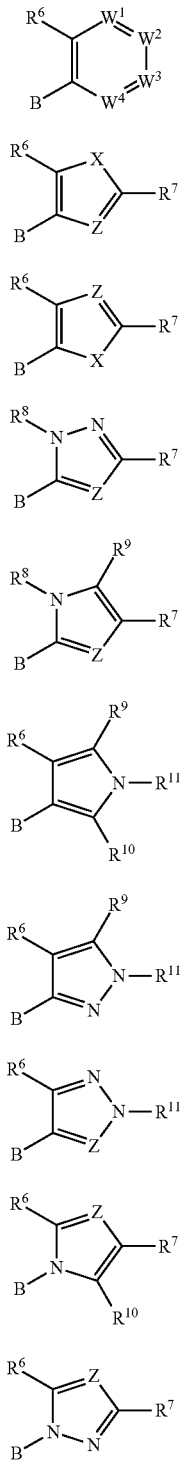

wherein:
B designates the point of attachment to the ketoenol moiety;
$W^1$ is N or $CR^9$; and
either $W^2$ is N or $CR^7$, and $W^3$ is $CR^7$;
or $W^2$ is $CR^7$; and $W^3$ is N or $CR^7$; and
$W^4$ is N or $CR^{19}$;
with the proviso that at least one of $W^1$, $W^2$, $W^3$ or $W^4$ is N;
X is O, S, or $NR^{12}$;
Z is N or $CR^{13}$;
wherein
$R^6$ is halogen, $C_1$-$C_2$alkyl, $C_1$-$C_2$haloalkyl, vinyl, ethynyl or methoxy;
$R^7$ is $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_3$-$C_6$ cycloalkyl, $C_5$-$C_6$cycloalkenyl, halogen, $C_1$-$C_6$alkoxy, $C_1$-$C_6$alkoxy-$C_1$alkyl, or $C_1$-$C_6$haloalkoxy; or optionally substituted heteroaryl wherein the optional substituents are selected from halogen, $C_1$-$C_2$ alkyl, $C_1$-$C_2$ alkoxy, $C_1$-$C_2$ haloalkyl, $C_1$-$C_2$ haloalkoxy, cyano or nitro; or phenyl, substituted once, twice or three times, by halogen, $C_1$-$C_2$ alkyl, $C_1$-$C_2$ alkoxy, $C_1$-$C_2$ haloalkyl, $C_1$-$C_2$ haloalkoxy or cyano;
$R^8$ is methyl, ethyl, $C_2$alkenyl, $C_2$alkynyl or $C_1$ haloalkyl;
$R^9$ is hydrogen, methyl, halomethyl, or halogen;
$R^{10}$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl or cyano;
$R^{11}$ is methyl, ethyl, halomethyl, or haloethyl; or optionally substituted heteroaryl wherein the optional substituents are selected from halogen, $C_1$-$C_2$ alkyl, $C_1$-$C_2$ alkoxy, $C_1$-$C_2$ haloalkyl, $C_1$-$C_2$ haloalkoxy, cyano or nitro; or phenyl, substituted once, twice or three times, by halogen, $C_1$-$C_2$ alkyl, $C_1$-$C_2$ alkoxy, $C_1$-$C_2$ haloalkyl, $C_1$-$C_2$ haloalkoxy or cyano;
$R^{12}$ is hydrogen, methyl, ethyl, or halomethyl; and
$R^{13}$ is hydrogen, methyl, ethyl, halomethyl, haloethyl, halogen, cyano or nitro;
and wherein when G is a latentiating group then G is selected from the groups phenyl$C_1$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$alkenyl, $C_3$haloalkenyl, $C_3$alkynyl, $C(X^a)$—$R^a$, $C(X)$—$X^b$—$R^b$, $C(X^d)$—$N(R^b)$—$R^d$, —$SO_2$—$R^e$, —$P(X^e)(R^f)$—$R^g$ and $CH_2$—$X^f$—$R^h$;
wherein $X^a$, $X^b$, $X^c$, $X^d$, $X^e$ and $X^f$ are independently of each other oxygen or sulfur;
and wherein $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_6$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N-($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; or phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N-($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl; or phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N-($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_5$cycloalkyl; or phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or $C_3$-$C_7$cycloalkylamino, di-$C_3$-$C_7$cycloalkylamino or $C_3$-$C_7$cycloalkoxy;

or $R^c$ and $R^d$ join together to form a 3-7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_5$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_5$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_5$dialkylaminocarbonyl($C_1$-$C_5$)alkyl, $C_1$-$C_5$alkylcarbonylamino($C_1$-$C_5$)alkyl, N-($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_5$cycloalkyl; or phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro; or heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; or diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_5$dialkylamino;

$R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino ($C_1$-$C_5$)alkyl, $C_2$-$C_5$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N-($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; or phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; or heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; or diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; or phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_8$dialkylamino; or benzyloxy or phenoxy, wherein the benzyl and phenyl groups are in turn optionally substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N-($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl; or phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

and wherein the term "heteroaryl" means an aromatic ring system containing at least one heteroatom and consisting either of a single ring or of two fused rings;

and wherein the compound is optionally an agronomically acceptable salt thereof.

2. A compound according to claim 1, wherein $R^4$ and $R^5$ are hydrogen.

3. A compound according to claim 1, wherein Q is a group selected from formulae $Q_1$, $Q_2$, $Q_3$, $Q_4$, $Q_5$, $Q_6$, $Q_7$, $Q_{25}$, $Q_{26}$, $Q_{27}$, $Q_{28}$, $Q_{29}$, $Q_{86}$, $Q_{87}$, $Q_{88}$, $Q_{89}$, and $Q_{90}$ as defined in claim 1.

4. A compound according to claim 3, wherein
Q is a group selected from formulae $Q_1$, $Q_2$, $Q_3$, $Q_4$, $Q_5$, $Q_6$, $Q_7$, $Q_{25}$, $Q_{26}$, $Q_{27}$, $Q_{28}$, $Q_{29}$, $Q_{86}$, $Q_{87}$, $Q_{88}$, $Q_{89}$, and $Q_{90}$ as defined in claim 1;
R and R' are independently hydrogen, $C_1$-$C_4$alkyl, $C_1$-$C_4$haloalkyl, $C_1$-$C_4$alkoxy or $C_1$-$C_4$haloalkoxy; and
n is 0.

5. A compound according to claim 1, wherein Q is thienyl, furyl, oxazolyl, isoxazolyl, benzofuryl, thiazolyl, oxazolyl, isothiazolyl, benzothienyl, benzoisothienyl, benzothiazolyl, benzisothiazolyl, benzoxazolyl or benzisoxazolyl, where these rings are optionally substituted one or two times by fluoro, chloro, bromo, methyl, methoxy, cyano or trifluoromethyl.

6. A compound according to claim 1, wherein Q is pyridyl, pyrimidinyl, pyridazinyl, quinolinyl, isoquinolinyl, cinnolinyl, phthalazinyl, quinazolinyl or quinoxalinyl, where these rings are optionally substituted one or two times by fluoro, chloro, bromo, methyl, methoxy, cyano or trifluoromethyl.

7. A compound according to claim 1, wherein Het is a substituted monocyclic 5-membered sulfur or nitrogen containing heteroaromatic ring.

8. A compound according to claim 7, wherein Het is a monocyclic 5-membered sulfur and nitrogen containing heteroaromatic ring.

9. A compound according to claim 1, wherein Het is a group selected from the formulae $Het_1$ to $Het_{10}$, wherein:
B designates the point of attachment to the ketoenol moiety;
$W^1$ is N or $CR^9$; and
either $W^2$ is N or $CR^7$, and $W^3$ is $CR^7$;
or $W^2$ is $CR^7$; and $W^3$ is N or $CR^7$; and
$W^4$ is N or $CR^{10}$;
with the proviso that at least one of $W^1$, $W^2$, $W^3$ or $W^4$ is N;
X is O, S, or $NR^{12}$;
Z is N or $CR^{13}$;
wherein
$R^6$ is halogen, $C_1$-$C_2$alkyl, $C_1$-$C_2$haloalkyl, vinyl, ethynyl, or methoxy;

$R^7$ is phenyl, substituted once, twice or three times, by halogen, $C_1$-$C_2$ alkyl, $C_1$-$C_2$ alkoxy, $C_1$-$C_2$ haloalkyl, $C_1$-$C_2$ haloalkoxy or cyano;

$R^8$ is methyl or ethyl;

$R^9$ is hydrogen, methyl, halomethyl or halogen;

$R^{10}$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl or cyano;

$R^{11}$ is phenyl, substituted once, twice or three times, by halogen, $C_1$-$C_2$ alkyl, $C_1$-$C_2$ alkoxy, $C_1$-$C_2$ haloalkyl, $C_1$-$C_2$ haloalkoxy or cyano;

$R^{12}$ is hydrogen, methyl, ethyl or halomethyl; and $R^{13}$ is hydrogen, methyl, ethyl, halomethyl, haloethyl, halogen, cyano or nitro.

10. A compound according to claim 9, wherein:

$R^6$ is methyl or ethyl;

$R^8$ is methyl or ethyl;

$R^9$ is hydrogen; and $R^{10}$ is hydrogen, halogen, methyl or ethyl.

11. A compound according to claim 1, wherein when G is a latentiating group then G is a group —C($X^a$)—$R^a$ or —C($X^b$)—$X^c$—$R^b$.

12. A compound according to claim 1, wherein when G is a latentiating group then G is a group —C($X^a$)—$R^a$ or —C($X^b$)—$X^c$—$R^b$, wherein $R^a$ is hydrogen or $C_1$-$C_{18}$alkyl, $R^b$ is $C_1$-$C_{18}$alkyl, and the meanings of $X^a$, $X^b$ and $X^c$ are as defined in claim 1.

13. A compound according to claim 1, wherein G is hydrogen, an alkali metal or an alkaline earth metal.

14. A compound according to claim 1, wherein:

$R^1$ is hydrogen;

$R^2$ and $R^3$ are hydrogen;

$R^4$ and $R^5$ independently are hydrogen or methyl; and

Q is pyridyl, pyrimidinyl, pyridazinyl, quinolinyl, isoquinolinyl, cinnolinyl, phthalazinyl, quinazolinyl or quinoxalinyl, where these rings are optionally substituted one or two times by fluoro, chloro, bromo, methyl, methoxy, cyano or trifluoromethyl;

or Q is thienyl, furyl, oxazolyl, isoxazolyl, benzofuryl, thiazolyl, oxazolyl, isothiazolyl, benzothienyl, benzoisothienyl, benzothiazolyl, benzisothiazolyl, benzoxazolyl or benzisoxazolyl, where these rings are optionally substituted one or two times by fluoro, chloro, bromo, methyl, methoxy, cyano or trifluoromethyl; and m is 1;

Het is a group $Het_2$

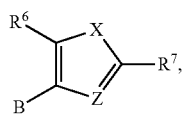

wherein X is S, Z is N, $R^6$ is methyl or ethyl, $R^7$ is 4-chlorophenyl or 4-bromophenyl, and B designates the point of attachment to the ketoenol moiety; and G is hydrogen, an alkali metal or an alkaline earth metal.

15. A compound according to claim 14, wherein $R^1$ to $R^5$ are hydrogen and G is hydrogen.

16. A compound according to claim 1, wherein $R^1$ to $R^5$ are hydrogen; G is hydrogen, an alkali or an alkaline earth metal; m is 1; and Q is group selected from formulae $Q_1$ to $Q_7$ as defined below:

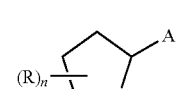

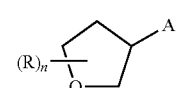

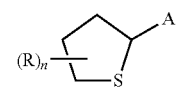

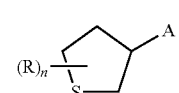

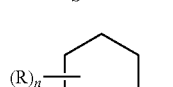

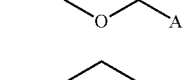

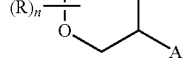

wherein n is 0 and A designates the point of attachment to the —($CR^4R^5$)$_m$ moiety;

or Q is pyridyl; and

Het is a group of the formula $Het_2$

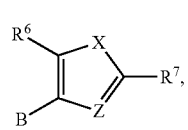

wherein X is S, Z is N, $R^6$ is methyl or ethyl, $R^7$ is phenyl substituted by halogen, and B designates the point of attachment to the ketoenol moiety;

or Het is a group of the formula $Het_{10}$

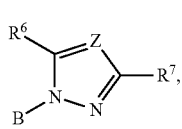

wherein Z is CH or C—$CH_3$, $R^6$ is methyl or ethyl, $R^7$ is phenyl substituted by halogen, and B designates the point of attachment to the ketoenol moiety.

17. A compound according to claim 16, wherein Q is a group of the formula $Q^7$ or pyridine-2-yl, and Het is a group of the formula $Het_2$ or $Het_{10}$, wherein $R^7$ is 4-chlorophenyl.

18. A compound which is one of compounds A5, A6, A8, A12, A16, A18, A20, or A25 as shown below, or an agriculturally or agronomically acceptable salt thereof:

(A5)
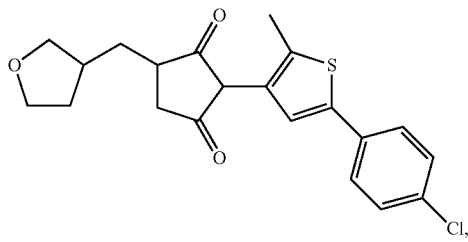

(A6)
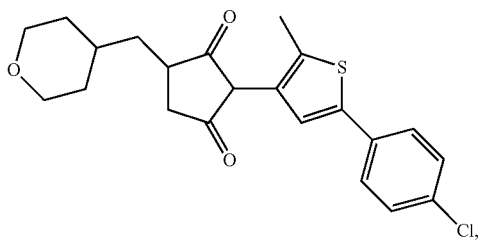

(A12)
(A16)
(A18)
(A20)
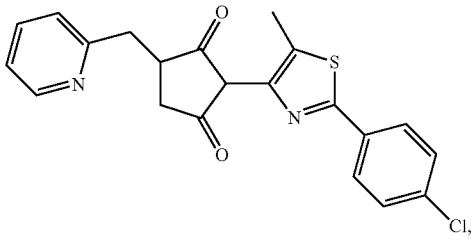
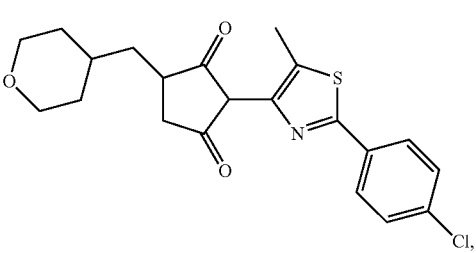
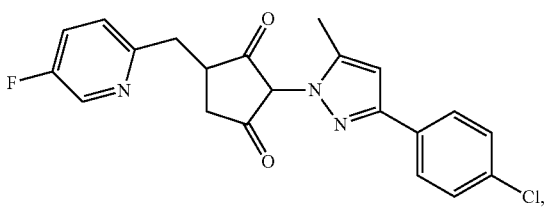

(A25)

19. A herbicidal composition, which comprises a herbicidally effective amount of a compound of formula I as defined in claim 1, and optionally a further herbicide as mixture partner for the compound of formula I, or optionally a safener, or both.

20. A herbicidal composition according to claim 19, which comprises a herbicidally effective amount of a compound of formula I as defined in claim 1, a safener, and optionally a further herbicide as mixture partner for the compound of formula I,
wherein the safener is benoxacor, cloquintocet-mexyl, cyprosulfamide, mefenpyr-diethyl or N-(2-methoxy-benzoyl)-4-[(methylaminocarbonyl)amino]benzene-sulfonamide.

21. A compound according to claim 4, wherein Q is a group selected from formulae $Q_1$, $Q_2$, $Q_3$, $Q_4$, $q_5$, $Q_6$ and $Q_7$.

22. A compound according to claim 3, wherein n is 0.

23. A compound according to claim 1, wherein Q is a 5- or 6-membered heteroaryl or is a 5-or 6-membered heteroaryl which is substituted one to three times by fluoro, chloro, bromo, methyl, methoxy, cyano or trifluoromethyl.

24. A compound according to claim 1, wherein Het is:
a group of the formula $Het_2$, wherein X is S and Z is N and $R^6$ and $R^7$ are as defined in claim 1;
a group of the formula $Het_{10}$, wherein Z is $CR^{13}$ and $R^6$, $R^7$ and $R^{13}$ are as defined in claim 1; or
a group of the formula $Het_2$, wherein X is S and Z is $CR^{13}$ and $R^6$, $R^7$ and $R^{13}$ are as defined in claim 1.

25. A compound according to claim 1, wherein Het is a group of the formula $Het_{10}$, wherein Z is $CR^{13}$ and $R^6$, $R^7$ and $R^{13}$ are as defined in claim 1.

26. A herbicidal composition according to claim 19, which comprises the further herbicide as mixture partner for the compound of formula I.

27. A compound according to claim 9, wherein Het is:
a group of the formula $Het_2$, wherein X is S and Z is N and $R^6$ and $R^7$ are as defined in claim 9;
a group of the formula $Het_{10}$, wherein Z is $CR^{13}$ and $R^6$, $R^7$ and $R^{13}$ are as defined in claim 9; or
a group of the formula $Het_2$, wherein X is S and Z is $CR^{13}$ and $R^6$, $R^7$ and $R^{13}$ are as defined in claim 9.

28. A compound which is one of compounds A7, A9, A17, A21, A22, A23 or A24, as shown below, or an agriculturally or agronomically acceptable salt thereof:

(A7)
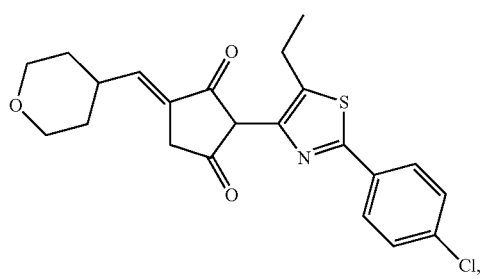
(A9)
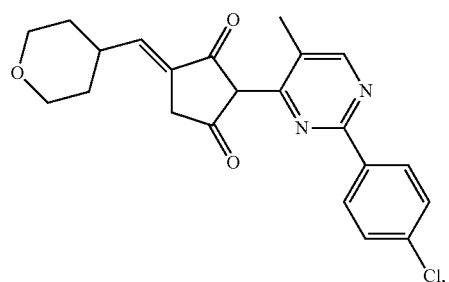
(A17)
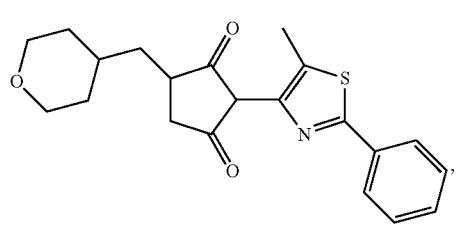
(A21)
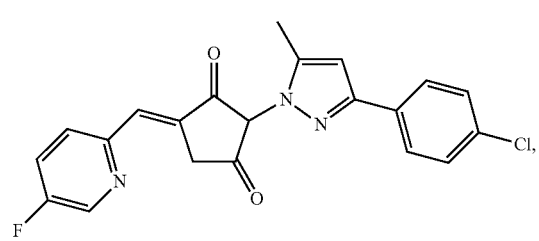
(A22)
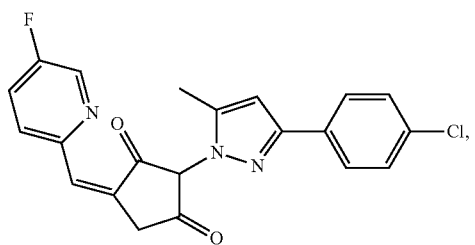
(A23)
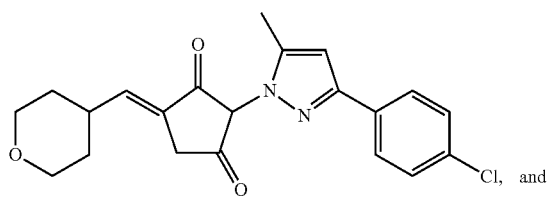
and
(A24)
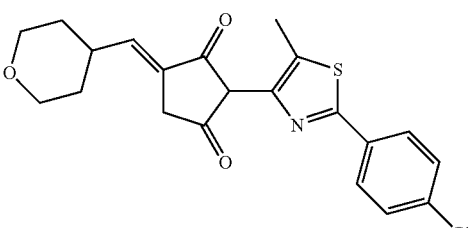
* * * * *